(12) United States Patent
Romeuf et al.

(10) Patent No.: US 11,345,730 B2
(45) Date of Patent: May 31, 2022

(54) CHIMERIC PROTEIN IN THE TREATMENT OF AMYLOIDOSIS

(71) Applicants: CENTRE NATIONAL DE LA RECHERCHE SCIENTIFIQUE (CNRS), Paris (FR); UNIVERSITÉ DE LIMOGES, Limoges (FR)

(72) Inventors: Christophe de Romeuf, Lambersart (FR); Christophe Sirac, Limoges (FR); Jean-Claude Brouet, Paris (FR)

(73) Assignees: CENTRE NATIONAL DE LA RECHERCHE SCIENTIFIQUE (CNRS), Paris (FR); UNIVERSITÉ DE LIMOGES, Limoges (FR)

( * ) Notice: Subject to any disclaimer, the term of this patent is extended or adjusted under 35 U.S.C. 154(b) by 0 days.

(21) Appl. No.: 15/977,489

(22) Filed: May 11, 2018

(65) Prior Publication Data

US 2018/0298071 A1 Oct. 18, 2018

Related U.S. Application Data

(62) Division of application No. 15/032,542, filed as application No. PCT/IB2014/065734 on Oct. 31, 2014, now abandoned.

(30) Foreign Application Priority Data

Oct. 31, 2013 (FR) .................................. 13 60702

(51) Int. Cl.
*C07K 16/18* (2006.01)
*C07K 16/46* (2006.01)
(Continued)

(52) U.S. Cl.
CPC ...... *C07K 14/4711* (2013.01); *A61K 38/1716* (2013.01); *A61K 45/06* (2013.01);
(Continued)

(58) Field of Classification Search
None
See application file for complete search history.

(56) References Cited

U.S. PATENT DOCUMENTS

| | | | |
|---|---|---|---|
| 2009/0191196 A1* | 7/2009 | Pepys | A61P 25/28 424/133.1 |
| 2009/0252729 A1 | 10/2009 | Farrington et al. | |
| 2010/0317596 A1 | 12/2010 | Willett et al. | |

FOREIGN PATENT DOCUMENTS

| | | |
|---|---|---|
| WO | 9505394 A1 | 2/1995 |
| WO | 2002042462 A2 | 5/2002 |

(Continued)

OTHER PUBLICATIONS

Rosenzweig et al., Light chain (AL) amyloidosis: update on diagnosis and management. Journal of Hematology & Oncology volume 4, Article No. 47 (2011) (Year: 2011).*

(Continued)

*Primary Examiner* — Aurora M Fontainhas
(74) *Attorney, Agent, or Firm* — Morrison & Foerster LLP

(57) ABSTRACT

The present invention relates to a chimeric protein comprising at least one human amyloid P component and at least one fragment of an Fc region of a human antibody, the human amyloid P component and the fragment of an Fc region with which it is associated being bound to each other by means of a hinge region.

15 Claims, 11 Drawing Sheets

Specification includes a Sequence Listing.

(51) Int. Cl.
| | |
|---|---|
| *C07K 14/47* | (2006.01) |
| *C12N 15/62* | (2006.01) |
| *A61K 38/17* | (2006.01) |
| *A61K 45/06* | (2006.01) |
| *G01N 33/68* | (2006.01) |

(52) U.S. Cl.
CPC .............. *C07K 14/47* (2013.01); *C12N 15/62* (2013.01); *G01N 33/6896* (2013.01); *C07K 2319/00* (2013.01); *C07K 2319/30* (2013.01); *G01N 2800/2821* (2013.01); *G01N 2800/2828* (2013.01); *G01N 2800/2835* (2013.01)

(56) References Cited

FOREIGN PATENT DOCUMENTS

| | | |
|---|---|---|
| WO | 2008143954 A2 | 11/2008 |
| WO | 2009000926 A1 | 12/2008 |
| WO | 2010106160 A2 | 9/2010 |
| WO | 2010106180 A3 | 12/2010 |
| WO | 2013096847 A1 | 6/2013 |

OTHER PUBLICATIONS

Bodin et al., "Antibodies to human serum amyloid P component eliminate visceral amyloid deposits," Nature, vol. 468, No. 4, pp. 93-97, Nov. 2010.

International Search Report issued in application No. PCT/IB2014/065734 dated Mar. 16, 2015.

Janeway et al., "The structure of a typical antibody molecule," Immunobiology: The Immune System in Health and Disease, 5th edition, New York: Garland Science, 2001, https://www.ncbi.nlm.nih.gov/books/NBK27144.

Picken, "New insights into systemic amyloidosis: the importance of diagnosis of specific type," Current Opinion in Nephrology and Hypertension, vol. 16, No. 3, pp. 196-203, May 2007.

Bharadwaj, D. et al. (Jun. 2001). "Serum Amyloid P Component Binds To Fcγ Receptors and Opsonizes Particles For Phagocytosis," The Journal of Immunology 166(11):6735-6741.

Pilling, D. et al. (Oct. 16, 2018). "The Development of Serum Amyloid P as a Possible Therapeutic," Frontiers in immunology 9:2328, 1-10.

Tennent, G.A. et al. (May 1995), "Serum Amyloid P Component Prevents Proteolysis of The Amyloid Fibrils of Alzheimer Disease and Systemic Amyloidosis," Proceedings of the National Academy of Sciences 92(10):4299-4303.

Czajkowsky, D.M. et al. (Oct. 2012)."Fc-Fusion Proteins: New Developments and Future Perspectives," EMBO Mol. Med. 4(10):1015-1028.

Lagassé, H.D. et al. (Jul. 2019). "Fc-Fusion Drugs Have Fcγr/C1q Binding and Signaling Properties That May Affect Their Immunogenicity," The AAPS Journal 21(4):62, 10 pages.

Shoji-Hosaka, E. et al. (2006). "Enhanced Fc-Dependent Cellular Cytotoxicity of Fc Fusion Proteins Derived from TNF Receptor II and LFA-3 by Fucose Removal from Asn-Linked Oligosaccharides," J. Biochem. 140(6):777-783.

\* cited by examiner

CHIMERIC PROTEIN IN THE TREATMENT OF AMYLOIDOSIS

CROSS-REFERENCE TO RELATED APPLICATIONS

This application is a division of U.S. application Ser. No. 15/032,542, filed on Apr. 27, 2016, now abandoned, which is a U.S. national phase application under 35 U.S.C. § 371 of International Application No. PCT/IB2014/065734, filed on Oct. 31, 2014, which claims priority to French Application No. 13 60702, filed on Oct. 31, 2013.

FIELD OF THE INVENTION

The present invention relates to the field of obtaining a specific chimeric protein for therapeutic use, in particular for treating amyloidosis, in particular amyloidosis of AL type.

PRIOR ART

Amyloidosis is a vast group of diseases belonging to the group of protein conformational diseases encompassing other diseases such as, for example, Alzheimer's disease, transmissible spongiform encephalopathies, Huntington's disease or type II diabetes.

Amyloidosis is a rare disease which is characterized by the presence of deposits of insoluble proteins which adopt an abnormal fibrillar conformation in the tissues. Most commonly, it is serum precursor protein fragments which are the cause thereof. Many organs can be affected by these extracellular deposits, called "amyloid substance". The main organs affected by the amyloid deposits are the kidney, the heart, the digestive tract, the liver, the skin, peripheral nerves and the eye. The organs affected by this disease generally have a sizeable volume. In fact, amyloidosis can involve all the organs, and also the central nervous system, so that there are numerous very varied symptoms.

Amyloidosis is a severe disease which can progress to destruction of the affected organs. There are more than 25 proteins capable of forming amyloid deposits.

It is generally accepted that amyloid substance is approximately 90% composed of fibrillar proteins which are characteristic of each variety of amyloidosis. Among the remaining 10%, approximately 5% are composed of glycosaminoglycans (GAGs) and 5% are composed of glycoproteins called amyloid P component (or SAP protein), SAP being constantly present whatever the type of amyloidosis.

Table 1 hereinafter lists the main types of amyloidosis. The latter are named according to the nature of the protein involved, which itself will be denoted by the prefix A (for amyloidosis) and a specific suffix. Thus, amyloid protein derived from immunoglobulin light chains is denoted AL, and the amyloidosis consisting of these chains is called "AL amyloidosis"; likewise, for the ATTR proteins derived from transthyretin, the corresponding amyloidosis is called "ATTR amyloidosis".

TABLE 1

Amyloidosis nomenclature and classification

| Amyloid protein | Precursor | Spread | Syndromes or tissues affected |
|---|---|---|---|
| AL | Ig light chain (κ, λ) | G, L | (Primary) isolated or associated with myeloma or with Waldenstrom disease |
| AH | Ig heavy chain (γ) | G, L | Isolated |
| AA | apoSAA | G, L | (Secondary) infections, chronic inflammations, tumors, TRAPS, FMF, Muckle and Wells syndrome |
| ATTR | Mutated transthyretin, Normal transthyretin | G G | Familial senile |
| Chronic renal Aβ2M | β2-Microglobulin | G | Associated with terminal insufficiency |
| AApoA1 | Apoliproprotein A1 | G L | Familial aortic (intima) |
| AApoA2 | Apoliproprotein A2 | G | Familial |
| AGel | Gelsolin | G | Familial |
| ALys | Lysosym | G | Familial |
| AFib | Fibrinogen | G | Familial |
| ACys | Cystatin C | L | Familial cerebral hemorrhage |
| Aβ | Aβ protein precursor (AβPP) | L | Alzheimer's disease, trisomy 21, familial or sporadic cerebral amyloid angiopathy |
| APrPsc | Prion protein precursor | L | Spongiform encephalopathy |
| ACal | Procalcitonin | L | Thyroid medullary cancer |
| AANF | Natriuretic atrial factor | L | Isolated atrial amyloidosis |
| AIAPP | Amylin | L | Islets of Langerhans of type 2 diabetes, insulinoma |
| AIns* | Insulin | L | Lactrogenic |
| APro* | Prolactin | L | Prolactinoma, pituitary gland senile |
| AKep* | Keratoepithelin | L | Lattice corneal dystrophies |
| Abri* | BRI-L | L | Familial British dementia |
| ALact* | Lactoferrin | L | Seminal vesicle |
| Amed* | Lactadherin | L | Aortic (media) |

FMF: familial Mediterranean fever;
TRAPS: tumor necrosis factor (TNF) receptor-associated periodic syndrome;
Ig: immunoglobulin;
G: generalized amyloidosis;
L: localized amyloidosis;
*non-official nomenclature. Grateau G. *Amyloses* [*Amyloidosis*]. Encyclopédie Orphanet [Orphanet Encyclopedia], May 2001, updated June 2003.

The diagnosis of amyloidosis is based on the identification of the amyloid deposits during anatomical-pathological examination. It therefore requires targeted biopsies, but it is more difficult to gain access to certain organs or there is a not insignificant risk (heart, brain, etc.) Amyloid substances can be specifically recognized using a dye, Congo red, by observing yellow-green dichroic birefringence in polarized light. They can also be recognized by electron microscopy. Following the identification of these amyloid substances, the use of specific antibodies makes it possible to identify the type of amyloidosis under consideration (Ab against SAA, CL kappa and lambda, fibrinogen, TTR, apoA1, apoA2, lysozyme, Ig heavy chains) (Picken M M., Current Opin Nephrol Hypertens, 2007; 16: 196; Vrana J A et al., Blood, 2009; 114: 4957).

Several approaches for treating amyloidosis can be envisioned, namely (1) elimination of the source of production, (2) inhibition of fibril elongation or (3) active elimination of the amyloid deposits.

Treating the cause of the production of the abnormal protein (i.e. approach (1) above) is the best means of limiting the progression of the amyloid disease. On the other hand, at the current time, each type of amyloidosis requires a different treatment.

For AL amyloidosis, the most severe form in which the damage is the most disseminated, the treatment consists in reducing the formation of the amyloid substance deposits.

For this, it is necessary to inhibit as much as possible the production of the monoclonal immunoglobulin responsible for the deposits. Most commonly, a treatment is carried out by chemotherapy (by administration, in particular, of glucocorticoids (dexamethasone) and of antimitotics). The efficacy of the treatment is evaluated by measuring the reduction in the amount of monoclonal light chain in the blood. If this reduction is considerable, the amyloid substance deposits, the formation of which is inhibited, will be gradually eliminated by the organism. This leads to a gradual improvement in the clinical condition. The rate of elimination of the deposits is variable depending on the organ and depending on patients, and generally requires several months to be noticeable. At the current time, there is no treatment that can accelerate the elimination of the deposits. AL amyloidosis can be localized or disseminated, asymptomatic or, on the contrary, can have a dreadful prognosis.

In parallel, specific treatments for compensating for the insufficiency or insufficiencies in terms of operation of the organ(s) affected by the amyloidosis are generally carried out. In the event of the heart or kidneys being severely affected, a transplant may be proposed.

Chemotherapy treatment for AL amyloidosis comprises, however, numerous side effects such as hair loss, diarrhea, nausea or vomiting. Hematological toxicity is the most recurrent and most serious phenomenon and requires constant monitoring of the patient. It consists of a decrease, which may be considerable, in several blood components with sizeable risks: thrombocytopenia caused by a drop in blood platelets with a hemorrhagic risk, anemia, leukopenia with an infectious risk.

At a very advanced stage of AL amyloidosis, the damage in the organs is such that chemotherapy is ineffective. A transplant is then necessary.

For AA amyloidosis, treatment of the underlying inflammation is the most important therapeutic measure. The efficacy of the new anti-inflammatory treatments (anti-TNF, anti-IL1) is in the process of being clinically evaluated. However, for the moment, this amyloidosis remains incurable and fatal, since there is no specific treatment that can eliminate the deposits more rapidly.

In transthyretin amyloidosis (familial amyloidosis), a liver transplant may be proposed for the purpose of eliminating the main source of production of abnormal TTR protein. This treatment has demonstrated its efficacy in stopping the progression of the disease in the vast majority of cases of familial amyloid neuropathies treated at an early stage (90%), this being with an average amount of time passed of 8 years. Furthermore, this treatment is not effective when it is begun at an advanced pathological stage, in particular when there is cardiac involvement.

Regarding the treatment approach consisting in inhibiting fibril elongation (i.e. approach (2) above), it is known practice to use DMSO and colchicine, and I-Dox, anthracycline interacting with the amyloid deposits. However, it appears that these treatments, although they cause a delay in the appearance of the amyloid deposits, inhibit however their elongation little or not at all (Merlini G, Blood 93, 1999: 1112).

Regarding the treatment approach consisting in actively eliminating the amyloid deposits (i.e. approach (3) above), it is known practice to use murine monoclonal antibodies which recognize a conformational epitope of the amyloidosis (11-1F4) (Solomon, Am. J. Path., 2000, 157: 1239). However, it appears that these antibodies do not seem to be very effective.

Moreover, document WO 2009/000926 proposes the administration, in particular, of anti-SAP antibodies. This strategy makes it possible to recruit the macrophages and to bring about the elimination of the amyloid deposits. However, the drawback of this strategy is that it requires a prior step of administering (R)-1-[6-[(R)-2-carboxypyrrolidin-1-yl]-6-oxohexanoyl]pyrrolidine-2-carboxylic acid (CPHPC) so as to eliminate the circulating SAP (Pepys M B et al., Nature, 2010, 468(7320): 93-7).

Moreover, NEOD001 is a monoclonal antibody in the process of being developed by Prothema, which specifically targets amyloid substances of AL or AA amyloidosis type.

This antibody reacts only with the aggregated form of the proteins responsible for this AL amyloidosis.

Other alternative therapeutic agents in the treatment of amyloidosis are being studied at the current time. In this respect, mention may be made of tafamidis which appears to make it possible to stabilize the circulating protein and to prevent deposit formation, doxycycline which could break the amyloid fibrils and prevent deposit formation (already tested on animals (Ward J. E., Blood 2011, 118(25): 6610) and in phase II in humans (Obici L. et al., Amyloid 2012: Suppl. 1: 34)) or else TUDCA, an anti-apoptosis molecule in the process of being tested.

Consequently, and for obvious reasons, the use of alternative therapeutic agents that are effective in the treatment of amyloidosis remains a constant objective with, in particular, the need to have treatments of which the objective is to slow down deposit formation or to accelerate deposit elimination, which in addition is devoid of the drawbacks mentioned above.

The objective of the present invention is precisely to meet this expectation.

SUMMARY OF THE INVENTION

According to a first of its aspects, the present invention relates to a chimeric protein comprising at least one human amyloid P component and at least one fragment of an Fc region of a human antibody, the human amyloid P component and the fragment of an Fc region to which it is attached being bonded to each other by means of a hinge region.

With the proviso of an appropriate architecture, as defined hereinafter, such a chimeric protein in fact takes advantage, on the one hand, of the natural affinity of SAP for amyloid deposits and, on the other hand, of the ability of the antibody Fc region to recruit effector cells, in particular the neutrophil polymorphonuclear cells and the monocyte-macrophages involved in the elimination of the amyloid deposits.

Thus, by virtue of the ability of the antibody Fc region to recruit effector cells, a chimeric protein according to the invention enables effective elimination of the amyloid substance deposits, thus resulting in an improvement in the clinical condition of the treated patient.

Since SAP is present in all types of amyloidosis, as previously indicated, the present invention is particularly advantageous in that it is effective whatever the type of amyloidosis considered, systemic or localized.

A chimeric protein according to the invention therefore offers an effective therapeutic alternative in the treatment of amyloidosis, with in addition the advantage of being devoid of the adverse side effects associated with the conventional treatments for amyloidosis, as mentioned above.

What is more, contrary to the strategy described in WO 2009/000926, the present invention does not require a preliminary step consisting in administering CPHPC so as to eliminate the circulating SAP.

Finally, the use of material of human origin for a chimeric protein according to the invention makes it possible to guarantee, on the one hand, maximum innocuousness with regard to the patient treated and, on the other hand, a level of interaction with the optimal targets under consideration (represented by the amyloid deposits and the effector cells).

Indeed, the use of human sequences or sequences having a strong similarity with the human sequences for a chimeric protein according to the invention makes it possible to reduce the risk of immunogenicity after administration, thus ensuring good tolerance of the administered chimeric proteins by the organism treated.

According to one particular embodiment, the human amyloid P component present in a chimeric protein according to the invention can be represented by an amino acid sequence having at least 80% identity with the sequence SEQ ID NO: 1.

According to another particular embodiment, the Fc region of the human antibody responsible for each of the Fc region fragments considered in a chimeric protein according to the invention may be an Fc region of a human immunoglobulin, preferably an Fc region of an IgG, preferably an Fc region of an IgG1 or of an IgG2, and more particularly an Fc region of an IgG1.

According to another particular embodiment, the fragment of an Fc region of a human antibody considered in a chimeric protein according to the invention may be represented by at least one amino acid sequence having at least 80% identity with the sequence SEQ ID NO: 3.

According to one particular embodiment, the fragment of an Fc region of a human antibody considered in a chimeric protein according to the invention may exhibit an improved affinity for FcRn compared with a fragment of an Fc region of a parent human antibody.

In this respect, the fragment of an Fc region of a human antibody considered in a chimeric protein according to the invention may comprise at least two modifications in the amino acid sequence as defined in WO 2010/106180, namely:

(i) a modification in the amino acid sequence chosen from the group consisting of 378V, 378T, 434Y and 434S, and (ii) at least one modification in the amino acid sequence chosen from the group consisting of 226G, 230S, 230T, 230L, 241 L, 264E, 307P, 315D, 330V, 362R, 378V, 378T, 389T, 389K, 434Y and 434S, it being understood that the numbering of the amino acids of the Fc region is that of the EU index proposed by Kabat and on the condition that the modification (i) does not occur at the same amino acid position of the modification (ii).

This embodiment is advantageous in that it contributes to further improving the ability to recruit the effector cells, in particular the neutrophil polymorphonuclear cells and the monocyte-macrophages involved, and therefore the elimination of the amyloid deposits.

Other particular embodiments, described hereinafter, make it possible in particular to further improve the ability to recruit effector cells, more particularly via improved bonding between the Fc region fragments considered and the Fcgamma R receptors, in particular Fcgamma RIII or CD16, expressed in particular at the surface of polymorphonuclear cells and macrophages.

Thus, according to another particular embodiment, a fragment of an Fc region of a human antibody considered in a chimeric protein according to the invention may exhibit a low degree of fucosylation at the level of the oligosaccharide chains borne by Asn297 (Kabat numbering), characterized by a fucose content of less than 65% relative to the total content of the glycan structures at the level of the oligosaccharide chains borne by Asn297.

In another embodiment, a fragment of an Fc region of a human antibody considered in a chimeric protein according to the invention may exhibit a low degree of fucosylation, characterized by glycan structures having a content of less than 50% of G0F+G1F forms described hereinafter, relative to the total content of the glycan structures. For example, a fragment of an Fc region of a human antibody considered in a chimeric protein according to the invention may also comprise a content of greater than 60% for the G0+G1+G0F+G1F forms, the G0F+G1F forms being less than 50%.

In another particular embodiment, the antibodies may comprise a content of greater than 60% for the G0+G1+G0F+G1F forms, the fucose content being less than 65%.

These G0, G0F, G1 and G1F forms are more particularly illustrated in FIG. 8 hereinafter.

According to the final embodiment described above, the fragment of an Fc region of a human antibody considered in a chimeric protein according to the invention may also comprise, on an Asn297 glycosylation site, a glycan structure having end mannoses and/or end N-acetylglucosamines which are non-intercalated.

The fragment of an Fc region of a human antibody considered in a chimeric protein according to the invention may comprise, on the Asn297 glycosylation site, a glycan structure of biantennary type, with short chains, a low degree of sialylation, and a content of greater than 60% for the G0+G1+G0F+G1F forms, the G0F+G1F forms being less than 50%. For example, the fragment of an Fc region of a human antibody considered in a chimeric protein according to the invention can have a sialic acid content of less than 25%, 20%, 15% or 10%, preferably 5%, 4%, 3% or 2%.

The fragment of an Fc region of a human antibody considered in a chimeric protein according to the invention may comprise a content of greater than 60%, preferably greater than 80% for the G0+G1+G0F+G1F forms, it being understood that the G0F+G1F forms are less than 50%, preferably less than 30%.

The fragment of an Fc region of a human antibody considered in a chimeric protein according to the invention may comprise glycan structures of biantennary type, with short chains, a low degree of sialylation, non-intercalated end attachment point mannoses and N-acetylglucosamines, the glycan structures having a content of greater than 60% for the G0+G1+G0F+G1F forms, and a low degree of fucosylation, the glycan structures having a content of less than 50% of G0F+G1F forms.

Some of the particular embodiments described above are in particular described in greater detail in WO 01/77181 and WO 2012/175874.

As indicated above, a chimeric protein according to the invention comprises a hinge region between the human amyloid P component and the fragment of an Fc region of a human antibody to which said human amyloid P component is attached.

This construction has the advantage of ensuring greater accessibility both to the human amyloid P component and to the fragment of an Fc region of a human antibody and also confers greater flexibility on a chimeric protein according to the invention. This embodiment is advantageous in that it therefore contributes to improving the ability of the human SAP to recognize the amyloid deposits and the ability of the Fc region fragments to recruit effector cells, in particular the neutrophil polymorphonuclear cells and the monocyte-macrophages involved, and therefore the elimination of the amyloid deposits.

With the proviso of an appropriate architecture, as defined hereinafter, the combining of two fragments of an Fc region of a human antibody as encountered in the immunoglobulins confers, on a chimeric protein according to the invention, an ability to interact with Fc receptors that is comparable to that of immunoglobulins. This combining therefore results in a functional region capable of recruiting effector cells and of ensuring the elimination of amyloid plaques.

The nature of the hinge region falls within the knowledge of those skilled in the art.

More particularly, a hinge region according to the invention may be a specific peptide sequence comprising at least one cysteine residue or one non-peptide molecule such as polyethylene glycol (PEG).

Preferably, a hinge region in accordance with the invention can be chosen from the hinge regions of human IgG1, human IgG2, human IgG3 or human IgG4.

Even more preferentially, a hinge region can comprise at least one amino acid sequence having at least 60% identity, preferably at least 80% identity, with a sequence chosen from the sequences SEQ ID NOs: 13 and 15 to 18, in particular the sequence SEQ ID NO: 13.

A hinge region according to the invention may also be represented by variants of the sequences SEQ ID NOs: 13 and 15 to 18.

By way of illustration of variants of a hinge region comprising at least one amino acid sequence having at least 60% identity, preferably at least 80% identity, with the sequences SEQ ID NOs: 13 and 15 to 18, mention may be made of the sequence SEQ ID NO: 13 in which the first cysteine is mutated by a serine.

According to one particularly preferred embodiment, a hinge region according to the invention may be represented by the amino acid sequence SEQ ID NO: 19.

According to one particular embodiment, a hinge region according to the invention may also include a non-structuring peptide sequence between the hinge region and the amyloid P component.

In particular, such a non-structuring peptide sequence may be represented by an amino acid sequence SEQ ID NO: 5.

This sequence SEQ ID NO: 5, having the unit (GGGGS)n (or $G_4S$)n, is therefore more or less long depending on the desired flexibility. In this regard, "n" is preferably between 1 and 5, and preferably is equal to 3.

As previously indicated, the ability of a chimeric protein according to the invention to exhibit a natural affinity of human SAP for amyloid deposits, but especially to recruit effector cells, in particular the neutrophil polymorphonuclear cells and the monocyte-macrophages involved in the elimination of the amyloid deposits via the fragment of an Fc region of a human antibody, is conditioned by an appropriate architecture, as defined hereinafter.

Thus, according to a first implementation variant, the chimeric protein according to the invention may comprise at least two units, each unit comprising at least one human amyloid P component and at least one fragment of an Fc region of a human antibody, bonded to each other by means of a hinge region, the two units being bonded to each other covalently by at least one disulfide bridge.

This specific architecture is in particular denoted in the remainder of the present application by the expression "dimeric SAP-Fc" and is illustrated in FIG. 1.

This first implementation variant results in the formation of a dimeric chimeric protein. This specific architecture is advantageous in that it improves the ability to recruit effector cells, in particular the neutrophil polymorphonuclear cells and the monocyte-macrophages involved, and therefore the elimination of the amyloid deposits.

For each unit, said human amyloid P component and said fragment of an Fc region of a human antibody are bonded to each other by a hinge region, as previously defined.

According to this implementation variant, the fragments of an Fc region of a human antibody of the various units considered may be identical or different.

Alternatively, a dimeric SAP-Fc chimeric protein according to the invention may comprise at least two units, each unit comprising at least one human amyloid P component and at least one fragment of an Fc region of a human antibody, bonded to each other by means of a hinge region, but the two units being bonded to each other by a bond formed from at least two poly(ethylene glycol) (PEG) groups.

Since a chimeric protein of dimeric SAP-Fc type results from the bonding of two units as defined above, each unit being bonded to each other by at least one disulfide bridge or by a bond formed from at least two PEG groups, the present invention also relates to a chimeric protein represented by a single unit by way of intermediate compound.

Thus, the present invention also relates, by way of intermediate compound, to a chimeric protein comprising a single human amyloid P component and a single fragment of an Fc region of a human antibody, the human amyloid P component and the fragment of an Fc region being bonded to each other by means of a hinge region.

Such an intermediate compound may also be denoted in the remainder of the present description by the expression "monomeric SAP-Fc".

Such an intermediate compound can be represented by an amino acid sequence having at least 80%, preferably at least 90%, identity with the sequence SEQ ID NO: 7.

A protocol for preparing a dimeric SAP-Fc chimeric protein as previously defined starting from a "monomeric SAP-Fc" intermediate chimeric protein falls within the general knowledge of those skilled in the art.

Such an aspect is in particular subsequently described in the examples.

According to another implementation variant, the chimeric protein according to the invention may comprise at least one human amyloid P component and at least two fragments of an Fc region of a human antibody (i.e. first and second fragments of an Fc region of a human antibody), which may be identical or different, said human amyloid P component and said first fragment of an Fc region of a human antibody being bonded to each other by means of a hinge region, the first and second fragments of an Fc region being bonded to each other covalently by means of a bond formed from a spacer chain and a hinge region identical to or different than that previously mentioned, and form a single polypeptide chain constituting a functional dimeric Fc region.

This specific architecture is in particular denoted in the remainder of the present application by the expression "monomeric SAP-ScFc" and is illustrated in FIG. 2.

In other words, a monomeric SAP-ScFc protein according to the invention comprises, from the N-terminal part to the C-terminal part, (1) a human amyloid P compound, (2) a hinge region, (3) a first fragment of an Fc region of a human antibody, (4) a spacer chain, (5) a hinge region, identical to or different than that considered in (2) above, and (6) a second fragment of an Fc region of a human antibody, identical to or different than that considered in (3) above.

Proteins which have this particular architecture, which can be called "single chain Fc" or "ScFc", comprising at least two fragments of an Fc region of a human antibody, which are identical or different, and being bonded to each other covalently so as to form a single polypeptide chain constituting a functional dimeric Fc region, are in particular described in WO 2008/143954.

In this regard, the spacer chain considered in the bonding between the first and second fragments of an Fc region can preferably be represented by an amino acid sequence SEQ ID NO: 5.

In this respect, this sequence SEQ ID NO: 5, having the unit (GGGGS)n (or G4S)n, is therefore more or less long depending on the desired flexibility. In this regard, "n" is preferably between 1 and 5, and preferably equal to 3.

Moreover, the human amyloid P component and the first fragment of an Fc region of a human antibody to which said human amyloid P component is attached are separated from each other by means of a hinge region as previously defined.

According to yet another implementation variant, a chimeric protein according to the invention can result from the natural pairing of two monomeric SAP-ScFc chimeric proteins, bonded to each other by means of at least two disulfide bridges or of at least two bonds, a bond being formed from at least two poly(ethylene glycol) (PEG) groups.

This specific architecture is in particular denoted in the remainder of the present application by the expression "dimeric SAP-ScFc" and is illustrated in FIG. 3.

These three implementation variants dimeric SAP-Fc, monomeric SAP-ScFc and dimeric SAP-ScFc of a chimeric protein according to the invention all comprise at least two Fc region fragments, which therefore results in a functional region responsible for the ability of these particular architectures to recruit effector cells and thus to ensure the elimination of the amyloid plaques.

Moreover, the monomeric SAP-Fc and monomeric SAP-ScFc chimeric proteins according to the invention and as previously described can pair together to form a pentameric structure, or else a decametric structure (i.e. resulting from two pentameric structures interacting face-to-face). Indeed, it has been shown that the serum SAP protein can combine with itself to form pentameric and dimeric structures (Hutchinson et al., 2000, Molecular Medicine, 6:482).

According to another of its aspects, the present invention relates to a nucleic acid comprising at least one polynucleotide sequence encoding at least one chimeric protein according to the invention.

Since the formation of the dimeric SAP-Fc and dimeric SAP-ScFc structures results from a natural pairing phenomenon, the polynucleotide sequence preferably encodes at least the monomeric SAP-Fc or monomeric SAP-ScFc chimeric protein.

According to yet another of its aspects, the present invention relates to a vector into which a nucleic acid as defined above is inserted.

According to another of its aspects, the present invention relates to a host cell transfected with a vector as previously defined.

According to yet another of its aspects, the present invention relates to a process for producing a chimeric protein as previously defined, said process comprising at least the steps consisting in:

a) transfecting a host cell with a vector as defined above;
b) culturing said host cell under conditions such that the chimeric protein is produced; and
c) collecting said chimeric protein produced by said host cell at the end of step b).

Considering the dimeric SAP-Fc chimeric protein, it should be noted that the step consisting in covalently bonding, by means of at least one disulfide bridge, the two units each comprising at least one human amyloid P component and at least one fragment of an Fc region of a human antibody with, for each unit, said human amyloid P component being bonded to said fragment of an Fc region to which it is attached by means of a hinge region, is a step which occurs naturally in the host cell.

In the same way, the pairing of two monomeric SAP-ScFc proteins for obtaining the dimeric SAP-ScFc chimeric protein takes place naturally in the host cell, by the formation of at least two disulfide bridges.

According to yet another of its aspects, the present invention relates to a pharmaceutical composition comprising a chimeric protein according to the invention and a pharmaceutically acceptable excipient.

According to yet another of its aspects, the present invention relates to a chimeric protein as defined above, for use thereof as a medicament.

According to yet another of its aspects, the present invention relates to a chimeric protein as defined above, for use thereof for eliminating the amyloidosis deposits in the organs.

According to yet another of its aspects, the present invention relates to a chimeric protein as defined above, for inducing an activation of the phagocytosis of the ligand recognized by the human amyloid P component by the neutrophil polymorphonuclear cells and/or the monocyte-macrophages.

According to yet another of its aspects, the present invention relates to a chimeric protein as defined above, for use thereof for treating amyloidosis, in particular amyloidosis of AL type.

According to yet another of its aspects, the present invention relates to a process for treating amyloidosis, in particular amyloidosis of AL type, comprising at least one step of administering, to an individual in need thereof, an effective amount of at least one first active agent represented by a chimeric protein or a composition as previously defined.

According to one particular embodiment, said process may also comprise a step of administering, prior to, concomitant with and/or subsequent to the step of administering the first active agent, at least one second active agent distinct from said first active agent, the second active agent preferably being chosen from the group comprising 4-[bis(chloroethyl)amino]phenylalanine (melphalan); 9-fluoro-11β,17,21-trihydroxy-16a-methylpregna-1,4-diene-3,20-dione (dexamethasone); prednisone; dimethyl sulfoxide (DMSO); N-[(7S)-5,6,7,9-tetrahydro-1,2,3,10-tetramethoxy-9-oxobenzo[a]heptalen-7-yl)acetamide] (colchicine); (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione (doxorubicin); active agents capable of reacting with the amyloid P component, in particular of bis-d-proline type, and more particularly the compound (R)-1-[6-[(R)-2-carboxypyrrolidin-1-yl]-6-oxohexanoyl]pyrrolidine-2-carboxylic acid); proteasome inhibitors, for example bortezomib, carfilzomib, marizomib, ixazomib, delanzomib, ONX-912 or revlimid; and a mixture thereof.

According to yet another of its aspects, the present invention relates to the use of at least one chimeric protein as defined above, as a tool for in vitro or ex vivo characterization of the presence of an amyloidosis deposit.

According to yet another of its aspects, the present invention relates to the use of at least one chimeric protein as defined above, as a tool for in vitro or ex vivo characterization of the presence of an amyloidosis deposit.

According to a first implementation variant, the chimeric protein is radiolabeled; preferably, the human amyloid P component is represented by $^{123}$I-SAP.

According to a second implementation variant, the chimeric protein is identified by means of a radiolabeled anti-Fc antibody; for example, said anti-Fc antibody is coupled to peroxidase.

A chimeric protein according to the invention may also be identified by means of any technique known to those skilled in the art. In this respect, mention may in particular be made of the technique via coupling with fluorophores and microbeads, as described in Neri et al. (1997) Nat Biotech, or else the techniques described in Brack et al. (2005) EJNM, Santimaria (2003) Clinical cancer res, Borsi et al. (2002) Int J cancer, Berndorff (2006) J Nucl Med and Joseph et al. (2004) Pharm Res.

DESCRIPTION OF THE FIGURES

In FIGS. 6A and 6B, the peaks located between 0 and 60 ml correspond to the exclusion volume. In FIGS. 6A and 6B, the peaks located between 60 and 70 ml correspond to the chimeric proteins according to the invention.

FIG. 10 illustrates more particularly the amount of amyloidosis deposits observed in Balb/c mice having received injections of PBS, of IgIR irrelevant IgG1 proteins (control) or of SAP-Fc or SAP-ScFc chimeric proteins according to the invention. These results are obtained from the spleens of said mice.

FIG. 11 illustrates more particularly the amount of amyloidosis deposits observed in VH-LMP2A mice having received injections of PBS, of SAP proteins as such (i.e. devoid of the fragment of an Fc region of a human antibody) and of SAP-ScFc chimeric proteins according to the invention. These results are obtained from the spleens of said mice.

DETAILED DESCRIPTION OF THE INVENTION

Figure 1:
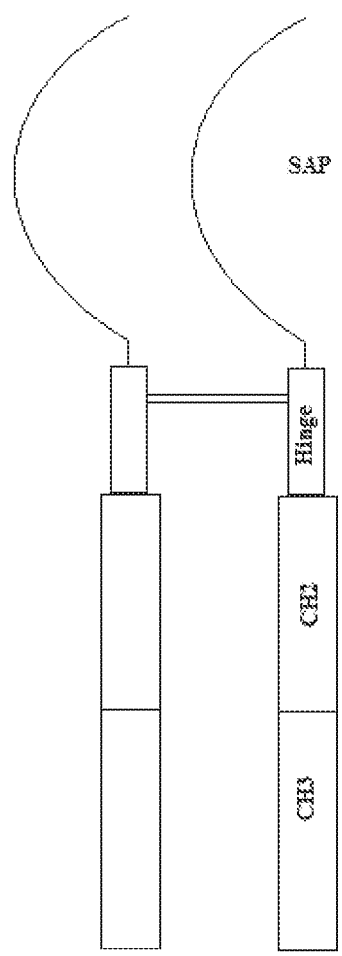
FIG. 1 illustrates a chimeric protein according to the invention comprising two units each comprising a human amyloid P component and a fragment of an Fc region of a human antibody, bonded to each other by a hinge region, the two units being bonded to each other covalently by a disulfide bridge (=dimeric SAP-Fc chimeric protein).

As indicated above and illustrated in the examples hereinafter, the inventors have shown that a chimeric protein, by taking advantage of, on the one hand, the natural affinity of SAP for amyloid deposits and, on the other hand, the ability of the Fc region of antibodies to recruit effector cells, in particular neutrophil polymorphonuclear cells and monocyte-macrophages, is particularly advantageous in terms of eliminating the amyloid deposits, this being whatever the type of amyloidosis considered.

Definitions

Preliminarily, in order for it to be possible to understand the application more clearly, several definitions are stated below. These definitions are supposed to encompass the grammatical equivalents.

For the purposes of the present invention, the term "chimeric protein" is intended to denote a protein consisting of a first amino acid sequence derived from a first source, covalently bonded to a second amino acid sequence derived from a second source, in which the first and second source are not identical or, in other words, characterize two different biological entities. In the case in point, one among the first or second amino acid sequence represents at least one human amyloid P component and the other represents at least one fragment of an Fc region of a human antibody. In the context of the present invention, the first and second amino acid sequences are bonded to each other by means of a hinge region, in particular as previously defined.

In the context of the present invention, a chimeric protein is also intended to denote dimeric forms of a protein as defined above, or of a derivative thereof.

The term "polynucleotide" is intended to mean, according to the invention, a compound comprising a nucleotide polymer, which encompasses a ribonucleotide (RNA) polymer and a deoxyribonucleotide (DNA) polymer, said nucleotides being optionally chemically modified. According to the invention, a polynucleotide can advantageously have a length ranging from 5 to 3000 nucleotides. A polynucleotide conventionally encompasses polyribonucleotides and the polydeoxyribonucleotides, where appropriate chemically modified. In certain embodiments, a polynucleotide consists of a polymer of nucleotides, ribonucleotides or deoxyribonucleotides. In other embodiments, a nucleic acid consists essentially of a nucleotide polymer and comprises a non-nucleotide part, said non-nucleotide part preferentially being of reduced length, compared with the length of the nucleotide part, for example a linear length less than the length occupied by a chain of five nucleotides, ribonucleotides or deoxyribonucleotides. Preferentially, the non-nucleotide part is not polypeptide in nature, or alternatively does not contain an amino acid residue. A polynucleotide can comprise one or more modified nucleotides, such as methylated nucleotides, it being possible for the modifications to be carried out before, during or after assembly of the nucleotide polymer. In certain embodiments, the non-nucleotide part can consist of a spacer chain comprising a free carboxyl group or of a spacer chain comprising a free amine group.

For the purposes of the present description, the terms "polynucleotide entity" and "polynucleotide" are used without implied distinction to denote the same subject.

According to the invention, the term "polypeptide" is intended to mean a chain of at least two amino acid residues, which encompasses a change ranging from 2 to 1000 amino acid residues in length, said amino acid residues being bonded to each other by covalent bonds, including by peptide bonds. In the present description, the term "polypeptide" can be used to denote without implied distinction a protein, a peptide or an oligopeptide. The term "polypeptide" encompasses polypeptides chemically modified by one or more functional groups or by one or more non-peptide molecules, with the exception of a modification by a polynucleotide.

For the purposes of the present description, the terms "polypeptide entity" and "polypeptide" are used without implied distinction to denote the same subject.

The term "amino acid" encompasses any one of the 22 natural amino acid residues, and the non-natural analogs thereof. The amino acids encompass the residues alanine (Ala; A), arginine (Arg; R), asparagine (Asp; N), aspartic acid (Asp; D), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), valine (Val; V), pyrrolysine and selenocysteine. The amino acids encompass the L-amino acids and the D-amino acids. Preferentially, the amino acids are the L-amino acids.

For the purposes of the present invention, the term "amyloid P component" or "SAP protein" is intended to denote a glycoprotein, belonging to the family of pentraxin proteins, which has a characteristic pentameric organization. It is a glycoprotein constituting all the amyloid deposits, in particular those isolated from the pancreas of long-term diabetics. It is made up of 10 identical glycosylated polypeptide subunits, noncovalently linked to form two pentamers arranged in two helical filaments. Each subunit of the pentagonal structure obtained has a molecular weight of 23 to 25 000 Daltons. SAP is part of the family of pentraxins such as CRP (c-reactive protein) with which it exhibits a structural homology, the N-terminal parts being homologous. SAP is naturally present in the blood in an amount of approximately 20 to 30 mg/l of blood (Pepys, M. B., et al., Ann Rev Med, 2006; 57:223-41.)

The term "Fc" or "Fc region", as used here, is intended to mean the crystallizable fragment generated during the enzymatic digestion of immunoglobulins by papain. The Fc fragment refers to the last two constant regions of IgA, IgD and IgG immunoglobulins, and to the last three constant regions of IgE and IgM. For IgA and IgM, Fc may comprise the J chain. For IgG, Fc comprises the Cgamma2 and Cgamma3 immunoglobulin domains (Cγ2 and Cγ3 which are the CH2 and CH3 domains, respectively). The heavy chain of the Fc region of human IgG1 is defined here as comprising C226 residues at its carboxyl end, where the numbering of the amino acids of the Fc region is that of the EU index proposed by Kabat. In the context of human IgG1, the CH2 domain refers to positions 237 to 340 and the CH3 domain refers to positions 341 to 447 according to the EU index proposed by Kabat.

The term "antibody" is used here in the broadest sense. The term "antibody" is therefore intended to denote any polypeptide which comprises at least: (i) one Fc region and (ii) one polypeptide binding domain derived from a variable region of an immunoglobulin. Said polypeptide binding domain is capable of binding specifically to a given target antigen or a group of target antigens. A polypeptide binding domain which derives from a variable region of an immunoglobulin comprises one or more CDRs ("complementarity determining regions"). The antibodies comprise, but are not limited to, full-length immunoglobulins, monoclonal antibodies, multispecific antibodies, Fc fusion proteins comprising at least one variable region, synthetic antibodies (sometimes referred to as "mimetic antibodies"), chimeric antibodies, humanized antibodies, whole human antibodies, fusion protein-antibodies, antibody conjugates, and respective fragments thereof.

The term "full-length antibody" or "immunoglobulin" as used here is intended to mean the structure which constitutes the natural biological form of an antibody, comprising the variable and constant regions. The "full-length antibodies" cover monoclonal full-length antibodies, wild-type full-length antibodies, chimeric full-length antibodies, humanized full-length antibodies, the list not being limiting.

In most mammals, including humans and mice, the structure of full-length antibodies is generally a tetramer. Said tetramer is composed of two identical pairs of polypeptide chains, each pair having a "heavy" chain (typically having a molecular weight of approximately 50-70 kDa) and a "light" chain (typically having a molecular weight of approximately 25 kDa). In some mammals, for example in camels and lamas, the full-length antibodies may consist of only two heavy chains, each heavy chain comprising a variable domain attached to the Fc region.

The amino-terminal part of each chain comprises a variable region of approximately 100 to 110 amino acids which is responsible for antigen recognition. In the variable region, three loops are assembled for each of the V domains of the heavy chain and of the light chain so as to form an antigen-binding site. Each of these loops relates to a CDR, in which the variation of the amino acid sequence is greatest.

The carboxy-terminal part of each chain defines a constant region principally responsible for the effector function. Kabat et al. has collected numerous variable-region primary sequences of heavy chains and of light chains. On the basis of the degree of sequence conservation, they have classified the individual primary sequences into the CDRs and have made a list thereof (see Sequences of Immunological Interest, 5th edition, NIH Publication, No. 91-3242, EA Kabat et al., incorporated herein by way of reference in its entirety).

In the case of human immunoglobulins, the light chains are classified as kappa and lambda light chains. The heavy chains are classified as mu, delta, gamma, alpha, or epsilon, and define the isotype of the antibody, such as IgM, IgD, IgG, IgA and IgE, respectively. IgG has several subclasses, including, but without being limited thereto, IgG1, IgG2, IgG3 and IgG4. IgM has several subclasses, including, but without being limited thereto, IgM1 and IgM2. Thus, the term "isotype" as used herein is intended to mean one of the immunoglobulin subclasses defined by the chemical and antigenic characteristics and the characteristics of their constant regions. The known human immunoglobulin isotypes are IgG1, IgG2, IgG3, IgG4, IgA1, IgA2, IgM1, IgM2, IgD and IgE.

The term "IgG" as used herein is intended to mean a polypeptide belonging to the antibody class which is substantially encoded by a recognized immunoglobulin gamma gene. In humans, IgG comprises the subclasses or isotypes IgG1, IgG2, IgG3 and IgG4.

The full-length IgGs are tetramers and are composed of two identical pairs of two immunoglobulin chains, each pair having a light chain and a heavy chain, each light chain comprising the VL and CL domains, and each heavy chain comprising the VH, Cγ1 (also called CH1), Cγ2 (also called CH2) and Cγ3 (also called CH3) domains. In the context of human IgG1, "CH1" refers to positions 118 to 220, the CH2 domain refers to positions 237 to 340 and the CH3 domain refers to positions 341 to 447 according to the EU index proposed by Kabat. The IgG heavy chain also comprises a hinge region ("hinge domain") which refers to positions 221 to 236 in the case of IgG1.

For the purposes of the present invention, the term "fragments" of an Fc region is intended to denote identical or different polypeptides which comprise one or more polypeptides derived from a wild-type Fc region, preferably from the CH2-CH3 domain which is under the hinge region of a wild-type IgG. The fragments of an Fc region according to the invention are such that, when they are in dimeric form such as those previously described (i.e. within the dimeric SAP-Fc, monomeric SAP-ScFc and dimeric SAP-ScFc chimeric proteins), they retain their ability to recruit effector cells, in particular neutrophil polymorphonuclear cells and monocyte-macrophages. To this effect, the fragments of an Fc region according to the invention have a dissociation constant for FcRn of less than 1 microM according to SPR assay.

For the purposes of the present invention, the term "FcRn" or "neonatal Fc receptor" is intended to denote a protein which binds to the Fc region of IgG antibodies and is at least partly encoded by an FCRN gene. The FcRn may be from any organism, including, but not limited to, humans, mice, rats, rabbits and monkeys. In the light of the therapeutic indications considered in the present application, the FcRn is human FcRn. As is known in the art, the functional FcRn protein comprises two polypeptides, often denoted as the heavy chain and the light chain. The light chain is beta-2-microglobulin and the heavy chain is encoded by the RRFC gene. Unless otherwise indicated, FcRn or the FcRn protein refers to the complex of the α-chain with beta-2-microglobulin. In humans, the gene encoding FcRn is called FCGRT.

As indicated above, according to one particular embodiment, the Fc region or the fragment of an Fc region of a human antibody of a chimeric protein according to the invention may exhibit an improved affinity for FcRn compared with the Fc region of a fragment of an Fc region of a parent human antibody.

The term "parent" as used herein is intended to mean a nonmodified polypeptide which is subsequently modified to produce a variant. Said parent polypeptide may be a naturally existing polypeptide, a variant of a natural polypeptide, the engineered version or a synthetic polypeptide. The parent polypeptide may refer to the polypeptide itself, or to the amino acid sequence which encodes it. In the context of the present invention, the parent polypeptide is a human antibody which comprises an Fc region. The parent polypeptide may optionally comprise preexisting amino acid modifications in its Fc region (for example an Fc mutant) compared with wild-type Fc regions.

The term "improved affinity for FcRn" as used herein is intended to mean an increase in the binding affinity, in vivo or in vitro, of a fragment of an Fc region for FcRn compared with a fragment of an Fc region derived from a parent human antibody.

The affinity for FcRn, of a fragment of an Fc region of a human antibody according to the invention, can be evaluated by well-known prior art methods. For example, those skilled in the art can determine the dissociation constant (Kd) using surface plasmon resonance (SPR), as described for example in Yeung Y A, et al. (2009, J. Immunol, vol. 182: 7663-7671). In the case of a fragment of an Fc region of a human antibody according to the invention comprising certain modifications in its amino acid sequence compared with a fragment of an Fc region of a parent human antibody, for the purposes of improving its affinity for FcRn, the presence of a Kd value 1.5 to 3 times lower (higher affinity) than that of the fragment of an Fc region of a parent human antibody confirms this improvement.

As an alternative technique, those skilled in the art can perform an appropriate ELISA assay, as described for example by Deng et al. (2012, Landes Bioscience, vol. 4(1): 101-109). An appropriate ELISA assay makes it possible to compare the strength of binding between a fragment of an Fc region of a human antibody according to the invention comprising certain modifications and a fragment of an Fc region of a parent human antibody. A fragment of an Fc region of a human antibody according to the invention comprising certain modifications thus exhibits an improved affinity for FcRn if its specific signal is at least 1.2 times stronger, preferably at least 4 times stronger, than that measured with a fragment of an Fc region of a parent human antibody.

For the purposes of improving the affinity for FcRn, the Fc region of the antibody of the chimeric protein according to the invention can comprise certain modifications in its amino acid sequence.

For the purposes of the present invention, the term "modifications in the amino acid sequence" is intended to denote a change in the amino acid sequence of a polypeptide. A modification in the amino acid sequence, or changing of amino acids, comprises a substitution, an insertion and/or a deletion of an amino acid included in a polypeptide sequence.

The term "substitution of an amino acid" or "substitution" is intended to mean herein the replacement of an amino acid in a particular position in a parent polypeptide sequence with another amino acid. For example, the substitution N434S refers to a polypeptide in which the asparagine in position 434 is replaced with serine.

The term "insertion of an amino acid" or "insertion" is intended to mean herein the addition of an amino acid at a particular position in a parent polypeptide sequence. For example, insert G>235-236 denotes an insertion of glycine between positions 235 and 236.

The term "deletion of an amino acid" or "deletion", as used herein, is intended to mean the deletion of an amino acid at a particular position in a parent polypeptide sequence. For example, E294del denotes the deletion of glutamic acid in position 294.

For example, the following modification form is preferentially used: 434S, or N434S, means that the parent amino acid in position 434, i.e. asparagine, is replaced with serine. In the case of a combination of substitutions, the preferred format is the following: 259I/315D/434Y or V259I/N315D/N434Y. This means that there are three substitutions, one in position 259, one in position 315 and one in position 434, and that the amino acid in position 259 of the parent polypeptide, i.e. the valine, is replaced with isoleucine, that the amino acid in position 315 of the parent polypeptide, i.e. the asparagine, is replaced with aspartic acid and that the amino acid in position 434 of the parent polypeptide, i.e. the asparagine, is replaced with tyrosine.

Chimeric Protein According to the Invention

As previously indicated, according to a first of its aspects, the present invention relates to a chimeric protein comprising at least one human amyloid P component and at least one fragment of an Fc region of a human antibody, the human amyloid P component and the fragment of an Fc region to which it is attached being bonded to each other by means of a hinge region.

According to one particular embodiment, the human amyloid P component present in a chimeric protein according to the invention can be represented by an amino acid sequence having at least 80% identity with the sequence SEQ ID NO: 1, preferably at least 90% identity with the sequence SEQ ID NO: 1.

For the purposes of the present invention, an amino acid sequence having at least 80% identity with a reference sequence has an identity of at least 80%, 81%, 82%, 83%, 84%, 85%, 86%, 87%, 88%, 89%, 90%, 91%, 92%, 93%, 94%, 95%, 96%, 97%, 98%, 99% or 99.5% with said reference sequence.

For determining the percentage identity of two amino acid sequences, sequence alignment methods are well known to those skilled in the art. The sequences are aligned for the purposes of optical comparison. For example, gaps can be introduced into one of or both the first and second amino acid or nucleotide sequences for optimal alignment and the non-homologous sequences can be discarded for the purposes of comparison. By way of example and without being limiting, the percentage identity of two amino acid or nucleotide sequences can be carried out with CLUSTAL W (version 1.82, version 2), CLUSTAL OMEGA, BLAST or MULTALIN.

According to another particular embodiment, the human amyloid P component present in a chimeric protein according to the invention can be represented by an amino acid sequence encoded by a nucleic acid sequence having at least 80% identity with the sequence SEQ ID NO: 2, preferably at least 90% identity with the sequence SEQ ID NO: 2.

Thus, for the purposes of the present invention, a nucleic acid sequence having at least 80% identity with a reference sequence has an identity of at least 80%, 81%, 82%, 83%, 84%, 85%, 86%, 87%, 88%, 89%, 90%, 91%, 92%, 93%, 94%, 95%, 96%, 97%, 98%, 99% or 99.5% with said reference sequence.

According to another particular embodiment, the Fc region responsible for each of the fragments of an Fc region of a human antibody of the chimeric protein according to the invention may be an Fc region of a human immunoglobulin, preferably an Fc region of an IgG, better still an Fc region of an IgG1 or of an IgG2, and more particularly an Fc region of an IgG1.

According to another particular embodiment, the fragment of an Fc region of a human antibody of a chimeric protein according to the invention can be represented by at least one amino acid sequence having at least 80% identity with the sequence SEQ ID NO: 3.

According to yet another particular embodiment, the fragment of an Fc region of a human antibody of a chimeric protein according to the invention can be represented by at least one amino acid sequence encoded by a nucleic acid sequence having at least 80% identity with the sequence SEQ ID NO: 4.

According to one particular embodiment, the fragment of an Fc region of a human antibody of a chimeric protein according to the invention can exhibit an improved affinity for FcRn, compared to a fragment of an Fc region of a parent human antibody.

In this respect, the Fc region of the antibody of the chimeric protein according to the invention can comprise at least two modifications in the amino acid sequence, namely:

(i) a modification in the amino acid sequence chosen from the group consisting of 378V, 378T, 434Y and 434S, and (ii) at least one modification in the amino acid sequence chosen from the group consisting of 226G, 230S, 230T, 230L, 241 L, 264E, 307P, 315D, 330V, 362R, 378V, 378T, 389T, 389K, 434Y and 434S, it being understood that the numbering of the amino acids of the Fc region is that of the EU index proposed by Kabat and on the condition that the modification (i) does not occur at the same amino acid position as the modification (ii).

This embodiment is advantageous in that the combination of various mutations contributes to also improving the ability to recruit effector cells, in particular the neutrophil polymorphonuclear cells and the monocyte-macrophages involved, and therefore the elimination of the amyloid deposits.

As previously denoted, a human amyloid P component is attached to the fragment of an Fc region of a human antibody by means of a hinge region.

This construction has the advantage of ensuring greater accessibility both to the amyloid P component and to the fragment of an Fc region of an antibody and also confers greater flexibility on a chimeric protein according to the invention. This embodiment is advantageous in that it contributes to improving the ability of the SAP to recognize the amyloid deposits and the recruitment of effector cells, in particular the neutrophil polymorphonuclear cells and the monocyte-macrophages involved, and therefore the elimination of the amyloid deposits.

The nature of the hinge region can be chosen according to the knowledge of those skilled in the art. Preferably, the hinge region is a specific peptide sequence comprising at least one cysteine residue or one non-peptide molecule such as polyethylene glycol (PEG).

Preferably, a hinge region in accordance with the invention can be chosen from the hinge regions of human IgG1, human IgG2, human IgG3 or human IgG4.

Advantageously, a hinge region according to the invention is that of human IgG1.

In this regard, a hinge region according to the invention may comprise at least one amino acid sequence having at least 60% identity, preferably at least 80% identity, with a sequence chosen from the sequences SEQ ID NOs: 13 and 15 to 18, preferably with the sequence SEQ ID NO: 13.

A hinge region in accordance with the invention can, for example, be represented by the sequence SEQ ID NO: 19.

According to one particular embodiment, a non-structuring peptide sequence can also be present between the hinge region and the amyloid P component.

In particular, such a non-structuring peptide sequence can be represented by the sequence SEQ ID NO: 5.

This sequence, having the (G4S)n unit, is therefore more or less long depending on the desired flexibility. In this regard, "n" is preferably between 1 and 5.

According to a first implementation variant, the chimeric protein according to the invention may comprise at least two units, each unit comprising at least one human amyloid P component and at least one fragment of an Fc region of a human antibody, bonded to each other by means of a hinge region, the two units being bonded to each other covalently by at least one disulfide bridge.

This first implementation variant, characterizing the dimeric SAP-Fc architecture, is in particular illustrated in FIG. 1 hereinafter.

This first implementation variant results in the formation of a dimeric chimeric protein. This specific architecture is advantageous in that it results in effective recruitment of effector cells, in particular the neutrophil polymorphonuclear cells and the monocyte-macrophages involved. As a result, this dimeric chimeric protein could be particularly effective in eliminating amyloid deposits.

In the light of the aforementioned, a chimeric protein according to this first implementation variant can therefore comprise at least two amino acid sequences, it being possible for each sequence, which may be identical or different, to be represented by an amino acid sequence having at least 80% identity, preferably at least 90%, with the sequence SEQ ID NO: 7, each of the sequences being bonded to each other covalently by at least one disulfide bridge.

According to a second implementation variant, the chimeric protein according to the invention may comprise at least one human amyloid P component and at least two fragments of an Fc region of a human antibody (i.e. first and second fragments of an Fc region of a human antibody), with a hinge region between said human amyloid P component and the first fragment of an Fc region of a human antibody to which it is attached, the two fragments of an Fc region, which may be identical or different, being bonded to each other covalently by means of a bond formed from a spacer chain and a hinge region, identical to or different than that mentioned above, and form a single polypeptide chain constituting a functional dimeric Fc region.

Figure 2:
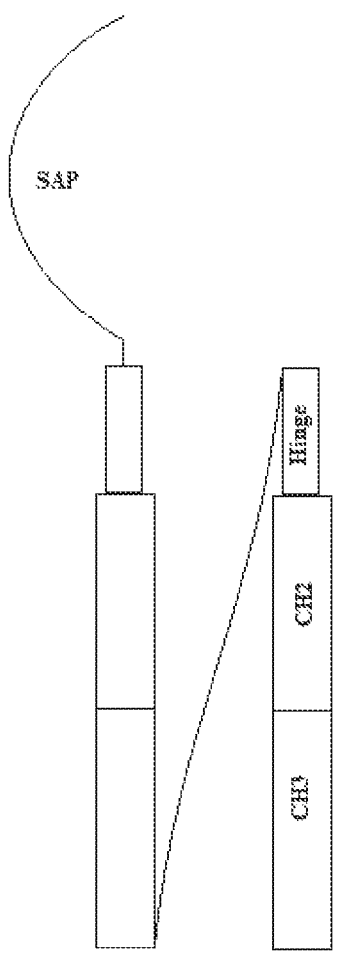
FIG. 2 illustrates a chimeric protein according to the invention comprising a human amyloid P component and two fragments of an Fc region of a human antibody (i.e. first and second fragments of an Fc region of a human antibody), the human amyloid P component being attached to the first fragment of an Fc region by a hinge region and the two fragments of an Fc region, which are identical or different, being bonded to each other covalently by a bond formed from a spacer chain and a hinge region and form a single polypeptide chain constituting a functional dimeric Fc region (=monomeric SAP-ScFc chimeric protein).

This second implementation variant, characterizing the monomeric SAP-ScFc architecture, is in particular illustrated in FIG. 2 hereinafter.

In this regard, the fragments of an Fc region may preferably be bonded to each other by means of a spacer chain represented by at least one amino acid sequence represented by the sequence SEQ ID NO: 5.

This sequence SEQ ID NO: 5, having the unit (GGGGS)n or (G4S)n, is therefore more or less long depending on the desired flexibility. In this regard, "n" is preferably between 1 and 5, and preferably equal to 3.

In other words, a monomeric SAP-ScFc protein comprises, from the N-terminal part to the C-terminal part. (1) a human amyloid P compound, (2) a hinge region, (3) a first fragment of an Fc region of a human antibody, (4) a spacer chain, (5) a hinge region, identical to or different than that considered in (2) above, and (6) a second fragment of an Fc region of a human antibody, identical to or different than that considered in (3) above.

According to this second implementation variant, the architecture, from the N-terminal part to the C-terminal part, comprising (i) a hinge region, (ii) a first fragment of an Fc region of a human antibody, (iii) a spacer chain, (iv) a hinge region, identical to or different than that considered in (i) above, and (v) a second fragment of an Fc region of a human antibody, identical to or different than that considered in (ii) above, can be represented by at least one amino acid sequence having at least 80% identity with the sequence SEQ ID NO: 11.

In this regard, the architecture, from the N-terminal part to the C-terminal part, comprising (i) a hinge region, (ii) a first fragment of an Fc region of a human antibody, (iii) a spacer chain, (iv) a hinge region, identical to or different than that considered in (i) above, and (v) a second fragment of an Fc region of a human antibody, identical to or different than that considered in (ii) above, can be represented by an amino acid sequence encoded by a nucleic acid sequence having at least 80% identity with the sequence SEQ ID NO: 12.

In the light of the aforementioned, a chimeric protein according to this second implementation variant may comprise at least one amino acid sequence having at least 80% identity with the sequence SEQ ID NO: 9.

A chimeric protein according to this second implementation variant may also comprise at least one amino acid sequence encoded by a nucleic acid sequence having at least 80% identity with the sequence SEQ ID NO: 10.

According to a third implementation variant, the chimeric protein according to the invention may result from the natural pairing of two monomeric SAP-ScFc proteins, bonded to each other by means of at least two disulfide bridges or of at least two bonds, one bond being formed from at least two poly(ethylene glycol) (PEG) groups.

Figure 3:
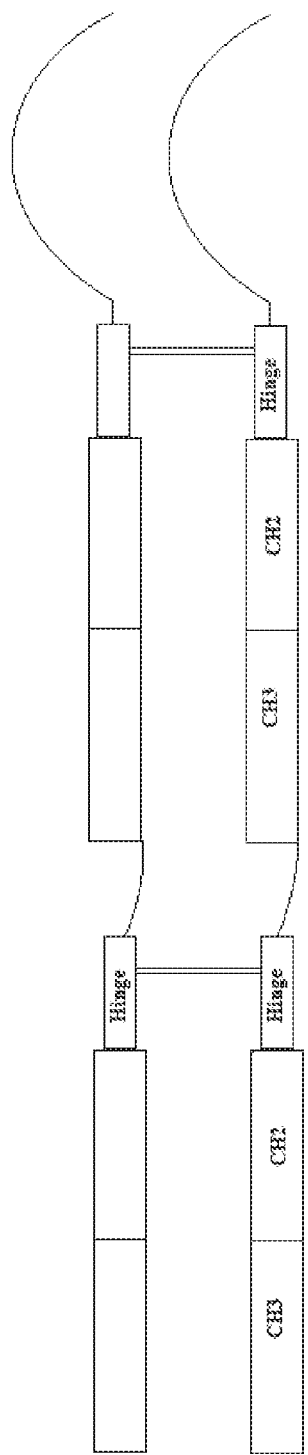
FIG. 3 illustrates a chimeric protein according to the invention resulting from the pairing of two monomeric SAP-ScFc chimeric proteins bonded to each other by two disulfide bridges (=dimeric SAP-ScFc chimeric protein).

This third implementation variant, characterizing the dimeric SAP-ScFc architecture, is in particular illustrated in FIG. 3 hereinafter.

Considering the dimeric SAP-Fc and dimeric SAP-ScFc chimeric proteins, the covalent bond(s) between each monomeric SAP-Fc or monomeric SAP-ScFc unit is (are) preferably located at the level of the cysteine residues of the hinge regions.

Vector Nucleic Acids and Host Cells According to the Invention

According to another of its aspects, the present invention relates to a nucleic acid comprising at least one polynucleotide sequence encoding at least one chimeric protein according to the invention.

Since the formation of the dimeric SAP-Fc and dimeric SAP-ScFc structures results from a natural pairing phenomenon, the polynucleotide sequence preferably encodes at least the monomeric SAP-Fc or monomeric SAP-ScFc chimeric protein.

According to yet another of its aspects, the present invention relates to a vector, preferably an expression vector, into which a nucleic acid as defined above is inserted.

Preferably, a particularly suitable vector is the pCpG vector (Cayla, Invivogen) which allows very good results regarding the production of Ig light chains in SP2/0 and CHO.

According to another of its aspects, the present invention relates to a host cell transfected with a vector as previously defined, in particular a bacterial, yeast or fungal cell or a mammalian cell, or else a cell from transgenic animals.

Preferably, by way of particularly suitable host cell, mention may be made of eukaryotic cells, more particularly cells chosen from the group consisting of the following cells: YB2/0, in particular the line deposited with the "American Type Culture Collection" under ATCC No. CRL-1662), SP2/0, YE2/0, 1R983F, Namalwa, PER.C6, the CHO cell lines, in particular CHO-K-1, CHO-Lec10, CHO-Lec1, CHO-Lec13, CHO Pro-5, CHO dhfr-, Wil-2, Jurkat, Vero, Molt-4, COS-7, 293-HEK, BHK, KGH6, NSO, SP2/0-Ag 14, P3X63Ag8.653, C127, JC, LA7, ZR-45-30, hTERT, NM2C5, UACC-812, DG44 and DXB11, DHFR, HELA, CVI, COS, R1610, BALBC/3T3, HAK, BF1-1c1BPT, RAJI, HEK, EB66, or BHK.

Process for Producing a Chimeric Protein According to the Invention

According to yet another of its aspects, the present invention relates to a process for producing a chimeric protein as previously defined, said process comprising at least the steps consisting in:

a) transfecting a host cell with a vector as defined above;

b) culturing said host cell under conditions such that the chimeric protein is produced; and c) collecting said chimeric protein produced by said host cell at the end of step b).

1) Transfecting Step

For the purposes of the present invention, the term "transfection" refers to the process of introducing exogenous DNA (for example an expression vector as defined above) into eukaryotic cells.

There are various methods for introducing an exogenous DNA into a cell, these methods being part of the conventional techniques known to those skilled in the art.

By way of example of transfection methods, mention may be made of transfection using calcium phosphate, incorporation of the DNA to be transfected into liposomes (for eukaryotic cells, a transfection based on lipids and polycations is preferentially used, owing to the greater sensitivity of the cells), the use of highly branched polycationic agents, called dendrimers, such as polyethyleneimine (PEI), for binding the DNA and transporting it into the cell (Tris is often included in the transfection solution in order to improve membrane permeability), electroporation, heat shock, the particular properties of reagents such as Gene-Cellin, and the gene gun.

Preferably, an appropriate transfection method in the context of the present invention is electroporation, as described, for example, by Potter et al. (2003, Curr Protoc. Mol. Biol., Chapter Unit-9.3, 1-12).

In the light of the aforementioned, the vector used preferably comprises at least one nucleic acid comprising at least one polynucleotide sequence encoding at least one monomeric SAP-Fc or monomeric SAP-ScFc chimeric protein.

2) Step of Culturing the Transfected Cell

Once the transfection step has been carried out, the cells thus obtained are then placed under environmental conditions, and in particular in a culture medium, capable of ensuring their survival and therefore their multiplication, the amplification of the vector, the induction of gene expression and the production of the chimeric protein according to the invention.

This step is also part of the standard knowledge of those skilled in the art.

3) Step of Recovering the Chimeric Protein

During the gene expression, the presence of a trafficking signal peptide upstream of the gene sequence encoding the chimeric protein enables the secretion of said chimeric protein into the culture medium.

The secreted chimeric protein according to the invention therefore no longer contains the sequence relating to the signal peptide.

The criteria for choosing the signal peptide are part of the general knowledge of those skilled in the art and, in particular, can be based on the D-score and the Y-max defined by the Signal IP software.

A signal peptide according to the invention can be represented by an amino acid sequence having at least 80% identity with at least one of the sequences described in WO 2011/114063.

More particularly, a signal peptide according to the invention may also be represented by an amino acid sequence having at least 80% identity with a sequence chosen from the sequences SEQ ID NO: 20 and 22 to 27.

Preferably, the signal peptide is represented by the sequence SEQ ID NO: 25.

After recovery of the cell supernatant, a step of assaying the chimeric protein using the ELISA technique can be carried out. A protein separation/visualization step is then required. This step can be carried out by means of SDS-PAGE electrophoresis or Western blotting.

All these techniques are part of the standard knowledge of those skilled in the art.

4) Additional Steps

In the case where it is sought to obtain a dimeric SAP-Fc or dimeric SAP-ScFc chimeric protein as previously defined, it should be noted that these specific architectures are naturally produced in the host cell.

Preferably, a process according to the invention can also comprise a purifying step d).

Such a purifying step is carried out using the conventional techniques known to those skilled in the art. In this respect, mention may be made of purification on an affinity column coupled to the antigen, on protein A or on protein G, or else an affinity column coupled to anti-SAP aptamers and/or aptamers against a fragment of an Fc region of a human antibody under consideration.

In the event of a process for producing a chimeric protein according to the invention considering the use of a step c), step d) can take place prior to or subsequent to this step c).

In the context of a purification on an affinity column coupled to the antigen, it is possible to imagine a system comprising an anti-SAP antibody so as to isolate the chimeric proteins according to the invention.

The purification method considered can also involve the implementation of an eluting step so as to recover the complexes formed, and therefore the chimeric proteins according to the invention. This eluting step is also part of the conventional techniques known to those skilled in the art.

The chemical protein according to the invention may also be produced from transgenic animals. According to one preferred embodiment, said protein is produced in the milk of non-human transgenic mammals, genetically modified to produce this chemical protein. A transgenic animal according to the invention can be chosen from rabbits, goats, cows, camels, hamsters, mice, rats, horses, sows, dromedaries, ewes and lamas, the list not being limiting. Preferably, it involves the milk from a transgenic doe rabbit or a transgenic goat. The secretion of said protein by the mammary glands, allowing its secretion in the milk of the transgenic mammal, involves controlling its expression in a tissue-dependent manner. Such control methods are well known to those skilled in the art. The expression is controlled by virtue of sequences which allow expression of the protein toward a particular tissue of the animal. These are in particular the WAP, beta-casein, and beta-lactoglobulin promoter sequences and the signal peptide sequences. The process for extracting the proteins of interest from the milk of transgenic animals is in particular described in EP 0 264 166.

Use of a Chimeric Protein According to the Invention

As previously indicated, the present invention relates to the field of obtaining specific chimeric protein for therapeutic use, in particular for treating amyloidosis, in particular amyloidosis of AL type.

Consequently, according to yet another of its aspects, the present invention relates to a pharmaceutical composition comprising a chimeric protein according to the invention and a pharmaceutically acceptable excipient.

As indicated above, a chimeric protein according to the invention may have different architectures. In this respect, a pharmaceutical composition according to the invention may comprise a mixture of chimeric proteins according to the invention having different architectures. More particularly, among all the chimeric proteins according to the invention which can be included in a pharmaceutical composition according to the invention, mention may be made of:

- the chimeric protein comprising two units, each unit comprising a human amyloid P component and a fragment of an Fc region of a human antibody, bonded to each other by a hinge region, the two units being bonded to each other covalently by at least one disulfide bridge (characterizes the dimeric SAP-Fc architecture);
- the chimeric protein comprising a human amyloid P component and two fragments of an Fc region of a human antibody (i.e. first and second fragments of an Fc region of a human antibody), the human amyloid P component being attached to the first fragment of an Fc region by a hinge region and the two fragments of an Fc region, which may be identical or different, being bonded to each other covalently by means of a bond formed from a spacer chain and a hinge region, and form a single polypeptide chain constituting a functional dimeric Fc region (characterizes the monomeric SAP-ScFc architecture); and
- the chimeric protein comprising at least two monomeric SAP-ScFc units bonded to each other covalently by at least two disulfide bridges (characterizes the dimeric SAP-ScFc architecture).

Preferably, a pharmaceutical composition according to the invention is predominantly formed from chimeric proteins comprising two units each comprising a human amyloid P component and a fragment of an Fc region of a human antibody, the two units being bonded to each other covalently by a spacer chain (characterizes the dimeric SAP-Fc architecture), with, for each unit, the human amyloid P component and the fragment of an Fc region of a human antibody being bonded to each other by means of a hinge region.

In certain embodiments, a pharmaceutical composition according to the invention may be in liquid form.

In certain embodiments, a pharmaceutical composition according to the invention may be in solid form, said form comprising a lyophilized form.

A pharmaceutical composition according to the invention can be formulated according to standard methods such as those described in Remington: The Science and Practice of Pharmacy (Lippincott Williams & Wilkins; Twenty First Edition, 2005).

By way of pharmaceutically acceptable excipient, mention may in particular be made of those described in Handbook of Pharmaceutical Excipients, American Pharmaceutical Association (Pharmaceutical Press; 6th revised edition, 2009).

In order to treat a patient in need of said treatment, i.e. a patient suffering from at least one of the indications considered in the present application, a therapeutically effective dose of the composition according to the invention can be administered.

The term "therapeutically effective dose" is intended to mean a dose which produces expected effects for which a composition according to the invention is administered. The exact dose will depend on the purpose of the treatment, and will be verifiable by those skilled in the art using known techniques. The doses that can be considered can range from 0.001 to 100 mg of chimeric proteins according to the invention, per kg of body weight (mg/kg) or more, for example 0.1, 1.0, 10 or 50 mg/kg of body weight, with 1 to 10 mg/kg being preferred. The dosage and the administration frequency can be adjusted according to the response by the treated patient, and the injection frequency.

Preferably, the chimeric protein can be administered at a dose ranging from 0.1 to 1000 µg/kg of body weight.

As is known in the art, adjustments given the degradation of the proteins, systemic compared with localized administration, and age, weight, general health, sex, diet, administration time, drug interactions and seriousness of the condition of the patient may be necessary, and can be easily determined by those skilled in the art by means of routine experimentation.

The administration of a pharmaceutical composition according to the invention can be carried out in several ways, including, but without being limited thereto, via the local and cutaneo-mucosal route, via the enteral route or via the parenteral route.

The term "local and cutaneo-mucosal route" is intended in particular to denote the topical, intra-auricular, intravaginal, intra-uterine, inhalation, transdermal, ocular or intravesical route.

The term "enteral route" is intended in particular to denote the intrarectal, sublingual, buccal, nasal, intra-stomach or intrajejunal route.

The term "parenteral route" is intended in particular to denote the intradermal, subcutaneous, intramuscular, intracardiac, intravascular, intravenous, intra-ocular, intra-arterial, epidural, intraspinal, extracorporeal, intrathecal, intraperitoneal, intrapleural, intraluminal, intravitreal, intracavernous, intraventricular, intra-bone, palatine, intra-articular, intracellular, pulmonary or intrafetal route.

Preferably, the administration of a pharmaceutical composition according to the invention can be carried out via the intravenous (IV) or subcutaneous (SC) route according to an administration scheme derived from a standard protocol used in treatment by passive immunotherapy. Other modes of administration such as local injection or aerosol administration can also be used.

The composition of the invention can be administered concomitantly with other therapeutic agents, in particular specific treatments for overcoming the functional insufficiency or insufficiencies of the organ or organs affected by the amyloid deposits.

According to yet another of its aspects, the present invention relates to a chimeric protein as defined above, for use thereof as a medicament.

According to yet another of its aspects, the present invention relates to a chimeric protein as defined above, for use thereof for eliminating the amyloidosis deposits in the organs.

According to yet another of its aspects, the present invention relates to a chimeric protein as defined above, which, by integrating into the human amyloid deposit, will induce a recruitment of effector cells such as monocyte-macrophages and polymorphonuclear cells and as a result induce the elimination of the amyloid deposits by phagocytosis.

According to yet another of its aspects, the present invention relates to a chimeric protein as defined above, for use thereof for treating amyloidosis, in particular amyloidosis of AL type.

According to yet another of its aspects, the present invention relates to a process for treating amyloidosis, in particular amyloidosis of AL type, comprising at least one step of administering, to an individual in need thereof, an effective amount of at least one first active agent represented by a chimeric protein as previously defined.

According to one particular embodiment, said process can also comprise a step of administering, prior to, concomitantly with and/or subsequent to the step of administering the first active agent, a second active agent distinct from said first active agent, the second active agent preferably being chosen from the group comprising 4-[bis(chloroethyl)amino]phenylalanine (melphalan); 9-fluoro-11β,17,21-trihydroxy-16a-methylpregna-1,4-diene-3,20-dione (dexamethasone); prednisone; dimethyl sulfoxide (DMSO); N-[(7S)-5,6,7,9-tetrahydro-1,2,3,10-tetramethoxy-9-oxobenzo[a]heptalen-7-yl)acetamide] (colchicine); (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione (doxorubicin); agents capable of reacting with the amyloid P component, in particular of bis-d-proline type, and more particularly the compound (R)-1-[6-[(R)-2-carboxypyrrolidin-1-yl]-6-oxohexanoyl]pyrrolidine-2-carboxylic acid); proteasome inhibitors, for example bortezomib, carfilzomib, marizomib, ixazomib, delanzomib, ONX-912 or revlimid; and a mixture thereof.

A chimeric protein according to the invention can also be identified by means of any technique known to those skilled in the art. In this respect, mention may in particular be made of the technique via coupling with fluorophores and the microbeads as described in Neri et al. (1997) Nat Biotech, or else the techniques described in Brack et al. (2005) EJNM, Santimaria (2003) Clinical cancer res, Borsi et al. (2002) Int J cancer, Berndorff (2006) J Nucl Med and Joseph et al. (2004) Pham Res.

Process for Identifying Amyloid Deposits

According to yet another of its aspects, a chimeric protein according to the invention is also advantageous in that it can be taken advantage of for use as a tool for in vitro or ex vivo characterization of the presence of an amyloidosis deposit.

According to this aspect of the invention, said chimeric protein can be labeled using a detectable molecule. For example, according to a first variant, said chimeric protein can be radiolabeled; preferably, the human amyloid P component is represented by $^{123}$I-SAP. According to a second variant, the chimeric protein can be identified by means of a radiolabeled anti-Fc antibody; for example, said anti-Fc antibody is coupled to peroxidase.

Preferably, for obvious reasons, said anti-Fc antibody is of human origin.

By way of peroxidase-coupled anti-Fc, it is possible to use any antibody available on the market, showing good specificity and an interaction with the Fc part of the Fc-SAP fusion protein. By way of example, mention may be made of that sold under the name A0170 by the company Sigma-Aldrich.

A chimeric protein according to the invention can also be identified by means of any technique known to those skilled in the art. In this respect, mention may in particular be made of the technique via coupling with fluorophores and microbeads as described in Neri et al. (1997) Nat Biotech, or else the techniques described in Brack et al. (2005) EJNM, Santimaria (2003) Clinical cancer res, Borsi et al. (2002) Int J cancer, Berndorff (2006) J Nucl Med and Joseph et al. (2004) Pham Res.

TABLE 2

Sequences

| SEQ ID NO: | Type | Description |
|---|---|---|
| 1 | Peptide | Human amyloid P component |
| 2 | Nucleic acid | Human amyloid P component |
| 3 | Peptide | Fragment of an Fc region of a human antibody |
| 4 | Nucleic acid | Fragment of an Fc region of a human antibody |
| 5 | Peptide | Non-structuring peptide sequence between SAP and a hinge region, or spacer chain between two fragments of an Fc region of a human antibody at the level of SAP-ScFc |
| 6 | Nucleic acid | Non-structuring peptide sequence between SAP and a hinge region, or spacer chain between two fragments of an Fc region of a human antibody at the level of SAP-ScFc |
| 7 | Peptide | Secreted monomeric SAP-Fc |
| 8 | Nucleic acid | Secreted monomeric SAP-Fc |
| 9 | Peptide | Secreted monomeric SAP-ScFc |
| 10 | Nucleic acid | Secreted monomeric SAP-ScFc |
| 11 | Peptide | Hinge region + the two fragments of an Fc region of a human antibody, bonded to each other by a spacer chain and a hinge region of SAP-ScFc |
| 12 | Nucleic acid | Hinge region + the two fragments of an Fc region of a human antibody, bonded to each other by a spacer chain and a hinge region of SAP-ScFc |
| 13 | Peptide | Human IgG1 hinge region |
| 14 | Nucleic acid | Human IgG1 hinge region |
| 15 | Peptide | Human IgG2 hinge region |
| 16 | Peptide | Human IgG3 hinge region |
| 17 | Peptide | Human IgG3 hinge region |
| 18 | Peptide | Human IgG4 hinge region |
| 19 | Peptide | Shortened human IgG1 hinge region |
| 20 | Peptide | Natural signal peptide of SAP |
| 21 | Nucleic acid | Natural signal peptide of SAP |
| 22 | Peptide | MMP1 human TIMP signal peptide |
| 23 | Peptide | Human insulin signal peptide |
| 24 | Peptide | Human EPO signal peptide |
| 25 | Peptide | MB7 signal peptide |
| 26 | Peptide | AMHRII signal peptide |
| 27 | Peptide | XXII49 signal peptide |
| 28 | Nucleic acid | SAP of example 1 |
| 29 | Nucleic acid | Fragment of an Fc region of a human antibody of example 1 |
| 30 | Nucleic acid | Monomeric SAP-Fc of example 1 |
| 31 | Peptide | Monomeric SAP-Fc of example 1 |
| 32 | Nucleic acid | First fragment of an Fc region of a human antibody of example 2 |
| 33 | Nucleic acid | Second fragment of an Fc region of a human antibody of example 2 |
| 34 | Nucleic acid | Spacer chain between the first and second fragments of an Fc region of a human antibody of example 2 |
| 35 | Nucleic acid | Monomeric SAP-ScFc of example 2 |
| 36 | Peptide | Monomeric SAP-ScFc of example 2 |
| 37 | Nucleic acid | First primer for SAP amplification in example 1 |
| 38 | Nucleic acid | Second primer for SAP amplification in example 1 |
| 39 | Nucleic acid | First primer for amplification of the fragment of an Fc region of a human antibody in example 1 |
| 40 | Nucleic acid | Second primer for amplification of the fragment of an Fc region of a human antibody in example 1 |
| 41 | Nucleic acid | First primer for amplification of the first fragment of an Fc region of a human antibody in example 2 |
| 42 | Nucleic acid | Second primer for amplification of the first fragment of an Fc region of a human antibody in example 2 |
| 43 | Nucleic acid | First primer for amplification of the second fragment of an Fc region of a human antibody in example 2 |
| 44 | Nucleic acid | Second primer for amplification of the second fragment of an Fc region of a human antibody in example 2 |

TABLE 2-continued

| SEQ ID NO: | Type | Description |
|---|---|---|
| 45 | Nucleic acid | First primer for amplification of the spacer chain in example 2 |
| 46 | Nucleic acid | Second primer for amplification of the spacer chain in example 2 |

The examples and figures which follow are presented by way of nonlimiting illustration of the invention.

EXAMPLES

Preliminarily, it should be noted that the sequence corresponding to the human amyloid P component used hereinafter is identified, in particular, by means of its sequence number as considered hereinafter, to which is added, in the N-terminal part, a specific sequence corresponding to the natural signal peptide of said component. In the case in point, the signal peptide considered is that represented by the amino acid sequence SEQ ID NO: 20, or even the nucleic acid sequence SEQ ID NO: 21.

Example 1: Construction of the Monomeric SAP-Fc Vector

A) Amplification of the cDNA Fragment Encoding Human SAP:

For the construction of the monomeric SAP-Fc vector, the human amyloid P component (SAP) was amplified from human cDNA with the Phusion Taq polymerase. The STOP codon was not amplified. A Kozak sequence was added upstream of the starting ATG of the sequence. The sequence was bordered by 2 SalI restriction sites, added in the primers used for the amplification. What is more, in the sequence considered, only the 2 exons making up the SAP are present, the intron not being in this construct.

The human SAP cDNA sequence used, corresponding to the sequence SEQ ID NO: 28 hereinafter, is therefore the following:

GTCGACACCATGAACAAGCCGCTCTTTGGATCTCTGTCCTCACCAGCCTC

CTGGAAGCCTTTGCTCACACAGACCTCAGTGGGAAGGTGTTTGTATTTCC

TAGAGAATCTGTTACTGATCATGTAAACTTGATCACACCGCTGGAGAAGC

CTCTACAGAACTTTACCTTGTGTTTTCGAGCCTATAGTGATCTCTCTCGT

GCCTACAGCCTCTTCTCCTACAATACCCAAGGCAGGGATAATGAGCTACT

AGTTTATAAAGAAAGAGTTGGAGAGTATAGTCTATACATTGGAAGACACA

AAGTTACATCCAAAGTTATCGAAAAGTTCCCGGCTCCAGTGCACATCTGT

GTGAGCTGGGAGTCCTCATCAGGTATTGCTGAATTTTGGATCAATGGGAC

ACCTTTGGTGAAAAAGGGTCTGCGACAGGGTTACTTTGTGGAAGCTCAGC

CCAAGATTGTCCTGGGGCAGGAACAGGATTCCTATGGGGCAAGTTTGAT

AGGAGCCAGTCCTTTGTGGGAGAGATTGGGGATTTGTACATGTGGGACTC

TGTGCTGCCCCCAGAAAATATCCTGTCTGCCTATCAGGGTACCCCTCTCC

CTGCCAATATCCTGGACTGGCAGGCTCTGAACTATGAAATCAGAGGATAT

GTCATCATCAAACCCTTGGTGTGGGTCGAC

The PCR primers used to amplify the SAP are:

hSAPforSal:
(SEQ ID NO: 37)
acttgGTCGACaccatgaacaagccgctgctttg hSAPrevfusSal:
(SEQ ID NO: 38)
actagGTCGACccacaccaagggtttga.

The PCR amplification was carried out using the conventional techniques known to those skilled in the art. In this respect, mention may be made of the standard protocols described in Current Protocols in Molecular Biology (Frederick M. AUSUBEL, 2000, Wiley and son Inc, Library of Congress, USA).

B) Amplification of the cDNA Fragment Encoding the Fragment of an Fc Region of a Human Antibody The nucleic acid encoding the fragment of an Fc region of a human antibody (with its STOP codon), also including a nucleic sequence corresponding to a hinge region in the N-terminal region of said nucleic acid, was amplified from total cDNA extracted from human bone marrow. The Fc domain considered is that of a human IgG1 (IGHG1*03). The amplification of the Fc domain sequence was carried out with the Phusion Taq polymerase. The Fc fragment was bordered by 2 restriction sites, XhoI and BspEI, added in the primers during the amplification.

The cDNA sequence encoding the considered fragment of an Fc region of a human antibody, corresponding to the sequence SEQ ID NO: 29 hereinafter, is therefore the following:

ATACTCTCGAGCCCAAATCTTGTGACAAAACTCACACATGCCCACC

GTGCCCAGCACCTGAACTCCTGGGGGACCGTCAGTCTTCCTCTTCCCCC

CAAAACCCAAGGACACCCTCATGATCTCCCGGACCCCTGAGGTCACATGC

GTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGC

AGTACAACAGCACGTACCGTGTGGTCAGCGTCCTCACCGTCCTGCACCAG

GACTGGCTGAATGGCAAGGAGTACAAGTGCAAGGTCTCCAACAAAGCCCT

CCCAGCCCCCATCGAGAAAACCATCTCCAAAGCCAAAGGGCAGCCCCGAG

AACCACAGGTGTACACCCTGCCCCCATCCCGGGAGGAGATGACCAAGAAC

CAGGTCAGCCTGACCTGCCTGGTCAAAGGCTTCTATCCCAGCGACATCGC

CGTGGAGTGGGAGAGCAATGGGCAGCCGGAGAACAACTACAAGACCACGC

CTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTC

CGGGTAAATGAGTGCTCCGGACAGAT

The PCR primers used to amplify the considered fragment of an Fc region of a human antibody are:

hG1hingeforfusXho:
(SEQ ID NO: 39)
CTCGAGcccaaatcttgtgacaa hG1CH3rev BspE I:
(SEQ ID NO: 40)
TCCGGAgcactcatttacccggagac.

C) Construction of the Monomeric SAP-Fc Vector

Figure 4:
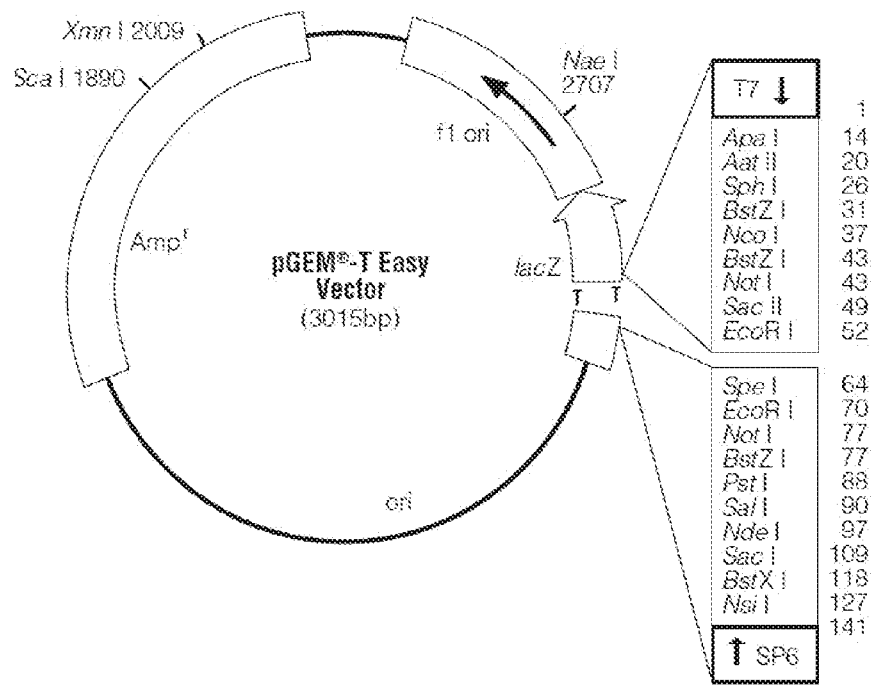
FIG. 4 illustrates the commercial cloning vector pGEM®-T Easy (Promega).

The SAP and Fc fragments are firstly cloned into the commercial vector pGEM®-T Easy (Promega) (see FIG. 4 hereinafter) so as to sequence them (pGEMT-SAP and pGEMT-Fc).

The fragment encoding human SAP was cleaved and isolated from the pGEMT-SAP vector using the SalI restriction enzyme (one site on each side of the fragment) and then inserted into the pGEMT-Fc vector upstream of the fragment encoding the Fc domain cleaved beforehand using the XhoI restriction enzyme (compatible with SalI).

Figure 5:
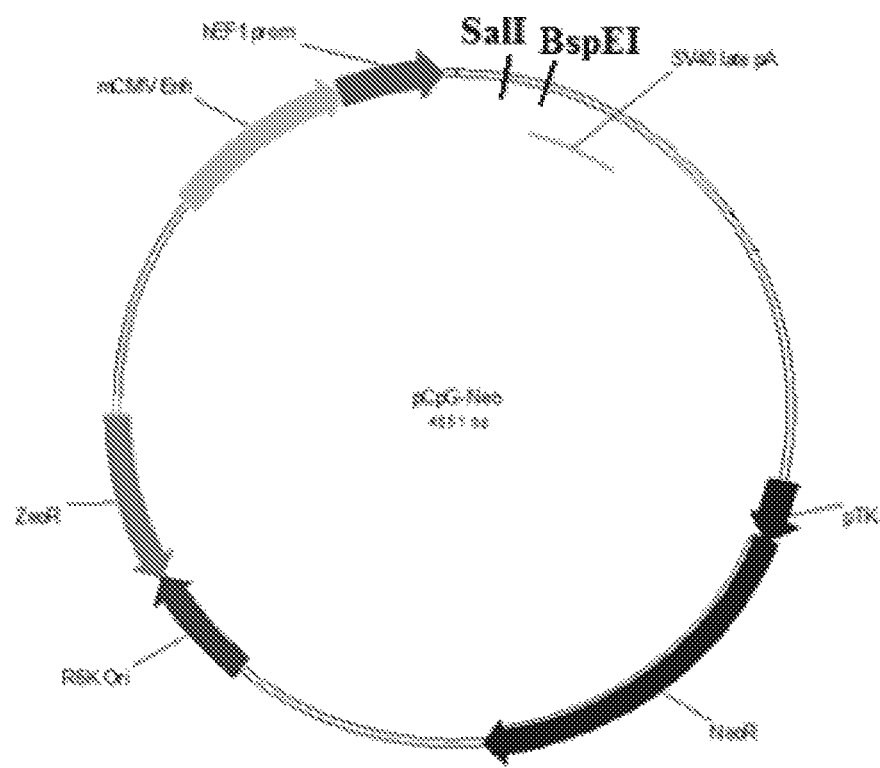
FIG. 5 illustrates the commercial expression vector pCpG (invivogen).

Once the monomeric SAP-Fc had been established, cleavage with the SalI and BspEI restriction enzymes made it possible to insert the monomeric SAP-Fc fragment into the pCpGfree expression vector (invivogen), (see FIG. 5 hereinafter) digested with the same pair of enzymes, said expression vector having been modified beforehand so as to contain the SalI and BspEI restriction sites in the original multiple cloning site and also a functional neomycin resistance cassette.

Complete sequencing was then carried out using a method derived from the Sanger method (Sanger F, Nicklen S, Coulson A R, PNAS, 1977). The DNA is prepared so as to have fragments of all sizes, the last base of which is one of the 4 ddNTPs, labeled with a fluorochrome, which blocks the polymerization reaction. The fragments migrate according to their sizes in the capillary tube, and the various fluorochromes are excited by a laser which makes it possible to establish the sequence. The sequencing reaction requires, in addition to the DNA to be sequenced, the forward or reverse primer, the buffer and the BigDye® (Applied Biosystems) which contains the DNA polymerase, the dNTPs and the ddNTPs. The PCR program is the following: 96° C. for 1 minute, then 25 cycles composed of a dehybridization step at 96° C. for 10 seconds, then a primer hybridization step at 50° C. for 5 seconds, followed by an elongation step at 60° C. for 4 min.

In order to eliminate all the constituents which can interfere during the migration in the capillary tubes, the sequence products are purified on Sephadex™ G50 gel (GE Healthcare). The Sephadex powder is distributed in the wells of the filtration plate (Millipore) and then left for 3 hours with 300 μl of water. The excess water is removed by centrifugation for 3 min at 910 g.

Next, the sequence products are deposited in the wells on the gel, centrifuged for 3 min at 910 g and recovered in a sequencing plate. The sequencing is carried out on an ABI 3130 automatic sequencer (Applied Biosystems).

The nucleic acid sequence of monomeric SAP-Fc, corresponding to the sequence SEQ ID NO: 30, is the following:

ATGAACAAGCCGCTCCTTTGGATCTCTGTCCTCACCAGCCTCCTGGA

AGCCTTTGCTCACACAGACCTCAGTGGGAAGGTGTTTGTATTTCCTAGAG

AATCTGTTACTGATCATGTAAACTTGATCACACCGCTGGAGAAGCCTCTA

CAGAACTTTACCTTGTGTTTTCGAGCCTATAGTGATCTCTCTCGTGCCTA

CAGCCTCTTCTCCTACAATACCCAAGGCAGGGATAATGAGCTACTAGTTT

ATAAAGAAAGAGTTGGAGAGTATAGTCTATACATTGGAAGACACAAAGTT

ACATCCAAAGTTATCGAAAAGTTCCCGGCTCCAGTGCACATCTGTGTGAG

CTGGGAGTCCTCATCAGGTATTGCTGAATTTTGGATCAATGGGACACCTT

TGGTGAAAAAGGGTCTGCGACAGGGTTACTTTGTGGAAGCTCAGCCCAAG

ATTGTCCTGGGGCAGGAACAGGATTCCTATGGGGGCAAGTTTGATAGGAG

CCAGTCCTTTGTGGGAGAGATTGGGGATTTGTACATGTGGGACTCTGTGC

TGCCCCCAGAAAATATCCTGTCTGCCTATCAGGGTACCCCTCTCCCTGCC

AATATCCTGGACTGGCAGGCTCTGAACTATGAAATCAGAGGATATGTCAT

CATCAAACCCTTGGTGTGGGTCGAGCCCAAATCTTGTGACAAAACTCACA

CATGCCCACCGTGCCCAGCACCTGAACTCCTGGGGGGACCGTCAGTCTTC

CTCTTCCCCCCAAAACCCAAGGACACCCTCATGATCTCCCGGACCCCTGA

GGTCACATGCGTGGTGGTGGACGTGAGCCACGAAGACCCTGAGGTCAAGT

TCAACTGGTACGTGGACGGCGTGGAGGTGCATAATGCCAAGACAAAGCCG

CGGGAGGAGCAGTACAACAGCACGTACCGTGTGGTCAGCGTCCTCACCGT

CCTGCACCAGGACTGGCTGAATGGCAAGGAGTACAAGTGCAAGGTCTCCA

ACAAAGCCCTCCCAGCCCCCATCGAGAAAACCATCTCCAAAGCCAAAGGG

CAGCCCCGAGAACCACAGGTGTACACCCTGCCCCCATCCCGGGAGGAGAT

GACCAAGAACCAGGTCAGCCTGACCTGCCTGGTCAAAGGCTTCTATCCCA

GCGACATCGCCGTGGAGTGGGAGAGCAATGGGCAGCCGGAGAACAACTAC

AAGACCACGCCTCCCGTGCTGGACTCCGACGGCTCCTTCTTCCTCTACAG

CAAGCTCACCGTGGACAAGAGCAGGTGGCAGCAGGGGAACGTCTTCTCAT

GCTCCGTGATGCATGAGGCTCTGCACAACCACTACACGCAGAAGAGCCTC

TCCCTGTCTCCGGGTAAATGA

The corresponding protein sequence of the monomeric SAP-Fc, corresponding to the sequence SEQ ID NO: 31, is the following:

MNKPLLWISVLTSLLEAFAHTDLSGKVFVFPRESVTDHVNLITPLEKPL

QNFTLCFRAYSDLSRAYSLFSYNTQGRDNELLVYKERVGEYSLYIGRHKV

TSKVIEKFPAPVHICVSWESSSGIAEFWINGTPLVKKGLRQGYFVEAQPK

IVLGQEQDSYGGKFDRSQSFVGEIGDLYMWDSVLPPENILSAYQGTPLPA

NILDWQALNYEIRGYVIIKPLVWVEPKSCDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSL

SLSPGK-

The corresponding protein sequence of the secreted monomeric SAP-Fc is the following sequence SEQ ID NO: 7:

HTDLSGKVFVFPRESVTDHVNLITPLEKPLQNFTLCFRAYSDLSRAYSL

FSYNTQGRDNELLVYKERVGEYSLYIGRHKVTSKVIEKFPAPVHICVSWE

SSSGIAEFWINGTPLVKKGLRQGYFVEAQPKIVLGQEQDSYGGKFDRSQS

FVGEIGDLYMWDSVLPPENILSAYQGTPLPANILDWQALNYEIRGYVIIK

PLVWVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKL

TVDKSRWQQGNVFSCSVMHEALHNHYTQKSLSLSPGK-

Example 2: Construction of the Monomeric SAP-ScFc Vector

A) Amplification of the DNA Fragment Encoding Human SAP:

See example 1.A) above.

B) Amplification of the First Fragment of cDNA Encoding the First Fragment of an Fc Region of a Human Antibody The nucleic acid encoding the first fragment of an Fc region of a human antibody was amplified from a laboratory vector containing the cDNA of a human IgG1 (IGHG1*03). The amplification of the Fc domain sequence was carried out with the Phusion Taq polymerase. The Fc fragment was bordered by 2 restriction sites, XhoI and HindIII, added in the primers during the amplification. The STOP codon was not amplified.

The cDNA sequence encoding the first fragment of an Fc region of a human antibody, corresponding to the sequence SEQ ID NO: 32 hereinafter, is the following sequence:

GCACCTGAACTCCTGGGGGACCGTCAGTCTTCCTCTTCCCCCCAAA

ACCCAAGGACACCCTCATGATCTCCCGGACCCCTGAGGTCACATGCGTGG

TGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACC

ACAGGTGTACACCCTGCCCCCATCCCGGGAGGAGATGACCAAGAACCAGG

TCAGCCTGACCTGCCTGGTCAAAGGCTTCTATCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTATAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAGCTT

The PCR primers used to amplify the sequence of the fragment of an Fc region of a human antibody are:

```
hG1hingeforfusXho:
                                  (SEQ ID NO: 41)
atactCTCGAGcccaaatcttgtgacaa hG1CH3revfusHind:
                                  (SEQ ID NO: 42)
atctgAAGCTTacccggagacagggaga.
```

C) Amplification of the Second Fragment of DNA Encoding the Second Fragment of an Fc Region of a Human Antibody:

The nucleic acid encoding the second fragment of an Fc region of a human antibody, also including a nucleic sequence corresponding to a hinge region in the N-terminal region of said nucleic acid, was bordered by 2 restriction sites, BglII and BspEI, added in the primers during the amplification. The STOP codon was amplified for this second fragment of an Fc region of a human antibody.

The cDNA sequence encoding the second fragment of an Fc region of a human antibody, corresponding to the sequence SEQ ID NO: 33 hereinafter, is therefore the following:

AGATCTGAGCCCAAATCTTGTGACAAAACTCACACATGCCCACCGT

GCCCAGCACCTGAACTCCTGGGGGGACCGTCAGTCTTCCTCTTCCCCCCA

AAACCCAAGGACACCCTCATGATCTCCCGGACCCCTGAGGTCACATGCGT

GGTGGTGGACGTGAGCCACGAAGACCCTGAGGTCAAGTTCAACTGGTACG

TGGACGGCGTGGAGGTGCATAATGCCAAGACAAAGCCGCGGGAGGAGCAG

TACAACAGCACGTACCGTGTGGTCAGCGTCCTCACCGTCCTGCACCAGGA

CTGGCTGAATGGCAAGGAGTACAAGTGCAAGGTCTCCAACAAAGCCCTCC

CAGCCCCCATCGAGAAAACCATCTCCAAAGCCAAAGGGCAGCCCCGAGAA

CCACAGGTGTACACCCTGCCCCCATCCCGGGAGGAGATGACCAAGAACCA

GGTCAGCCTGACCTGCCTGGTCAAAGGCTTCTATCCCAGCGACATCGCCG

TGGAGTGGGAGAGCAATGGGCAGCCGGAGAACAACTACAAGACCACGCCT

CCCGTGCTGGACTCCGACGGCTCCTTCTTCCTCTACAGCAAGCTCACCGT

GGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCG

GGTAAATGAGTGCTCCGGA

The PCR primers used to amplify the sequence of the second fragment of an Fc region of a human antibody are:

```
hG1hingeforfusBgl:
                                  (SEQ ID NO: 43)
aagtaAGATCTgagcccaaatcttgtgacaa hG1CH3revBspE:
                                  (SEQ ID NO: 44)
atctgTCCGGAgcactcatttacccggagac.
```

D) Amplification of the Spacer Chain Between the Two Fragments of an Fc Region of a Human Antibody:

The sequence of the spacer chain was amplified from a laboratory vector containing the sequence of an ScFv. This sequence encodes a peptide of 15 amino acids (Gly4Ser repeated 3 times). The amplification of the spacer chain was carried out by means of the Phusion Taq polymerase. The sequence of the spacer chain ends with a BamHI restriction site already present in the laboratory vector. The HindIII restriction site is added by the Forward primer during the amplification.

The sequence encoding the spacer chain, corresponding to the sequence SEQ ID NO: 34 hereinafter, is therefore the following:

AAGCTTGGTGGAGGCGGTTCAGGCGGAGGTGGCTCTGGCGGTGGCGGATCC

The PCR primers used to amplify the sequence of the linker are:

LinkforHind III:
(SEQ ID NO: 45)
AAGCTTggtggaggcggttcagg

LinkrevBHI:
(SEQ ID NO: 46)
GGATCCgccaccgccagagcca.

E) Construction of the Monomeric SAP-ScFc Vector

The various fragments making up the monomeric SAP-ScFc were firstly cloned independently into the commercial vector pGEMT-easy (Promega) (see FIG. 4 hereinafter) so as to sequence them. This produced the vectors respectively called: pGEMT-SAP, pGEMT-first Fc, pGEMT-linker and pGEMT-second Fc.

The expression vectors considered were modified beforehand so as to contain the Xho/Hind (for the first Fc fragment) and Bgl/BspE1 (for the second Fc fragment) restriction sites in the original multiple cloning site and also a functional neomycin resistance cassette.

The fragment encoding the human SAP present in the pGEMT-SAP vector was cleaved and isolated using the SalI restriction enzyme (one site on each side of the fragment) and then inserted into the pGEMT-first Fc vector containing the sequence of the first fragment of an Fc region of a human antibody, upstream of said fragment, previously cleaved using the XhoI restriction enzyme.

The HindIII/NotI cleaved linker (the NotI site being present in 3' of the multiple cloning site of the pGEMT-Easy vector) was then added downstream of the first fragment of an Fc region of a human antibody in the pGEMT-SAP-first Fc vector following digestion using the HindIII and NotI restriction enzymes.

The second fragment of an Fc region of a human antibody was then cleaved and isolated from the pGEMT-second Fc vector using the Bg1II/NotI enzymes and then inserted into the pGEMT-SAP-first Fc-linker vector digested using the BamHI/NotI restriction enzymes.

Once the SAP-ScFc had been established, cleavage using the SalI and BspeI restriction enzymes made it possible to insert the SAP-ScFc fragment into the pCpG expression vector (invivogen) previously modified to contain the SalI and BspEI restriction sites in the original multiple cloning site and also a functional neomycin resistance cassette (see FIG. 4 hereinafter) digested with the same pair of enzymes.

Complete sequencing was then carried out.

The nucleic acid sequence of the monomeric SAP-ScFc, corresponding to the sequence SEQ ID NO: 35 hereinafter, is the following:

ATGAACAAGCCGCTCCTTTGGATCTCTGTCCTCACCAGCCTCCTGGA

AGCCTTTGCTCACACAGACCTCAGTGGGAAGGTGTTTGTATTTCCTAGA

GAATCTGTTACTGATCATGTAAACTTGATCACACCGCTGGAGAAGCCTC

TACAGAACTTTACCTTGTGTTTTCGAGCCTATAGTGATCTCTCTCGTGC

CTACAGCCTCTTCTCCTACAATACCCAAGGCAGGGATAATGAGCTACTA

GTTTATAAAGAAAGAGTTGGAGAGTATAGTCTATACATTGGAAGACACA

AAGTTACATCCAAAGTTATCGAAAAGTTCCCGGCTCCAGTGCACATCTG

TGTGAGCTGGGAGTCCTCATCAGGTATTGCTGAATTTTGGATCAATGGG

ACACCTTTGGTGAAAAAGGGTCTGCGACAGGGTTACTTTGTGGAAGCTC

AGCCCAAGATTGTCCTGGGGCAGGAACAGGATTCCTATGGGGGCAAGTT

TGATAGGAGCCAGTCCTTTGTGGGAGAGATTGGGGATTTGTACATGTGG

GACTCTGTGCTGCCCCCAGAAAATATCCTGTCTGCCTATCAGGGTACCC

CTCTCCCTGCCAATATCCTGGACTGGCAGGCTCTGAACTATGAAATCAG

AGGATATGTCATCATCAAACCCTTGGTGTGGGTCGAGCCCAAATCTTGT

GACAAAACTCACACATGCCCACCGTGCCCAGCACCTGAACTCCTGGGGG

GACCGTCAGTCTTCCTCTTCCCCCCAAAACCCAAGGACACCCTCATGAT

CTCCCGGACCCCTGAGGTCACATGCGTGGTGGTGGACGTGAGCCACGAA

GACCCTGAGGTCAAGTTCAACTGGTACGTGGACGGCGTGGAGGTGCATA

ATGCCAAGACAAAGCCGCGGGAGGAGCAGTACAACAGCACGTACCGTGT

GGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAA

CCATCTCCAAAGCCAAAGGGCAGCCCCGAGAACCACAGGTGTACACCCT

GCCCCCATCCCGGGAGGAGATGACCAAGAACCAGGTCAGCCTGACCTGC

CTGGTCAAAGGCTTCTATCCCAGCGACATCGCCGTGGAGTGGGAGAGCA

ATGGGCAGCCGGAGAACAACTACAAGACCACGCCTCCCGTGCTGGACTC

CGACGGCTCCTTCTTCCTCTATAGCAAGCTCACCGTGGACAAGAGCAGG

TGGCAGCAGGGGAACGTCTTCTCATGCTCCGTGATGCATGAGGCTCTGC

ACAACCACTACACGCAGAAGAGCCTCTCCCTGTCTCCGGGTAAGCTTGG

TGGAGGCGGTTCAGGCGGAGGTGGCTCTGGCGGTGGCGGATCTGAGCCC

AAATCTTGTGACAAAACTCACACATGCCCACCGTGCCCAGCACCTGAAC

TCCTGGGGGGACCGTCAGTCTTCCTCTTCCCCCCAAAACCCAAGGACAC

CCTCATGATCTCCCGGACCCCTGAGGTCACATGCGTGGTGGTGGACGTG

AGCCACGAAGACCCTGAGGTCAAGTTCAACTGGTACGTGGACGGCGTGG

AGGTGCATAATGCCAAGACAAAGCCGCGGGAGGAGCAGTACAACAGCAC

GTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCA

TCGAGAAACCATCTCCAAAGCCAAAGGGCAGCCCCGAGAACCACAGGT

GTACACCCTGCCCCCATCCCGGGAGGAGATGACCAAGAACCAGGTCAGC

CTGACCTGCCTGGTCAAAGGCTTCTATCCCAGCGACATCGCCGTGGAGT

GGGAGAGCAATGGGCAGCCGGAGAACAACTACAAGACCACGCCTCCCGT

GCTGGACTCCGACGGCTCCTTCTTCCTCTACAGCAAGCTCACCGTGGAC

-continued
```
AAGAGCAGGTGGCAGCAGGGGAACGTCTTCTCATGCTCCGTGATGCATG

AGGCTCTGCACAACCACTACACGCAGAAGAGCCTCTCCCTGTCTCCGGG

TAAATGA
```

The corresponding protein sequence of the monomeric SAP-ScFc, corresponding to the sequence SEQ ID NO: 36 hereinafter, is the following:

```
MNKPLLWISVLTSLLEAFAHTDLSGKVFVFPRESVTDHVNLITPLEKPL

QNFTLCFRAYSDLSRAYSLFSYNTQGRDNELLVYKERVGEYSLYIGRHKV

TSKVIEKFPAPVHICVSWESSSGIAEFWINGTPLVKKGLRQGYFVEAQPK

IVLGQEQDSYGGKFDRSQSFVGEIGDLYMWDSVLPPENILSAYQGTPLPA

NILDWQALNYEIRGYVIIKPLVWVEPKSCDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSL

SLSPGKLGGGGSGGGGSGGGGSEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSL

SPGK-
```

The corresponding protein sequence of the secreted monomeric SAP-ScFc, corresponding to the sequence SEQ ID NO: 9 hereinafter, is the following:

```
HTDLSGKVFVFPRESVTDHVNLITPLEKPLQNFTLCFRAYSDLSRAYSL

FSYNTQGRDNELLVYKERVGEYSLYIGRHKVTSKVIEKFPAPVHICVSWE

SSSGIAEFWINGTPLVKKGLRQGYFVEAQPKIVLGQEQDSYGGKFDRSQS

FVGEIGDLYMWDSVLPPENILSAYQGTPLPANILDWQALNYEIRGYVIIK

PLVWVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKL

TVDKSRWQQGNVFSCSVMHEALHNHYTQKSLSLSPGKLGGGGSGGGGSGG

GGSEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTV

DKSRWQQGNVFSCSVMHEALHNHYTQKSLSLSPGK-
```

Example 3: Production of SAP-Fc/ScFc Chimeric Proteins According to the Invention

A) Transformation of SP2/0, CHO and YB2/0 Cells by Electroporation

The transfection is carried out using the Nucleofector™ electroporation protocol (Lonza). The cells in the exponential phase are centrifuged for 5 min at 300 g and resuspended in PBS. After counting, the required amount is pelleted by centrifugation (300 g, 5 min) and taken up in 100 μl of Nucleofector™ solution V buffer. $2.5 \times 10^6$ SP2/0 cells or $1 \times 10^6$ CHO cells are transfected with 2.5 μg of linearized vector. After electroporation, the cells are put back into complete medium and distributed in 96-well plates at 1000 cells per well for the SP2/0 cells and 100 cells per well for the CHO cells. The optimal clonality conditions were established according to the efficiency of the electroporation program chosen and the nature of the line used. The selection of the clones having stably integrated the expression vector is carried out by adding neomycin (G418) at 1 mg/ml final concentration 24 h after the transfection.

It should be noted that the dimerization of the monomeric SAP-Fc and SAP-ScFc proteins takes place naturally in the transformed cells, as previously mentioned.

After 15-20 days of culture, the supernatants of the G418-resistant clones are removed and then tested by ELISA in order to evaluate the level of production of the recombinant protein (detection of the human Fc). The selected clones are amplified in 24-well plates and then T25 flasks for other ELISA assays and a part is frozen in liquid nitrogen in freezing medium containing 10% of DMSO and 20% of FCS.

Protocol for Assaying SAP-Fc and SAP-ScFc by ELISA:

Firstly, MaxiSorp™ plates (NUNC) are coated with an anti-human IgG primary antibody (1 μg/ml, Beckman Coulter) overnight at 4° C. After 3 washes with PBS/0.05% tween 20, 50 μl of the samples diluted in complete medium are incubated for 2 h at 37° C. At the same time, a standard range of human IgG diluted in complete medium is incubated. After 3 washes, an anti-IgG antibody (Beckman Coulter) coupled to alkaline phosphatase (1 μg/ml) is added and incubated for 1 h 30 at 37° C. After a final series of washing, a volume of 100 μl of the alkaline phosphatase substrate is added and the reaction is then stopped after a few minutes using 3M NaOH. The plate is read by spectrometry at 405 nm.

B) Purification of the SAP-Fc/SAP-ScFc Chimeric Proteins Obtained

B-1) Purification on Protein A

The SAP-Fc/SAP-ScFc chimeric proteins obtained are then purified by affinity chromatography on an ÄKTA$_{FPLC}$ system (GE Healthcare) using protein A affinity columns (Pierce) owing to the strong affinity of protein A for the Fc segments and usable owing to the presence of Fc region fragments in the chimeric proteins according to the invention. The UV detector located downstream of the column makes it possible to monitor the progression; when the absorption of the nonretained phase descends to a threshold value, the protein is eluted with 0.1 M glycine at pH 2.6. The various fractions are collected according to the chromatogram peaks. The eluates obtained are then neutralized with Tris at pH 8.8.

The purified proteins are concentrated by means of Amicon® Ultra4 30 k filters (Millipore), which make it possible to eliminate molecules having a size less than 30 kDa. The solutions are placed in the filters and centrifuged at 4000 g for the time required to obtain the desired volume and the desired concentration.

Figure 6A:
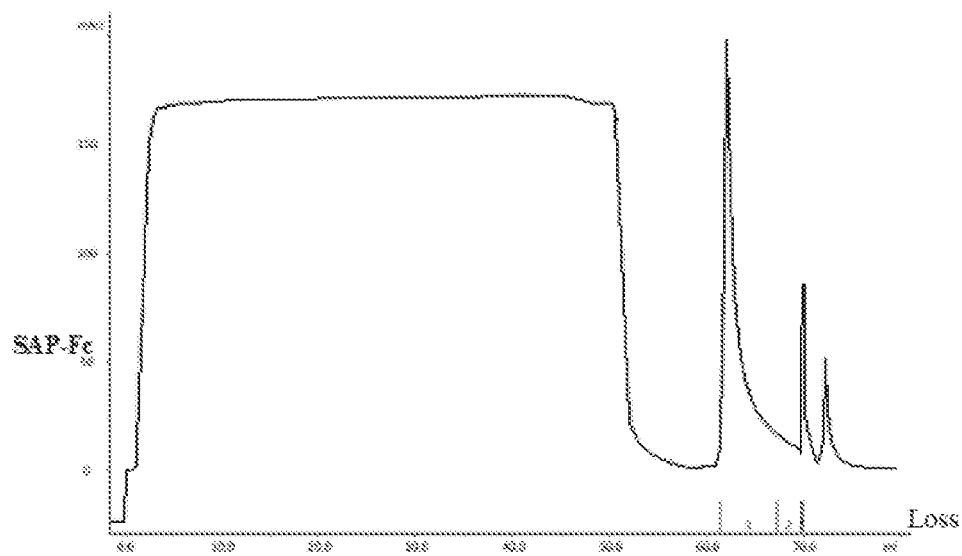
FIGS. 6A and 6B illustrate the results of the purification step on protein A according to the invention considered in example 3 hereinafter, for the dimeric SAP-Fc (FIG. 6A) and monomeric SAP-ScFc (FIG. 6B) chimeric proteins (x-axis: volume injected in ml; y-axis: measurement of optical density at 280 nm in arbitrary units).
Figure 6B:
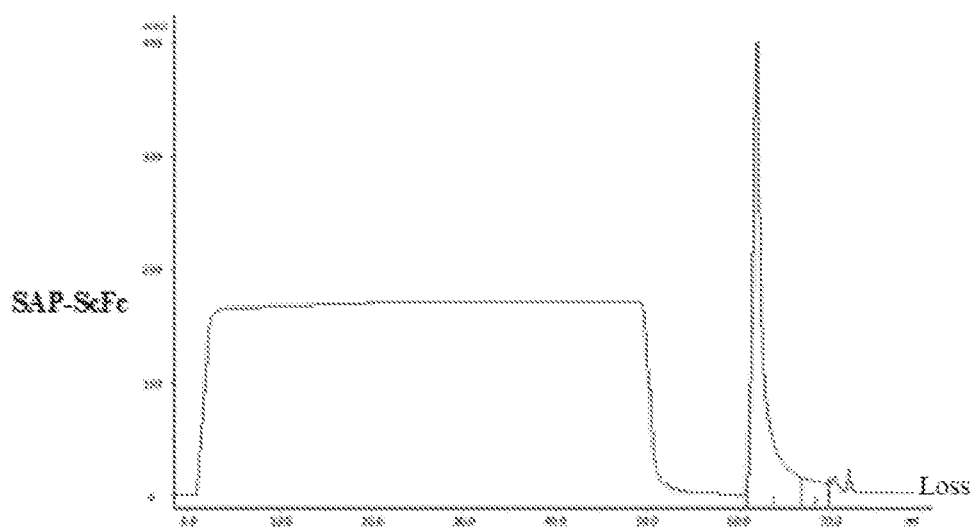

Results:

The results of this step of purification on protein A are illustrated in FIG. 6 hereinafter.

B-2) Detection of the SAP-Fc/SAP-ScFc Chimeric Proteins by Western Blotting Denaturing Gel The purified proteins (or culture supernatants) are mixed with a volume of loading blue containing β-mercaptoethanol (Bio Rad) and boiled for 5 min. They are then migrated by electrophoresis on a polyacrylamide gel (SDS-PAGE) composed of a stacking phase at 7.5% and a separating phase at 10%. The proteins are then transferred onto a PVDF membrane and saturated with 5% milk. They are then incubated for 1 h at ambient temperature in the presence of the mouse anti-SAP (Abcam) or anti-IgG antibody coupled to HRP (Beckman Coulter) (1 µg/ml). The anti-SAP antibody is revealed with a goat anti-mouse IgG secondary antibody coupled to HRP (Santa Cruz) (0.2 µg/ml). The chemiluminescence reaction is triggered by adding the ECL substrate (Pierce) and revealed on an autoradiographic film (Kodak).

Semi-Native Gel

The proteins are mixed with a volume of loading blue without β-mercaptoethanol and then migrated in an SDS-12% PAGE gel. The rest of the protocol is the same as for the denaturing gel.

Figure 7:
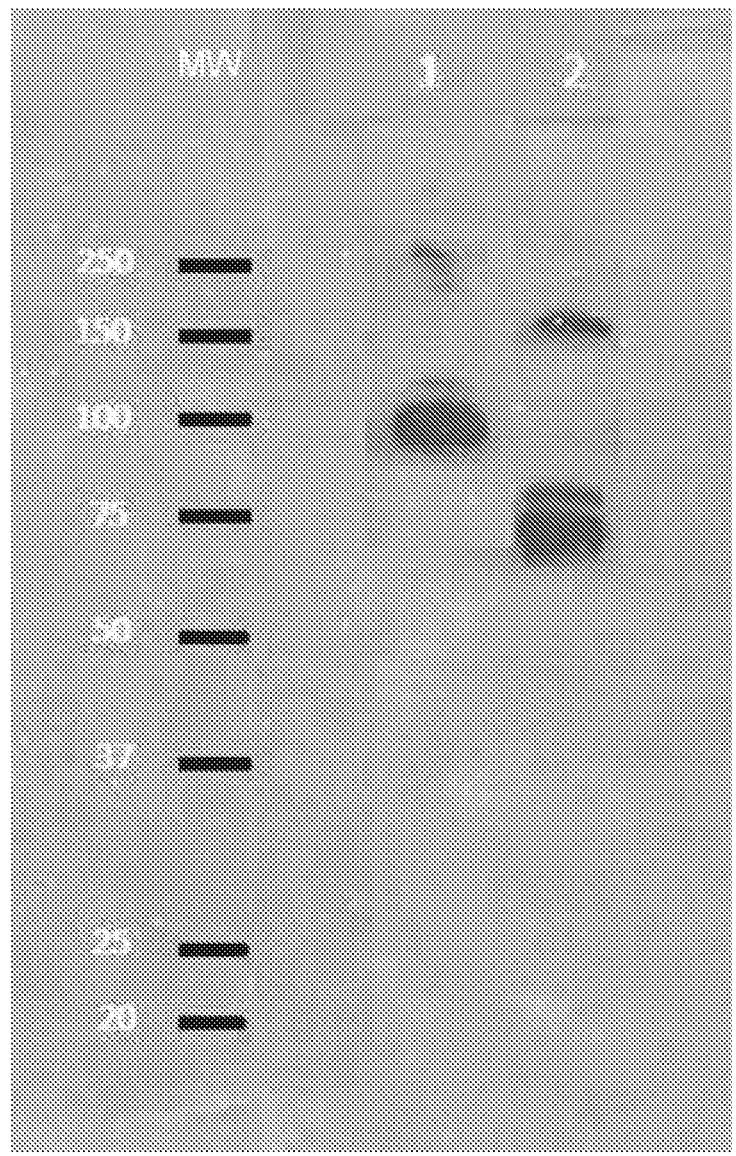
FIG. 7 illustrates the results of the purification step by Western blotting considered in example 3 hereinafter, for the SAP-Fc and SAP-ScFc chimeric proteins. Sample 1: characterizes the SAP-Fc: sample 2: characterizes the SAP-ScFc. The band at 75 kDa corresponds to the monomeric SAP-ScFc architecture. The band at 100 kDa corresponds to the dimeric SAP-Fc architecture.
Figure 8:
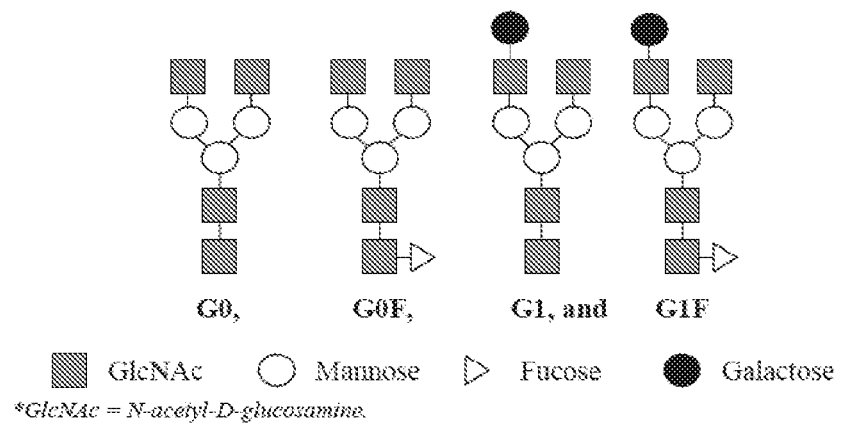
FIG. 8 illustrates the glycan structures that can be considered in the context of the fucosylation of an Fc region of a human antibody.

Results:

The results are illustrated in FIG. 7.

The band at 75 kDa corresponds to the monomeric SAP-ScFc architecture. The band at 100 kDa corresponds to the dimeric SAP-Fc architecture.

Example 4: Recognition of the Amyloid Substance

A) Test for In Vitro Binding of the SAP-Fc/SAP-ScFc Chimeric Proteins on Sections of Human Amyloid Heart The SAP-Fc/ScFc chimeric proteins according to the invention are brought into contact with sections of human amyloid heart, in the presence of calcium and of DNAse I.

The amyloid organs are provided by the reference center for AL amyloidosis and other monoclonal Ig deposit diseases. The organ fragments are fixed on a Cryomatrix™ gel (Thermo Scientific), then cut at −20° C. onto SuperFrost® Plus slides (Thermo Scientific) at a thickness of 8 µm. The slides are stored at −80° C.

The slides are then dried at ambient temperature and then fixed in acetone at −20° C. for 15 min. A treatment with DNAse I (4 U/µl) is carried out at ambient temperature for 15 min, followed by two rapid washes and two washes for 5 min with PBS. The DNAse treatment makes it possible to prevent attachment of the SAP which has a natural affinity for DNA. The primary antibodies, which will serve as a positive control, are then added to the slides at 5 µg/ml in PBS and incubated for 1 h in a humid chamber at 37° C. The SAP-Fc and SAP-ScFc proteins are diluted in PBS (5 µg/ml) containing $CaCl_2$ at 2.2 mM. After washing, the secondary antibodies (rabbit anti-human IgG Fc, Dako or mouse anti-human SAP, Abcam) coupled to fluorochromes and diluted in PBS to 1 µg/ml are added and incubated for 30 min at ambient temperature.

Results:

The results obtained confirm the fact that the SAP-Fc/SAP-ScFc chimeric proteins according to the invention retain their ability to bind to the amyloidosis deposits and do not bind to healthy tissues.

B) Test for In Vivo Binding of the SAP-Fc/SAP-ScFc Chimeric Proteins on a Murine Model of AA Amyloidosis B-1) Preparation of a Murine Model of AA Amyloidosis On D0, a solution comprising I.V 200 µl of AEF (i.e. ground SaM ApoAII amyloidosis spleen material) is injected intravenously and 200 µl of 1% silver nitrate are injected subcutaneously, into a mouse (Balb/c or C57/B16).

On D7 and D14, a solution comprising 100 µl of 1% silver nitrate is injected subcutaneously.

On D21, the animal is sacrificed and the spleen and liver are removed.

Sections of these organs are cut, and staining with Congo red is carried out on said sections in order to recognize the amyloidosis deposits.

Results:

The results obtained characterize without any doubt the presence of amyloidosis deposits on the sections of organs derived from the murine model previously described, said deposits being absent on healthy mice.

B-2) Test for Binding of the SAP-Fc/SAP-ScFc Chimeric Proteins According to the Invention The same murine model of AA amyloidosis as the one described in point B-1) above is considered.

On D21, in place of the sacrifice step, 2 mg of a solution comprising the SAP-Fc or SAP-ScFc chimeric proteins according to the invention or 1 mg of human SAP are intravenously injected. In parallel, other mice are injected with PBS as a control.

On D24, the animal is sacrificed and the spleen and liver are removed.

The slides are prepared as previously described. The amyloid deposits are revealed by staining with Congo red.

The presence of SAP-Fc or SAP-ScFc associated with the amyloid deposits is observed by means of labeling with FITC-coupled anti-human IgG Fc (Dako). When possible, double labeling with the Congo red is carried out in order to be sure of the colocalization of the deposits.

Finally, anti-human SAP labeling was also carried out on certain slides of the various organs/animals.

Results:

The results obtained confirm:
- the presence of characteristic amyloid deposits in the spleen and the liver of the animals where the AA amyloidosis was triggered,
- the capacity of the SAP-Fc/SAP-ScFc chimeric proteins according to the invention to bind to the amyloid deposits (with colocalization on Congo red),
- the specificity of the anti-human Fc IgG labeling (absence of labeling on the mice that were amyloid but injected with human SAP without Fc),
- the specificity of the binding of the SAP-Fc/SAP-ScFc to the amyloid deposits (total absence of labeling on the slides of healthy mice).

Example 5: Evaluation of the In Vivo Therapeutic Efficacy of the SAP-Fc/SAP-ScFc Chimeric Proteins on AA Amyloidosis in Balb/c Mice 1) Materials and Methods The induction of AA amyloidosis in Balb/c mice is carried out according to the protocol defined in FIG. 9 hereinafter.

Figure 9:
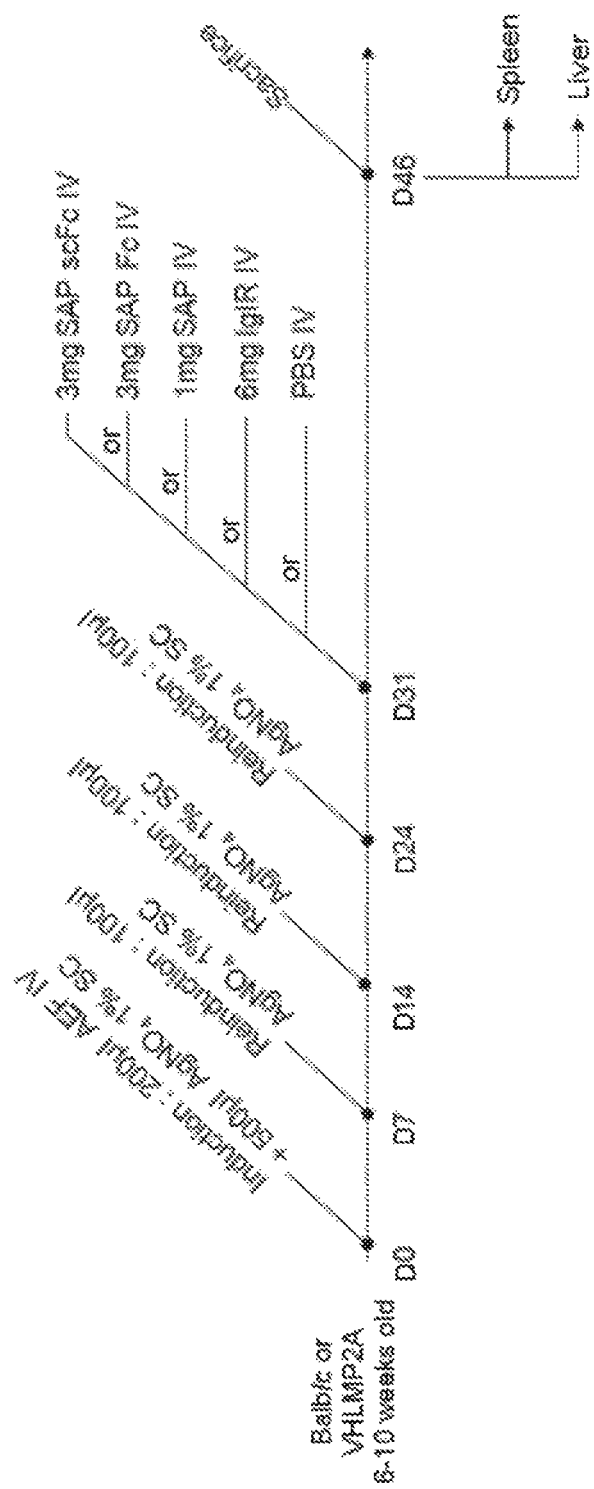
FIG. 9 illustrates the protocol for inducing AA amyloidosis in Balb/c and VH-LMP2A mice. In this FIG. 9, AEF IV="Amyloid Enhancing Factor" given Intravenously; SC="Subcutaneous"; IgIR="Immunoglobulin Irrelevant anti-FVIII" (human IgG1).

As emerges from this FIG. 9, various compounds are tested. Each time, the compound tested is injected into the Balb/c mice one week after the final injection of $AgNO_4$.

The compounds tested are an SAP-ScFc chimeric protein according to the invention (3 mg), an SAP-Fc chimeric protein according to the invention (3 mg), an anti-FVIII irrelevant IgG1 immunoglobulin ("IgIR", isotype control) (6 mg) or else PBS buffer (negative control).

Sections of the organs from the mice described above, in particular the spleen, are cut, and staining with Congo red is carried out on said sections in order to recognize the deposits of amyloidosis, so as to quantify said deposits.

Figure 10:
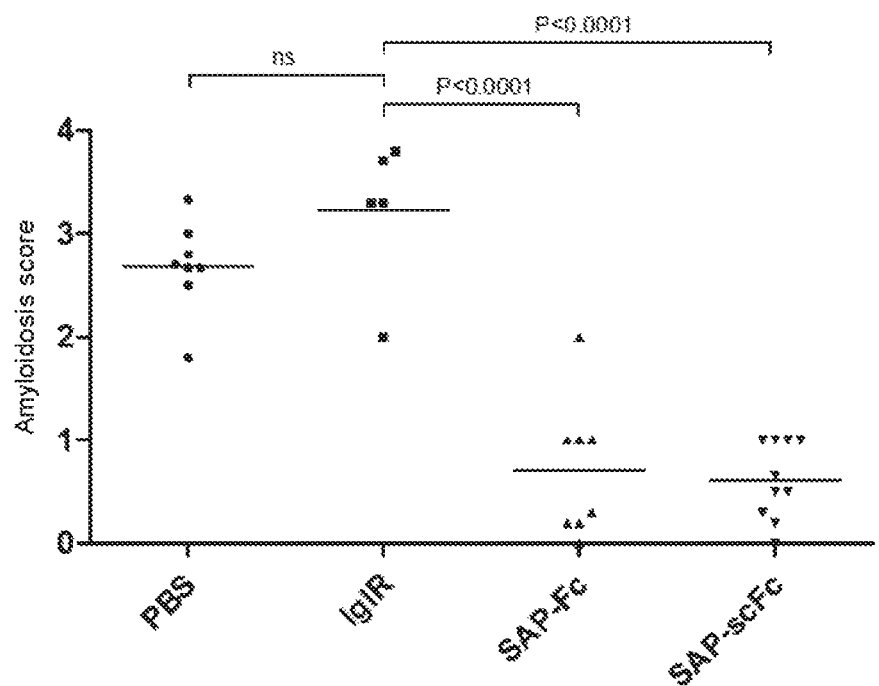
FIG. 10 illustrates the effect of various compounds, including the SAP-Fc and SAP-ScFc chimeric proteins according to the invention, on the amyloidosis deposits induced in Balb/c mice treated according to the protocol detailed in FIG. 9.

2) Results:

As emerges from FIG. 10, the amyloidosis deposits are significantly weaker in the Balb/c mice treated with SAP-Fc or SAP-ScFc.

The results obtained therefore confirm the capacity of the SAP-Fc/SAP-ScFc chimeric proteins according to the invention:
- to bind to the amyloid deposits, and
- to eliminate the AA amyloidosis deposits.

The results obtained also attest that it is indeed the SAP fragment present in the chimeric proteins according to the invention which allows them to actually bind to the amyloid deposits. This emerges from the inability of the IgIR compound to bind to the amyloid deposits. Indeed, this IgIR compound admittedly comprises at least one fragment of an Fc region of a human antibody similar to that present in the chimeric proteins according to the invention, but it is on the other hand devoid of the SAP fragment.

Example 6: Other Evaluation of the In Vivo Therapeutic Efficacy of the SAP-Fc/SAP-ScFc Chimeric Proteins on AA Amyloidosis in VH-LMP2A Mice 1) Materials and Methods The induction of AA amyloidosis in VH-LMP2A mice is carried out according to the protocol defined in FIG. 9 above.

The compounds tested are a chimeric protein according to the invention (SAP-ScFc), an SAP protein as such (i.e. devoid of the fragment of an Fc region of a human antibody), or else PBS buffer.

The VH-LMP2A mice have the particularity of being devoid of the ability to produce antibodies. In fact, a decrease in the amyloidosis deposits subsequent to the injection of a specific compound will reflect said specific compound's own capacity to effectively recruit the effector cells, in particular the neutrophil polymorphonuclear cells and the monocyte-macrophages, involved in the elimination of the amyloid deposits.

Sections of the organs from the mice described above, in particular the spleen, are cut, and staining with Congo red is carried out on said sections in order to recognize the amyloidosis deposits, so as to quantify said deposits.

Figure 11:
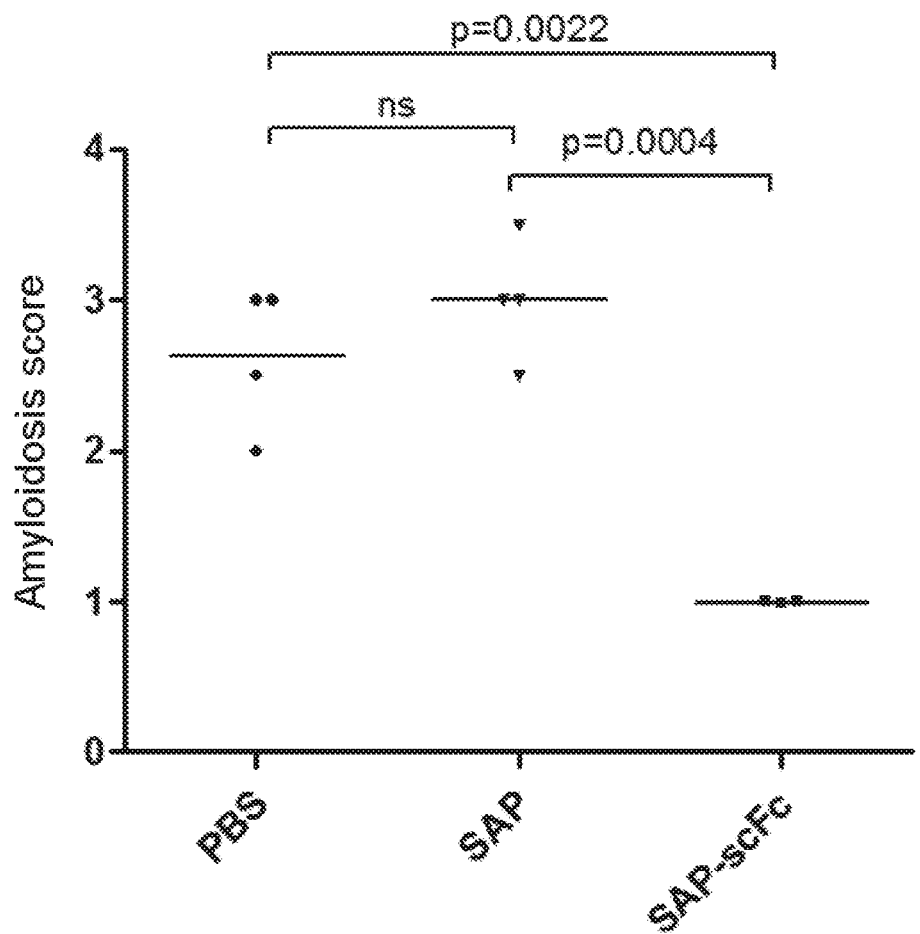
FIG. 11 illustrates the effect of various compounds, including the SAP-ScFc chimeric proteins according to the invention, on the amyloidosis deposits induced in VH-LMP2A mice treated according to the protocol detailed in FIG. 9.

2) Results:

As emerges from FIG. 11, the amyloidosis deposits are significantly reduced in the VH-LMP2A mice treated with the SAP-ScFc chimeric proteins according to the invention.

On the other hand, as emerges from FIG. 11, no decrease in the amyloidosis deposits is observed in the case of the SAP protein as such, i.e. devoid of the fragment of an Fc region of a human antibody.

The results obtained therefore confirm the capacity of the SAP-Fc/SAP-ScFc chimeric proteins according to the invention:
- to bind to the amyloid deposits, and
- to eliminate the AA amyloidosis deposits, and therefore to effectively recruit the effector cells, in particular the neutrophil polymorphonuclear cells and the monocyte-macrophages, involved in the elimination of these amyloid deposits.

The results obtained also attest that it is indeed the fragment of an Fc region of a human antibody present in the chimeric proteins according to the invention which enables this effective recruitment of the effector cells.

SEQUENCES:

```
SEQ ID NO: 1: (Protein = human SAP)
HTDLSGKVFVFPRESVTDHVNLITPLEKPLQNFTLCFRAYSDLSRAYSL

FSYNTQGRDNELLVYKERVGEYSLYIGRHKVTSKVIEKFPAPVHICVSWESSSGIAE

FWINGTPLVKKGLRQGYFVEAQPKIVLGQEQDSYGGKFDRSQSFVGEIGDLYMW

DSVLPPENILSAYQGTPLPANILDWQALNYEIRGYVIIKPLVWV

SEQ ID NO: 2: (DNA = human SAP)
CACACAGACCTCAGTGGGAAGGTGTTTGTATTTCCTAGAGAATCTGT

TACTGATCATGTAAACTTGATCACACCGCTGGAGAAGCCTCTACAGAACTTTA

CCTTGTGTTTTCGAGCCTATAGTGATCTCTCTCGTGCCTACAGCCTCTTCTCCTA

CAATACCCAAGGCAGGGATAATGAGCTACTAGTTTATAAAGAAAGAGTTGGA

GAGTATAGTCTATACATTGGAAGACACAAAGTTACATCCAAAGTTATCGAAAA

GTTCCCGGCTCCAGTGCACATCTGTGTGAGCTGGGAGTCCTCATCAGGTATTGC

TGAATTTTGGATCAATGGGACACCTTTGGTGAAAAAGGGTCTGCGACAGGGTT

ACTTTGTGGAAGCTCAGCCCAAGATTGTCCTGGGGCAGGAACAGGATTCCTAT

GGGGGCAAGTTTGATAGGAGCCAGTCCTTTGTGGGAGAGATTGGGGATTTGTA

CATGTGGGACTCTGTGCTGCCCCCAGAAAATATCCTGTCTGCCTATCAGGGTAC

CCCTCTCCCTGCCAATATCCTGGACTGGCAGGCTCTGAACTATGAAATCAGAG

GATATGTCATCATCAAACCCTTGGTGTGGGTC
```

SEQ ID NO: 3: (Protein = fragment of an Fc region of a human antibody)
APELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQKSLS

LSPGK

SEQ ID NO: 4: (DNA = fragment of an Fc region of a human antibody)
GCACCTGAACTCCTGGGGGACCGTCAGTCTTCCTCTTCCCCCCAAA

ACCCAAGGACACCCTCATGATCTCCCGGACCCCTGAGGTCACATGCGTGGTGG

TGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCT

GCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAG

CCGGAGAACAACTACAAGACCACGCCTCCCGTGCTGGACTCCGACGGCTCCTT

CTTCCTCTACAGCAAGCTCACCGTGGACAAGAGCAGGTGGCAGCAGGGGAAC

GTCTTCTCATGCTCCGTGATGCATGAGGCTCTGCACAACCACTACACGCAGAA

GAGCCTCTCCCTGTCTCCGGGTAAATGA

SEQ ID NO: 5: (Protein = Non-structuring peptide sequence between SAP and a
hinge region, or spacer chain between two fragments of an Fc region at the level
of SAP-ScFc)
(GGGGS)n, with n between 1 and 5

SEQ ID NO: 6: (DNA = Non-structuring peptide sequence between SAP and a hinge
region, or spacer chain between two fragments of an Fc region at the level of
characterizes SAP-ScFc)
(CTTGGTGGAGGCGGTTCAGGCGGAGGTGGCTCTGGCGGTGGCG)m,
with m between 1 and 5

SEQ ID NO: 7: (Protein = Secreted monomeric SAP-Fc)
HTDLSGKVFVFPRESVTDHVNLITPLEKPLQNFTLCFRAYSDLSRAYSL

FSYNTQGRDNELLVYKERVGEYSLYIGRHKVTSKVIEKFPAPVHICVSWESSSGIAE

FWINGTPLVKKGLRQGYFVEAQPKIVLGQEQDSYGGKFDRSQSFVGEIGDLYMW

DSVLPPENILSAYQGTPLPANILDWQALNYEIRGYVIIKPLVWVEPKSCDKTHTCPP

CPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSLSPGK

SEQ ID NO: 8: (DNA = Secreted monomeric SAP-Fc)
CACACAGACCTCAGTGGGAAGGTGTTTGTATTTCCTAGAGAATCTGT

TACTGATCATGTAAACTTGATCACACCGCTGGAGAAGCCTCTACAGAACTTTA

CCTTGTGTTTTCGAGCCTATAGTGATCTCTCTCGTGCCTACAGCCTCTTCTCCTA

CAATACCCAAGGCAGGGATAATGAGCTACTAGTTTATAAAGAAAGAGTTGGA

GAGTATAGTCTATACATTGGAAGACACAAAGTTACATCCAAAGTTATCGAAAA

GTTCCCGGCTCCAGTGCACATCTGTGTGAGCTGGGAGTCCTCATCAGGTATTGC

TGAATTTTGGATCAATGGGACACCTTTGGTGAAAAAGGGTCTGCGACAGGGTT

```
ACTTTGTGGAAGCTCAGCCCAAGATTGTCCTGGGGCAGGAACAGGATTCCTAT

GGGGGCAAGTTTGATAGGAGCCAGTCCTTTGTGGGAGAGATTGGGGATTTGTA

CATGTGGGACTCTGTGCTGCCCCCAGAAAATATCCTGTCTGCCTATCAGGGTAC

CCCTCTCCCTGCCAATATCCTGGACTGGCAGGCTCTGAACTATGAAATCAGAG

GATATGTCATCATCAAACCCTTGGTGTGGGTCGAGCCCAAATCTTGTGACAAA

ACTCACACATGCCCACCGTGCCCAGCACCTGAACTCCTGGGGGGACCGTCAGT

CTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGA

GGAGCAGTACAACAGCACGTACCGTGTGGTCAGCGTCCTCACCGTCCTGCACC

AGGACTGGCTGAATGGCAAGGAGTACAAGTGCAAGGTCTCCAACAAAGCCCT

CCCAGCCCCCATCGAGAAAACCATCTCCAAAGCCAAAGGGCAGCCCCGAGAA

CCACAGGTGTACACCCTGCCCCCATCCCGGGAGGAGATGACCAAGAACCAGGT

CAGCCTGACCTGCCTGGTCAAAGGCTTCTATCCCAGCGACATCGCCGTGGAGT

GGGAGAGCAATGGGCAGCCGGAGAACAACTACAAGACCACGCCTCCCGTGCT

GGACTCCGACGGCTCCTTCTTCCTCTACAGCAAGCTCACCGTGGACAAGAGCA

GGTGGCAGCAGGGGAACGTCTTCTCATGCTCCGTGATGCATGAGGCTCTGCAC

AACCACTACACGCAGAAGAGCCTCTCCCTGTCTCCGGGTAAATGA

SEQ ID NO: 9: (Protein = Secreted monomeric SAP-ScFc)
HTDLSGKVFVFPRESVTDHVNLITPLEKPLQNFTLCFRAYSDLSRAYSL

FSYNTQGRDNELLVYKERVGEYSLYIGRHKVTSKVIEKFPAPVHICVSWESSSGIAE

FWINGTPLVKKGLRQGYFVEAQPKIVLGQEQDSYGGKFDRSQSFVGEIGDLYMW

DSVLPPENILSAYQGTPLPANILDWQALNYEIRGYVIIKPLVWVEPKSCDKTHTCPP

CPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSLSPGKL

GGGGSGGGGSGGGGSEPKSCDKTHTCPPCPAPELLGGPSVFLFPPKPKDTLMISRT

PEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKSRWQQG

NVFSCSVMHEALHNHYTQKSLSLSPGK

SEQ ID NO: 10: (DNA = Secreted monomeric SAP-ScFc)
CACACAGACCTCAGTGGGAAGGTGTTTGTATTTCCTAGAGAATCTGT

TACTGATCATGTAAACTTGATCACACCGCTGGAGAAGCCTCTACAGAACTTTA

CCTTGTGTTTTCGAGCCTATAGTGATCTCTCGTGCCTACAGCCTCTTCTCCTA

CAATACCCAAGGCAGGGATAATGAGCTACTAGTTTATAAAGAAAGAGTTGGA

GAGTATAGTCTATACATTGGAAGACACAAAGTTACATCCAAAGTTATCGAAAA

GTTCCCGGCTCCAGTGCACATCTGTGTGAGCTGGGAGTCCTCATCAGGTATTGC

TGAATTTTGGATCAATGGGACACCTTTGGTGAAAAAGGGTCTGCGACAGGGTT

ACTTTGTGGAAGCTCAGCCCAAGATTGTCCTGGGGCAGGAACAGGATTCCTAT

GGGGGCAAGTTTGATAGGAGCCAGTCCTTTGTGGGAGAGATTGGGGATTTGTA
```

-continued

```
CATGTGGGACTCTGTGCTGCCCCCAGAAAATATCCTGTCTGCCTATCAGGGTAC

CCCTCTCCCTGCCAATATCCTGGACTGGCAGGCTCTGAACTATGAAATCAGAG

GATATGTCATCATCAAACCCTTGGTGTGGGTCGAGCCCAAATCTTGTGACAAA

ACTCACACATGCCCACCGTGCCCAGCACCTGAACTCCTGGGGGGACCGTCAGT

CTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGA

GGAGCAGTACAACAGCACGTACCGTGTGGTCAGCGTCCTCACCGTCCTGCACC

AGGACTGGCTGAATGGCAAGGAGTACAAGTGCAAGGTCTCCAACAAAGCCCT

CCCAGCCCCCATCGAGAAAACCATCTCCAAAGCCAAAGGGCAGCCCCGAGAA

CCACAGGTGTACACCCTGCCCCCATCCCGGGAGGAGATGACCAAGAACCAGGT

CAGCCTGACCTGCCTGGTCAAAGGCTTCTATCCCAGCGACATCGCCGTGGAGT

GGGAGAGCAATGGGCAGCCGGAGAACAACTACAAGACCACGCCTCCCGTGCT

GGACTCCGACGGCTCCTTCTTCCTCTATAGCAAGCTCACCGTGGACAAGAGCA

GGTGGCAGCAGGGGAACGTCTTCTCATGCTCCGTGATGCATGAGGCTCTGCAC

AACCACTACACGCAGAAGAGCCTCTCCCTGTCTCCGGGTAAGCTTGGTGGAGG

CGGTTCAGGCGGAGGTGGCTCTGGCGGTGGCGGATCTGAGCCCAAATCTTGTG

ACAAAACTCACACATGCCCACCGTGCCCAGCACCTGAACTCCTGGGGGGACCG

TCAGTCTTCCTCTTCCCCCCAAAACCCAAGGACACCCTCATGATCTCCCGGACC

CCTGAGGTCACATGCGTGGTGGTGGACGTGAGCCACGAAGACCCTGAGGTCAA

GTTCAACTGGTACGTGGACGGCGTGGAGGTGCATAATGCCAAGACAAAGCCGC

GGGAGGAGCAGTACAACAGCACGTACCGTGTGGTCAGCGTCCTCACCGTCCTG

CACCAGGACTGGCTGAATGGCAAGGAGTACAAGTGCAAGGTCTCCAACAAAG

CCCTCCCAGCCCCCATCGAGAAAACCATCTCCAAAGCCAAAGGGCAGCCCCGA

GAACCACAGGTGTACACCCTGCCCCCATCCCGGGAGGAGATGACCAAGAACC

AGGTCAGCCTGACCTGCCTGGTCAAAGGCTTCTATCCCAGCGACATCGCCGTG

GAGTGGGAGAGCAATGGGCAGCCGGAGAACAACTACAAGACCACGCCTCCCG

TGCTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGCTCT

GCACAACCACTACACGCAGAAGAGCCTCTCCCTGTCTCCGGGTAAATGA
```

SEQ ID NO: 11: (Protein = hinge region + two fragments of an Fc region of a human antibody, bonded to each other by a bond (spacer chain + hinge region) of SAP-ScFc)

```
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFSCSVMH

EALHNHYTQKSLSLSPGKLGGGSGGGGSGGGGSEPKSCDKTHTCPPCPAPELLG

GPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK
```

SEQ ID NO: 12: (DNA = hinge region + two fragments of an Fc region of a human antibody, bonded to each other by a bond (spacer chain + hinge region) of SAP-ScFc)
GAGCCCAAATCTTGTGACAAAACTCACACATGCCCACCGTGCCCAG

CACCTGAACTCCTGGGGGACCGTCAGTCTTCCTCTTCCCCCCAAAACCCAAG

GACACCCTCATGATCTCCCGGACCCCTGAGGTCACATGCGTGGTGGTGGACGT

GAGCCACGAAGACCCTGAGGTCAAGTTCAACTGGTACGTGGACGGCGTGGAG

GTGCATAATGCCAAGACAAAGCCGCGGGAGGAGCAGTACAACAGCACGTACC

GTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCAT

CTCCAAAGCCAAAGGGCAGCCCCGAGAACCACAGGTGTACACCCTGCCCCCAT

CCCGGGAGGAGATGACCAAGAACCAGGTCAGCCTGACCTGCCTGGTCAAAGG

CTTCTATCCCAGCGACATCGCCGTGGAGTGGGAGAGCAATGGGCAGCCGGAGA

ACAACTACAAGACCACGCCTCCCGTGCTGGACTCCGACGGCTCCTTCTTCCTCT

ATAGCAAGCTCACCGTGGACAAGAGCAGGTGGCAGCAGGGGAACGTCTTCTC

ATGCTCCGTGATGCATGAGGCTCTGCACAACCACTACACGCAGAAGAGCCTCT

CCCTGTCTCCGGGTAAGCTTGGTGGAGGCGGTTCAGGCGGAGGTGGCTCTGGC

GGTGGCGGATCTGAGCCCAAATCTTGTGACAAAACTCACACATGCCCACCGTG

CCCAGCACCTGAACTCCTGGGGGACCGTCAGTCTTCCTCTTCCCCCCAAAACC

CAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTG

GAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAAAC

CATCTCCAAAGCCAAAGGGCAGCCCCGAGAACCACAGGTGTACACCCTGCCCC

CATCCCGGGAGGAGATGACCAAGAACCAGGTCAGCCTGACCTGCCTGGTCAA

AGGCTTCTATCCCAGCGACATCGCCGTGGAGTGGGAGAGCAATGGGCAGCCGG

AGAACAACTACAAGACCACGCCTCCCGTGCTGGACTCCGACGGCTCCTTCTTC

CTCTACAGCAAGCTCACCGTGGACAAGAGCAGGTGGCAGCAGGGGAACGTCTT

CTCATGCTCCGTGATGCATGAGGCTCTGCACAACCACTACACGCAGAAGAGCC

TCTCCCTGTCTCCGGGTAAATGA

SEQ ID NO: 13: (Protein = Human IgG1 hinge region)
EPKSCDKTHTCPPCP

SEQ ID NO: 14: (DNA = Human IgG1 hinge region)
CTCACACATGCCCACCGTGCCCA

SEQ ID NO: 15: (Protein = Human IgG2 hinge region)
ERKCCVECPPCP

SEQ ID NO: 16: (Protein = Human IgG3 hinge region)
ELKTPLGDTTHTCPRCP

SEQ ID NO: 17: (Protein = Human IgG3 hinge region)
EPKSCDTPPPCPRCP

SEQ ID NO: 18: (Protein = Human IgG4 hinge region)
ESKYGPPCPSCP

SEQ ID NO: 19: (Protein = Shortened IgG1 hinge region (SEQ ID NO: 13))
DKTHTCPPCP -continued SEQ ID NO: 20: (Protein = Natural signal peptide of SAP)
MNKPLLWISVLTSLLEAFA SEQ ID NO: 21: (DNA = Natural signal peptide of SAP)
ATGAACAAGCCGCTCCTTTGGATCTCTGTCCTCACCAGCCTCCTGGA
AGCCTTTGCT SEQ ID NO: 22: (Protein = MMP1 human TIMP signal peptide (= uniprot
P01033))
MAPPEPLASGILLLLWLIAPSRA SEQ ID NO: 23: (Protein = Human insulin signal peptide (= uniprot
P01308))
MALWMRLLPLLALLALWGPDPAAA SEQ ID NO: 24: (Protein = Human EPO signal peptide (= uniprot P01588))
MGVHECPAWLWLLLSLLSLPLGLPVLG SEQ ID NO: 25: (Protein = MB7 signal peptide derived from
WO 2011/114063)
MRWSWIFLLLLSITSANA SEQ ID NO: 26: (Protein = AMHRII signal peptide derived from
WO 2011/114063)
MRWSWIFLFLLSITASVHC SEQ ID NO: 27: (Protein = XXII49 signal peptide derived from
WO 2011/114063)
MAWVWTLLFLMAAAQSAQA SEQ ID NO: 28: (DNA = SAP from example 1)
GTCGACACCATGAACAAGCCGCTCTTTGGATCTCTGTCCTCACCAGC

CTCCTGGAAGCCTTTGCTCACACAGACCTCAGTGGGAAGGTGTTTGTATTTCCT

AGAGAATCTGTTACTGATCATGTAAACTTGATCACACCGCTGGAGAAGCCTCT

ACAGAACTTTACCTTGTGTTTTCGAGCCTATAGTGATCTCTCTCGTGCCTACAG

CCTCTTCTCCTACAATACCCAAGGCAGGGATAATGAGCTACTAGTTTATAAAG

AAAGAGTTGGAGAGTATAGTCTATACATTGGAAGACACAAAGTTACATCCAAA

GTTATCGAAAAGTTCCCGGCTCCAGTGCACATCTGTGTGAGCTGGGAGTCCTC

ATCAGGTATTGCTGAATTTTGGATCAATGGGACACCTTTGGTGAAAAAGGGTC

TGCGACAGGGTTACTTTGTGGAAGCTCAGCCCAAGATTGTCCTGGGGCAGGAA

CAGGATTCCTATGGGGGCAAGTTTGATAGGAGCCAGTCCTTTGTGGGAGAGAT

TGGGGATTTGTACATGTGGGACTCTGTGCTGCCCCCAGAAAATATCCTGTCTGC

CTATCAGGGTACCCCTCTCCCTGCCAATATCCTGGACTGGCAGGCTCTGAACTA

TGAAATCAGAGGATATGTCATCATCAAACCCTTGGTGTGGGTCGAC

SEQ ID NO: 29: (DNA = fragment of an Fc region of a human antibody
from example 1)
ATACTCTCGAGCCCAAATCTTGTGACAAAACTCACACATGCCCACC

GTGCCCAGCACCTGAACTCCTGGGGGGACCGTCAGTCTTCCTCTTCCCCCCAAA

ACCCAAGGACACCCTCATGATCTCCCGGACCCCTGAGGTCACATGCGTGGTGG

TGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCT

GCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAG

CCGGAGAACAACTACAAGACCACGCCTCCCGTGCTGGACTCCGACGGCTCCTT

-continued

CTTCCTCTACAGCAAGCTCACCGTGGACAAGAGCAGGTGGCAGCAGGGGAAC

GTCTTCTCATGCTCCGTGATGCATGAGGCTCTGCACAACCACTACACGCAGAA

GAGCCTCTCCCTGTCTCCGGGTAAATGAGTGCTCCGGACAGAT

SEQ ID NO: 30: (DNA = Monomeric SAP-Fc from example 1)
ATGAACAAGCCGCTCCTTTGGATCTCTGTCCTCACCAGCCTCCTGGA

AGCCTTTGCTCACACAGACCTCAGTGGGAAGGTGTTTGTATTTCCTAGAGAATC

TGTTACTGATCATGTAAACTTGATCACACCGCTGGAGAAGCCTCTACAGAACTT

TACCTTGTGTTTTCGAGCCTATAGTGATCTCTCTCGTGCCTACAGCCTCTTCTCC

TACAATACCCAAGGCAGGGATAATGAGCTACTAGTTTATAAAGAAAGAGTTGG

AGAGTATAGTCTATACATTGGAAGACACAAAGTTACATCCAAAGTTATCGAAA

AGTTCCCGGCTCCAGTGCACATCTGTGTGAGCTGGGAGTCCTCATCAGGTATTG

CTGAATTTTGGATCAATGGGACACCTTTGGTGAAAAAGGGTCTGCGACAGGGT

TACTTTGTGGAAGCTCAGCCCAAGATTGTCCTGGGGCAGGAACAGGATTCCTA

TGGGGGCAAGTTTGATAGGAGCCAGTCCTTTGTGGGAGAGATTGGGGATTTGT

ACATGTGGGACTCTGTGCTGCCCCAGAAAATATCCTGTCTGCCTATCAGGGTA

CCCCTCTCCCTGCCAATATCCTGGACTGGCAGGCTCTGAACTATGAAATCAGA

GGATATGTCATCATCAAACCCTTGGTGTGGGTCGAGCCCAAATCTTGTGACAA

AACTCACACATGCCCACCGTGCCCAGCACCTGAACTCCTGGGGGGACCGTCAG

TCTTCCTCTTCCCCCCAAAACCCAAGGACACCCTCATGATCTCCCGGACCCCTG

AGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGG

AGGAGCAGTACAACAGCACGTACCGTGTGGTCAGCGTCCTCACCGTCCTGCAC

CAGGACTGGCTGAATGGCAAGGAGTACAAGTGCAAGGTCTCCAACAAAGCCC

TCCCAGCCCCCATCGAGAAAACCATCTCCAAAGCCAAAGGGCAGCCCCGAGA

ACCACAGGTGTACACCCTGCCCCCATCCCGGGAGGAGATGACCAAGAACCAG

GTCAGCCTGACCTGCCTGGTCAAAGGCTTCTATCCCAGCGACATCGCCGTGGA

GTGGGAGAGCAATGGGCAGCCGGAGAACAACTACAAGACCACGCCTCCCGTG

CTGGACTCCGACGGCTCCTTCTTCCTCTACAGCAAGCTCACCGTGGACAAGAG

CAGGTGGCAGCAGGGGAACGTCTTCTCATGCTCCGTGATGCATGAGGCTCTGC

ACAACCACTACACGCAGAAGAGCCTCTCCCTGTCTCCGGGTAAATGA

SEQ ID NO: 31: (Protein = Monomeric SAP-Fc from example 1)
MNKPLLWISVLTSLLEAFAHTDLSGKVFVFPRESVTDHVNLITPLEKPL

QNFTLCFRAYSDLSRAYSLFSYNTQGRDNELLVYKERVGEYSLYIGRHKVTSKVIE

KFPAPVHICVSWESSSGIAEFWINGTPLVKKGLRQGYFVEAQPKIVLGQEQDSYGG

KFDRSQSFVGEIGDLYMWDSVLPPENILSAYQGTPLPANILDWQALNYEIRGYVIIK

PLVWVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSCSVMHE

ALHNHYTQKSLSLSPGK-

SEQ ID NO: 32: (DNA = First fragment of an Fc region of a human
antibody from example 2)
GCACCTGAACTCCTGGGGGACCGTCAGTCTTCCTCTTCCCCCCAAA

ACCCAAGGACACCCTCATGATCTCCCGGACCCCTGAGGTCACATGCGTGGTGG

TGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCT

GCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAG

CCGGAGAACAACTACAAGACCACGCCTCCCGTGCTGGACTCCGACGGCTCCTT

CTTCCTCTATAGCAAGCTCACCGTGGACAAGAGCAGGTGGCAGCAGGGGAACG

TCTTCTCATGCTCCGTGATGCATGAGGCTCTGCACAACCACTACACGCAGAAG

AGCCTCTCCCTGTCTCCGGGTAAGCTT

SEQ ID NO: 33: (DNA = Second fragment of an Fc region of a human
antibody from example 2)
AGATCTGAGCCCAAATCTTGTGACAAAACTCACACATGCCCACCGTGCCCA

GCACCTGAACTCCTGGGGGACCGTCAGTCTTCCTCTTCCCCCCAAAACCCAA

GGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAG

GTGCATAATGCCAAGACAAAGCCGCGGGAGGAGCAGTACAACAGCACGTACC

GTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCAT

CTCCAAAGCCAAAGGGCAGCCCCGAGAACCACAGGTGTACACCCTGCCCCCAT

CCCGGGAGGAGATGACCAAGAACCAGGTCAGCCTGACCTGCCTGGTCAAAGG

CTTCTATCCCAGCGACATCGCCGTGGAGTGGGAGAGCAATGGGCAGCCGGAGA

ACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTC

ATGCTCCGTGATGCATGAGGCTCTGCACAACCACTACACGCAGAAGAGCCTCT

CCCTGTCTCCGGGTAAATGAGTGCTCCGGA

SEQ ID NO: 34: (DNA = Spacer chain between the first and second
fragments of an Fc region of a human antibody from example 2)
AAGCTTGGTGGAGGCGGTTCAGGCGGAGGTGGCTCTGGCGGTGGCG
GATCC SEQ ID NO: 35: (DNA = Monomeric SAP-ScFc from example 2)
ATGAACAAGCCGCTCCTTTGGATCTCTGTCCTCACCAGCCTCCTGGA
AGCCTTTGCTCACACAGACCTCAGTGGGAAGGTGTTTGTATTCCTAGAGAATC
TGTTACTGATCATGTAAACTTGATCACACCGCTGGAGAAGCCTCTACAGAACTT
TACCTTGTGTTTTCGAGCCTATAGTGATCTCTCGTGCCTACAGCCTCTTCTCC
TACAATACCCAAGGCAGGGATAATGAGCTACTAGTTTATAAAGAAAGAGTTGG
AGAGTATAGTCTATACATTGGAAGACACAAAGTTACATCCAAAGTTATCGAAA
AGTTCCCGGCTCCAGTGCACATCTGTGTGAGCTGGGAGTCCTCATCAGGTATTG
CTGAATTTTGGATCAATGGGACACCTTTGGTGAAAAAGGGTCTGCGACAGGGT
TACTTTGTGGAAGCTCAGCCCAAGATTGTCCTGGGGCAGGAACAGGATTCCTA
TGGGGGCAAGTTTGATAGGAGCCAGTCCTTTGTGGGAGAGATTGGGGATTTGT
ACATGTGGGACTCTGTGCTGCCCCAGAAAATATCCTGTCTGCCTATCAGGGTA
CCCCTCTCCCTGCCAATATCCTGGACTGGCAGGCTCTGAACTATGAAATCAGA
GGATATGTCATCATCAAACCCTTGGTGTGGGTCGAGCCCAAATCTTGTGACAA
AACTCACACATGCCCACCGTGCCCAGCACCTGAACTCCTGGGGGACCGTCAG
TCTTCCTCTTCCCCCCAAAACCCAAGGACACCCTCATGATCTCCCGGACCCCTG
AGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGG

```
                              -continued
AGGAGCAGTACAACAGCACGTACCGTGTGGTCAGCGTCCTCACCGTCCTGCAC
CAGGACTGGCTGAATGGCAAGGAGTACAAGTGCAAGGTCTCCAACAAAGCCC
TCCCAGCCCCCATCGAGAAAACCATCTCCAAAGCCAAAGGGCAGCCCCGAGA
ACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGA
GTGGGAGAGCAATGGGCAGCCGGAGAACAACTACAAGACCACGCCTCCCGTG
CTGGACTCCGACGGCTCCTTCTTCCTCTATAGCAAGCTCACCGTGGACAAGAG
CAGGTGGCAGCAGGGGAACGTCTTCTCATGCTCCGTGATGCATGAGGCTCTGC
ACAACCACTACACGCAGAAGAGCCTCTCCCTGTCTCCGGGTAAGCTTGGTGGA
GGCGGTTCAGGCGGAGGTGGCTCTGGCGGTGGCGGATCTGAGCCCAAATCTTG
TGACAAAACTCACACATGCCCACCGTGCCCAGCACCTGAACTCCTGGGGGGAC
CGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTC
AAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTC
CTGCACCAGGACTGGCTGAATGGCAAGGAGTACAAGTGCAAGGTCTCCAACA
AAGCCCTCCCAGCCCCCATCGAGAAAACCATCTCCAAAGCCAAAGGGCAGCCC
CGAGAACCACAGGTGTACACCCTGCCCCCATCCCGGGAGGAGATGACCAAGA
ACCAGGTCAGCCTGACCTGCCTGGTCAAAGGCTTCTATCCCAGCGACATCGCC
GTGGAGTGGGAGAGCAATGGGCAGCCGGAGAACAACTACAAGACCACGCCTC
CCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAATGA SEQ ID NO: 36: (Protein = Monomeric SAP-ScFc from example 2)
MNKPLLWISVLTSLLEAFAHTDLSGKVFVFPRESVTDHVNLITPLEKPL
QNFTLCFRAYSDLSRAYSLFSYNTQGRDNELLVYKERVGEYSLYIGRHKVTSKVIE
KFPAPVHICVSWESSSGIAEFWINGTPLVKKGLRQGYFVEAQPKIVLGQEQDSYGG
KFDRSQSFVGEIGDLYMWDSVLPPENILSAYQGTPLPANILDWQALNYEIRGYVIIK
PLVWVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHE
ALHNHYTQKSLSLSPGKLGGGGSGGGGSGGGGSEPKSCDKTHTCPPCPAPELLGG
PSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDG
SFFLYSKLTVDKSRWQQGNVFSCSVMHEALHNHYTQKSLSLSPGK SEQ ID NO: 37: (Nucleic acid = First primer for SAP amplification in
example 1)
ACTTGGTCGACACCATGAACAAGCCGCTGCTTTG SEQ ID NO: 38: (Nucleic acid = Second primer for SAP amplification in
example 1)
ACTAGGTCGACCCACACCAAGGGTTTGA SEQ ID NO: 39: (Nucleic acid = First primer for the amplification of the
fragment of an Fc region of a human antibody in example 1)
CTCGAGCCCAAATCTTGTGACAA SEQ ID NO: 40: (Nucleic acid = Second primer for the amplification of the
fragment of an Fc region of a human antibody in example 1)
TCCGGAGCACTCATTTACCCGGAGAC SEQ ID NO: 41: (Nucleic acid = First primer for the amplification of the first
fragment of an Fc region of a human antibody in example 2)
ATACTCTCGAGCCCAAATCTTGTGACAA SEQ ID NO: 42: (Nucleic acid = Second primer for the amplification of the
first fragment of an Fc region of a human antibody in example 2)
ATCTGAAGCTTACCCGGAGACAGGGAGA SEQ ID NO: 43: (Nucleic acid = First primer for the amplification of the
second fragment of an Fc region of a human antibody in example 2)
AAGTAAGATCTGAGCCCAAATCTTGTGACAA SEQ ID NO: 44: (Nucleic acid = Second primer for the amplification of the
second fragment of an Fc region of a human antibody in example 2)
ATCTGTCCGGAGCACTCATTTACCCGGAGAC SEQ ID NO: 45: (Nucleic acid = First primer for the amplification of the
spacer chain in example 2)
AAGCTTGGTGGAGGCGGTTCAGG SEQ ID NO: 46: (Nucleic acid = Second primer for the amplification of the
spacer chain in example 2)
GGATCCGCCACCGCCAGAGCCA
```

The invention claimed is:

1. A method for treating systemic amyloidosis comprising administering an effective amount of a chimeric protein comprising one human serum amyloid P component (SAP), a first Fc region of a human antibody and a second Fc region of a human antibody,
   wherein the human SAP and the first Fc region are bonded to each other by a first hinge region,
   wherein the first and second Fc region are bonded to each other covalently by means of a bond formed from a spacer chain and a second hinge region, and wherein the first and second Fc region form a single polypeptide chain constituting a functional dimeric Fc region.

2. The method of claim 1, wherein the human SAP comprises an amino acid sequence having at least 80% identity with SEQ ID NO: 1.

3. The method of claim 1, wherein the first Fc region of a human antibody comprises at least one amino acid sequence having at least 80% identity with SEQ ID NO: 3.

4. The method of claim 1, wherein the first Fc region comprises at least two modifications in its amino acid sequence selected from:
   (i) a modification in the amino acid sequence selected from the group consisting of 378V, 378T, 434Y and 434S, and
   (ii) at least one modification in the amino acid sequence selected from the group consisting of 226G, 230S, 230T, 230L, 241 L, 264E, 307P, 315D, 330V, 362R, 378V, 378T, 389T, 389K, 434Y and 434S,
   wherein numbering of amino acids of the Fc region is that of the EU index proposed by Kabat, and wherein modification (i) does not occur at the same amino acid position as modification (ii).

5. The method of claim 1, wherein the first hinge region comprises at least one amino acid sequence having at least 60% identity with a sequence selected from SEQ ID NOs: 13 and 15 to 18.

6. The method of claim 1, wherein said chimeric protein further comprises at least one non-structuring peptide sequence between the first hinge region and the human SAP.

7. The method of claim 1, wherein the first and the second Fc region are identical.

8. The method of claim 1, wherein the spacer chain is represented by at least the amino acid sequence SEQ ID NO: 5.

9. The method of claim 1, wherein the systemic amyloidosis is an amyloidosis of AL type.

10. The method of claim 1, further comprising a step of administering a second active agent selected from the group consisting of 4-[bis(chloroethyl)amino]phenylalanine; 9-fluoro-1β,17,21-trihydroxy-16a-methylpregna-1,4-diene-3,20-dione; prednisone; dimethyl; sulfoxide; N [(7S)-5,6,7,9-tetrahydro-1,2,3,10-tetramethoxy-9-oxobenzo[a]heptalen-7-yl)acetamide]; (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione; bis-d-proline type; (R)-1-[6-[(R)-2-carboxypyrrolidin-I-yl]-6-oxohexanoyl]pyrrolidine-2-carboxylic acid; proteasome inhibitors; and mixtures thereof.

11. The method of claim 10, wherein the proteasome inhibitors are bortezomib, carfilzomib, marizomib, ixazomib, delanzomib, ONX-912, or revlimid.

12. The method of claim 1, wherein the chimeric protein is administered via intravenous, subcutaneous, or intramuscular route.

13. The method of claim 1, wherein the first Fc and the second Fc region are not identical.

14. The method of claim 1, wherein the first hinge and the second hinge region are identical.

15. The method of claim 1, wherein the first hinge and the second hinge region are not identical.

* * * * *

UNITED STATES PATENT AND TRADEMARK OFFICE
CERTIFICATE OF CORRECTION

PATENT NO. : 11,345,730 B2
APPLICATION NO. : 15/977489
DATED : May 31, 2022
INVENTOR(S) : Christophe de Romeuf et al.

It is certified that error appears in the above-identified patent and that said Letters Patent is hereby corrected as shown below:

In the Claims

At Column 101, Claim number 4, Line number 55, delete "241 L" and insert --241L--.
At Column 101, Claim number 4, Line number 56, delete "434S," and insert --434S;--.
At Column 102, Claim number 10, Line number 43, delete "dimethyl; sulfoxide" and insert --dimethyl sulfoxide--.
At Column 102, Claim number 10, Line numbers 49-50, delete "(R)-1-[6-[(R)-2-carboxypyrroli-din-l-yl]-6-oxohexanoyl]pyrrolidine-2-carboxylic acid" and insert --(R)-1-[6-[(R)-2-carboxypyrroli-din-1-yl]-6-oxohexanoyl]pyrrolidine-2-carboxylic acid--.

Signed and Sealed this
Eleventh Day of April, 2023

Katherine Kelly Vidal
*Director of the United States Patent and Trademark Office*

SEQUENCE LISTING

<160> NUMBER OF SEQ ID NOS: 46

<210> SEQ ID NO 1
<211> LENGTH: 204
<212> TYPE: PRT
<213> ORGANISM: Homo sapiens
<220> FEATURE:
<221> NAME/KEY: SOURCE
<222> LOCATION: 1..204
<223> OTHER INFORMATION: /mol_type="protein"
      /note="Human SAP"
      /organism="Homo sapiens"

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 2
<211> LENGTH: 612
<212> TYPE: DNA
<213> ORGANISM: Homo sapiens
<220> FEATURE:
<221> NAME/KEY: source
<222> LOCATION: 1..612
<223> OTHER INFORMATION: /mol_type="DNA"
      /note="Huamn SAP"
      /organism="Homo sapiens"

<400> SEQUENCE: 2
cacacagacc tcagtgggaa ggtgtttgta tttcctagag aatctgttac tgatcatgta      60
aacttgatca caccgctgga gaagcctcta cagaacttta ccttgtgttt tcgagcctat     120
agtgatctct ctcgtgccta cagcctcttc tcctacaata cccaaggcag ggataatgag     180
ctactagttt ataagaaag agttggagag tatagtctat acattggaag acacaaagtt     240
acatccaaag ttatcgaaaa gttcccggct ccagtgcaca tctgtgtgag ctgggagtcc     300

```
tcatcaggta ttgctgaatt ttggatcaat gggacacctt tggtgaaaaa gggtctgcga    360
cagggttact ttgtggaagc tcagcccaag attgtcctgg ggcaggaaca ggattcctat    420
gggggcaagt tgataggag ccagtccttt gtgggagaga ttggggattt gtacatgtgg    480
gactctgtgc tgcccccaga aaatatcctg tctgcctatc agggtacccc tctccctgcc    540
aatatcctgg actggcaggc tctgaactat gaaatcagag gatatgtcat catcaaaccc    600
ttggtgtggg tc                                                       612
```

```
<210> SEQ ID NO 3
<211> LENGTH: 217
<212> TYPE: PRT
<213> ORGANISM: Homo sapiens
<220> FEATURE:
<221> NAME/KEY: SOURCE
<222> LOCATION: 1..217
<223> OTHER INFORMATION: /mol_type="protein"
     /note="Fragment of Fc region of a human antibody"
     /organism="Homo sapiens"

<400> SEQUENCE: 3
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

```
<210> SEQ ID NO 4
<211> LENGTH: 654
<212> TYPE: DNA
<213> ORGANISM: Homo sapiens
<220> FEATURE:
<221> NAME/KEY: source
<222> LOCATION: 1..654
<223> OTHER INFORMATION: /mol_type="DNA"
     /note="Fragment of Fc region of a human antibody"
     /organism="Homo sapiens"
```

<400> SEQUENCE: 4

```
gcacctgaac tcctgggggg accgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaaccatctc caaagccaaa gggcagcccc gagaaccaca ggtgtacacc   360
ctgcccccat cccgggagga tgaccaag aaccaggtca gcctgacctg cctggtcaaa    420
ggcttctatc ccagcgacat cgccgtggag tgggagagca atgggcagcc ggagaacaac   480
tacaagacca cgcctcccgt gctggactcc gacggctcct tcttcctcta cagcaagctc   540
accgtggaca agagcaggtg gcagcagggg aacgtcttct catgctccgt gatgcatgag   600
gctctgcaca accactacac gcagaagagc ctctccctgt ctccgggtaa atga         654
```

<210> SEQ ID NO 5
<211> LENGTH: 5
<212> TYPE: PRT
<213> ORGANISM: artificial sequences
<220> FEATURE:
<221> NAME/KEY: SOURCE
<222> LOCATION: 1..5
<223> OTHER INFORMATION: /mol_type="protein"
      /note="Non-structuring sequence or spacer chain"
      /organism="artificial sequences"

<400> SEQUENCE: 5

Gly Gly Gly Gly Ser
1               5

<210> SEQ ID NO 6
<211> LENGTH: 43
<212> TYPE: DNA
<213> ORGANISM: artificial sequences
<220> FEATURE:
<221> NAME/KEY: source
<222> LOCATION: 1..43
<223> OTHER INFORMATION: /mol_type="DNA"
      /note="Non-structuring peptide sequence or spacer chain"
      /organism="artificial sequences"

<400> SEQUENCE: 6

```
cttggtggag gcggttcagg cggaggtggc tctggcggtg gcg                      43
```

<210> SEQ ID NO 7
<211> LENGTH: 436
<212> TYPE: PRT
<213> ORGANISM: artificial sequences
<220> FEATURE:
<221> NAME/KEY: SOURCE
<222> LOCATION: 1..436
<223> OTHER INFORMATION: /mol_type="protein"
      /note="secreted monomeric SAP-Fc "
      /organism="artificial sequences"

<400> SEQUENCE: 7

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser

```
            35                  40                  45
Leu Phe Ser Tyr Asn Thr Gln Gly Arg Asp Asn Glu Leu Leu Val Tyr
 50                  55                  60

Lys Glu Arg Val Gly Glu Tyr Ser Leu Tyr Ile Gly Arg His Lys Val
 65                  70                  75                  80

Thr Ser Lys Val Ile Glu Lys Phe Pro Ala Pro Val His Ile Cys Val
                     85                  90                  95

Ser Trp Glu Ser Ser Gly Ile Ala Glu Phe Trp Ile Asn Gly Thr
                    100                 105                 110

Pro Leu Val Lys Lys Gly Leu Arg Gln Gly Tyr Phe Val Glu Ala Gln
                115                 120                 125

Pro Lys Ile Val Leu Gly Gln Glu Gln Asp Ser Tyr Gly Gly Lys Phe
130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
                180                 185                 190

Arg Gly Tyr Val Ile Ile Lys Pro Leu Val Trp Val Glu Pro Lys Ser
                195                 200                 205

Cys Asp Lys Thr His Thr Cys Pro Pro Cys Pro Ala Pro Glu Leu Leu
210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
                260                 265                 270

Val His Asn Ala Lys Thr Lys Pro Arg Glu Glu Gln Tyr Asn Ser Thr
                275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
                340                 345                 350

Ser Leu Thr Cys Leu Val Lys Gly Phe Tyr Pro Ser Asp Ile Ala Val
                355                 360                 365

Glu Trp Glu Ser Asn Gly Gln Pro Glu Asn Asn Tyr Lys Thr Thr Pro
                370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
                420                 425                 430

Ser Pro Gly Lys
                435

<210> SEQ ID NO 8
```

<211> LENGTH: 1311
<212> TYPE: DNA
<213> ORGANISM: artificial sequences
<220> FEATURE:
<221> NAME/KEY: source
<222> LOCATION: 1..1311
<223> OTHER INFORMATION: /mol_type="DNA"
      /note="secreted monomeric SAP-Fc "
      /organism="artificial sequences"

<400> SEQUENCE: 8

```
cacacagacc tcagtgggaa ggtgtttgta tttcctagag aatctgttac tgatcatgta      60
aacttgatca caccgctgga gaagcctcta cagaactta ccttgtgttt tcgagcctat     120
agtgatctct ctcgtgccta cagcctcttc tcctacaata cccaaggcag ggataatgag     180
ctactagttt ataagaaag agttggagag tatagtctat acattggaag acacaaagtt     240
acatccaaag ttatcgaaaa gttcccggct ccagtgcaca tctgtgtgag ctgggagtcc     300
tcatcaggta ttgctgaatt ttggatcaat gggacacctt tggtgaaaaa gggtctgcga     360
cagggttact ttgtggaagc tcagcccaag attgtcctgg gcaggaaca ggattcctat     420
ggggcaagt ttgataggag ccagtccttt gtgggagaga ttggggattt gtacatgtgg     480
gactctgtgc tgccccaga aaatatcctg tctgcctatc agggtacccc ctctccctgcc     540
aatatcctgg actggcaggc tctgaactat gaaatcagag gatatgtcat catcaaaccc     600
ttggtgtggg tcgagcccaa atcttgtgac aaaactcaca catgcccacc gtgcccagca     660
cctgaactcc tggggggacc gtcagtcttc ctcttccccc caaaacccaa ggacaccctc     720
atgatctccc ggacccctga ggtcacatgc gtggtggtgg acgtgagcca cgaagaccct     780
gaggtcaagt tcaactggta cgtggacggc gtggaggtgc ataatgccaa gacaaagccg     840
cgggaggagc agtacaacag cacgtaccgt gtggtcagcg tcctcaccgt cctgcaccag     900
gactggctga atggcaagga gtacaagtgc aaggtctcca acaaagccct cccagccccc     960
atcgagaaaa ccatctccaa agccaaaggg cagccccgag aaccacaggt gtacaccctg    1020
cccccatccc gggaggagat gaccaagaac caggtcagcc tgacctgcct ggtcaaaggc    1080
ttctatccca gcgacatcgc cgtggagtgg gagagcaatg ggcagccgga gaacaactac    1140
aagaccacgc ctcccgtgct ggactccgac ggctccttct tcctctacag caagctcacc    1200
gtggacaaga gcaggtggca gcaggggaac gtcttctcat gctccgtgat gcatgaggct    1260
ctgcacaacc actacacgca gaagagcctc tccctgtctc cgggtaaatg a              1311
```

<210> SEQ ID NO 9
<211> LENGTH: 684
<212> TYPE: PRT
<213> ORGANISM: artificial sequences
<220> FEATURE:
<221> NAME/KEY: SOURCE
<222> LOCATION: 1..684
<223> OTHER INFORMATION: /mol_type="protein"
      /note="Secreted monomeric SAP-ScFc"
      /organism="artificial sequences"

<400> SEQUENCE: 9

```
His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45
```

```
Leu Phe Ser Tyr Asn Thr Gln Gly Arg Asp Asn Glu Leu Leu Val Tyr
 50                  55                  60

Lys Glu Arg Val Gly Glu Tyr Ser Leu Tyr Ile Gly Arg His Lys Val
 65                  70                  75                  80

Thr Ser Lys Val Ile Glu Lys Phe Pro Ala Pro Val His Ile Cys Val
                 85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
            115                 120                 125

Pro Lys Ile Val Leu Gly Gln Glu Gln Asp Ser Tyr Gly Gly Lys Phe
130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
            195                 200                 205

Cys Asp Lys Thr His Thr Cys Pro Pro Cys Pro Ala Pro Glu Leu Leu
210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
            275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Thr Cys Leu Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys Leu Gly Gly Gly Gly Ser Gly Gly Gly Ser Gly
            435                 440                 445

Gly Gly Gly Ser Glu Pro Lys Ser Cys Asp Lys Thr His Thr Cys Pro
450                 455                 460

Pro Cys Pro Ala Pro Glu Leu Leu Gly Gly Pro Ser Val Phe Leu Phe
```

```
                465                 470                 475                 480
Pro Pro Lys Pro Lys Asp Thr Leu Met Ile Ser Arg Thr Pro Glu Val
            485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
            515                 520                 525

Arg Glu Glu Gln Tyr Asn Ser Thr Tyr Arg Val Val Ser Val Leu Thr
        530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
            595                 600                 605

Phe Tyr Pro Ser Asp Ile Ala Val Glu Trp Glu Ser Asn Gly Gln Pro
        610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
        675                 680
```

<210> SEQ ID NO 10
<211> LENGTH: 2055
<212> TYPE: DNA
<213> ORGANISM: artificial sequences
<220> FEATURE:
<221> NAME/KEY: source
<222> LOCATION: 1..2055
<223> OTHER INFORMATION: /mol_type="DNA"
    /note="Secreted monomeric SAP-ScFc"
    /organism="artificial sequences"

<400> SEQUENCE: 10

```
cacacagacc tcagtgggaa ggtgtttgta tttcctagag aatctgttac tgatcatgta      60
aacttgatca caccgctgga gaagcctcta cagaacttta ccttgtgttt tcgagcctat    120
agtgatctct ctcgtgccta cagcctcttc tcctacaata cccaaggcag ggataatgag    180
ctactagttt ataagaaag agttggagag tatagtctat acattggaag acacaaagtt    240
acatccaaag ttatcgaaaa gttcccggct ccagtgcaca tctgtgtgag ctgggagtcc    300
tcatcaggta ttgctgaatt ttggatcaat gggacacctt tggtgaaaaa gggtctgcga    360
cagggttact tgtgtggaagc tcagcccaag attgtcctgg ggcaggaaca ggattcctat    420
gggggcaagt tgataggag ccagtccttt gtgggagaga ttggggattt gtacatgtgg    480
gactctgtgc tgcccccaga aaatatcctg tctgcctatc agggtacccc ctctccctgcc   540
aatatcctgg actggcaggc tctgaactat gaaatcagag gatatgtcat catcaaaccc   600
ttggtgtggg tcgagcccaa atcttgtgac aaaactcaca catgcccacc gtgcccagca   660
cctgaactcc tggggggacc gtcagtcttc ctcttccccc caaaacccaa ggacaccctc   720
```

```
atgatctccc ggacccctga ggtcacatgc gtggtggtgg acgtgagcca cgaagaccct    780
gaggtcaagt tcaactggta cgtggacggc gtggaggtgc ataatgccaa gacaaagccg    840
cgggaggagc agtacaacag cacgtaccgt gtggtcagcg tcctcaccgt cctgcaccag    900
gactggctga atggcaagga gtacaagtgc aaggtctcca acaaagccct cccagccccc    960
atcgagaaaa ccatctccaa agccaaaggg cagccccgag aaccacaggt gtacaccctg   1020
cccccatccc gggaggagat gaccaagaac caggtcagcc tgacctgcct ggtcaaaggc   1080
ttctatccca gcgacatcgc cgtggagtgg gagagcaatg ggcagccgga gaacaactac   1140
aagaccacgc ctcccgtgct ggactccgac ggctccttct cctctatag caagctcacc    1200 gtggacaaga gcaggtggca gcaggggaac gtcttctcat gctccgtgat gcatgaggct   1260
ctgcacaacc actacacgca gaagagcctc tccctgtctc cgggtaagct tggtggaggc   1320
ggttcaggcg gaggtggctc tggcggtggc ggatctgagc ccaaatcttg tgacaaaact   1380
cacacatgcc caccgtgccc agcacctgaa ctcctggggg gaccgtcagt cttcctcttc   1440
cccccaaaac ccaaggacac cctcatgatc tcccggaccc ctgaggtcac atgcgtggtg   1500
gtggacgtga gccacgaaga ccctgaggtc aagttcaact ggtacgtgga cggcgtggag   1560
gtgcataatg ccaagacaaa gccgcgggag gagcagtaca acagcacgta ccgtgtggtc   1620
agcgtcctca ccgtcctgca ccaggactgg ctgaatggca aggagtacaa gtgcaaggtc   1680
tccaacaaag ccctcccagc ccccatcgag aaaaccatct ccaaagccaa agggcagccc   1740
cgagaaccac aggtgtacac cctgccccca tcccgggagg agatgaccaa gaaccaggtc   1800
agcctgacct gcctggtcaa aggcttctat cccagcgaca tcgccgtgga gtgggagagc   1860
aatgggcagc cggagaacaa ctacaagacc acgcctcccg tgctggactc cgacggctcc   1920
ttcttcctct acagcaagct caccgtggac aagagcaggt ggcagcaggg gaacgtcttc   1980
tcatgctccg tgatgcatga ggctctgcac aaccactaca cgcagaagag cctctccctg   2040
tctccgggta aatga                                                    2055
```

<210> SEQ ID NO 11
<211> LENGTH: 480
<212> TYPE: PRT
<213> ORGANISM: artificial sequences
<220> FEATURE:
<221> NAME/KEY: SOURCE
<222> LOCATION: 1..480
<223> OTHER INFORMATION: /mol_type="protein"
    /note="Hinge + two fragments of Fc region of human antibody of SAP-ScFc"
    /organism="artificial sequences"

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

```
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Glu Glu Met Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys Leu Gly Gly Gly Ser Gly Gly Gly
225                 230                 235                 240
Gly Gly Ser Gly Gly Gly Ser Glu Pro Lys Ser Cys Asp Lys Thr
                245                 250                 255
His Thr Cys Pro Pro Cys Pro Ala Pro Glu Leu Leu Gly Gly Pro Ser
            260                 265                 270
Val Phe Leu Phe Pro Pro Lys Pro Lys Asp Thr Leu Met Ile Ser Arg
        275                 280                 285
Thr Pro Glu Val Thr Cys Val Val Val Asp Val Ser His Glu Asp Pro
    290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Arg Glu Glu Met Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
    450                 455                 460
Leu His Asn His Tyr Thr Gln Lys Ser Leu Ser Leu Ser Pro Gly Lys
465                 470                 475                 480

<210> SEQ ID NO 12
<211> LENGTH: 1443
<212> TYPE: DNA
<213> ORGANISM: artificial sequences
<220> FEATURE:
<221> NAME/KEY: source
```

<222> LOCATION: 1..1443
<223> OTHER INFORMATION: /mol_type="DNA"
      /note="Hinge + two fragments of Fc region of human antibody of SA
      P-ScFc"
      /organism="artificial sequences"

<400> SEQUENCE: 12

| | | | | | |
|---|---|---|---|---|---|
| gagcccaaat | cttgtgacaa | aactcacaca | tgcccaccgt | gcccagcacc | tgaactcctg | 60 |
| gggggaccgt | cagtcttcct | cttccccca | aaacccaagg | acaccctcat | gatctcccgg | 120 |
| acccctgagg | tcacatgcgt | ggtggtggac | gtgagccacg | aagaccctga | ggtcaagttc | 180 |
| aactggtacg | tggacggcgt | ggaggtgcat | aatgccaaga | caaagccgcg | ggaggagcag | 240 |
| tacaacagca | cgtaccgtgt | ggtcagcgtc | ctcaccgtcc | tgcaccagga | ctggctgaat | 300 |
| ggcaaggagt | acaagtgcaa | ggtctccaac | aaagccctcc | cagcccccat | cgagaaaacc | 360 |
| atctccaaag | ccaaagggca | gccccgagaa | ccacaggtgt | acaccctgcc | cccatcccgg | 420 |
| gaggagatga | ccaagaacca | ggtcagcctg | acctgcctgg | tcaaaggctt | ctatcccagc | 480 |
| gacatcgccg | tggagtggga | gagcaatggg | cagccggaga | caactacaa | gaccacgcct | 540 |
| cccgtgctgg | actccgacgg | ctccttcttc | ctctatagca | agctcaccgt | ggacaagagc | 600 |
| aggtggcagc | aggggaacgt | cttctcatgc | tccgtgatgc | atgaggctct | gcacaaccac | 660 |
| tacacgcaga | agagcctctc | cctgtctccg | ggtaagcttg | gtggaggcgg | ttcaggcgga | 720 |
| ggtggctctg | gcggtggcgg | atctgagccc | aaatcttgtg | acaaaactca | cacatgccca | 780 |
| ccgtgcccag | cacctgaact | cctggggga | ccgtcagtct | tcctcttccc | cccaaaaccc | 840 |
| aaggacaccc | tcatgatctc | ccggaccccct | gaggtcacat | gcgtggtggt | ggacgtgagc | 900 |
| cacgaagacc | ctgaggtcaa | gttcaactgg | tacgtggacg | gcgtggaggt | gcataatgcc | 960 |
| aagacaaagc | cgcgggagga | gcagtacaac | agcacgtacc | gtgtggtcag | cgtcctcacc | 1020 |
| gtcctgcacc | aggactggct | gaatggcaag | gagtacaagt | gcaaggtctc | caacaaagcc | 1080 |
| ctcccagccc | ccatcgagaa | aaccatctcc | aaagccaaag | gcagccccg | agaaccacag | 1140 |
| gtgtacaccc | tgcccccatc | ccgggaggag | atgaccaaga | accaggtcag | cctgacctgc | 1200 |
| ctggtcaaag | gcttctatcc | cagcgacatc | gccgtggagt | gggagagcaa | tgggcagccg | 1260 |
| gagaacaact | acaagaccac | gcctcccgtg | ctggactccg | acggctcctt | cttcctctac | 1320 |
| agcaagctca | ccgtggacaa | gagcaggtgg | cagcagggga | acgtcttctc | atgctccgtg | 1380 |
| atgcatgagg | ctctgcacaa | ccactacacg | cagaagagcc | tctccctgtc | tccgggtaaa | 1440 |
| tga | | | | | | 1443 |

<210> SEQ ID NO 13
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /note="Hinge region of human IgG1"
      /organism="Homo sapiens"

<400> SEQUENCE: 13

Glu Pro Lys Ser Cys Asp Lys Thr His Thr Cys Pro Pro Cys Pro
1               5                   10                  15

<210> SEQ ID NO 14
<211> LENGTH: 23
<212> TYPE: DNA

-continued

```
<213> ORGANISM: Homo sapiens
<220> FEATURE:
<221> NAME/KEY: source
<222> LOCATION: 1..23
<223> OTHER INFORMATION: /mol_type="DNA"
      /note="Hinge region of human IgG1"
      /organism="Homo sapiens"

<400> SEQUENCE: 14
ctcacacatg cccaccgtgc cca                                              23

<210> SEQ ID NO 15
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /note="Hinge region of human IgG2"
      /organism="Homo sapiens"

<400> SEQUENCE: 15

Glu Arg Lys Cys Cys Val Glu Cys Pro Pro Cys Pro
1               5                   10

<210> SEQ ID NO 16
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /note="Hinge region of human IgG3"
      /organism="Homo sapiens"

<400> SEQUENCE: 16

Glu Leu Lys Thr Pro Leu Gly Asp Thr Thr His Thr Cys Pro Arg Cys
1               5                   10                  15
Pro

<210> SEQ ID NO 17
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /note="Hinge region of human IgG3"
      /organism="Homo sapiens"

<400> SEQUENCE: 17

Glu Pro Lys Ser Cys Asp Thr Pro Pro Pro Cys Pro Arg Cys Pro
1               5                   10                  15

<210> SEQ ID NO 18
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /note="Hinge region of human IgG4"
      /organism="Homo sapiens"

<400> SEQUENCE: 18
```

```
Glu Ser Lys Tyr Gly Pro Pro Cys Pro Ser Cys Pro
1               5                   10
```

<210> SEQ ID NO 19
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /note="Shortened hinge region of IgG1 "
      /organism="Homo sapiens"

<400> SEQUENCE: 19

```
Asp Lys Thr His Thr Cys Pro Pro Cys Pro
1               5                   10
```

<210> SEQ ID NO 20
<211> LENGTH: 19
<212> TYPE: PRT
<213> ORGANISM: Homo sapiens
<220> FEATURE:
<221> NAME/KEY: SOURCE
<222> LOCATION: 1..19
<223> OTHER INFORMATION: /mol_type="protein"
      /note="Natural signal peptide of SAP"
      /organism="Homo sapiens"

<400> SEQUENCE: 20

```
Met Asn Lys Pro Leu Leu Trp Ile Ser Val Leu Thr Ser Leu Leu Glu
1               5                   10                  15

Ala Phe Ala
```

<210> SEQ ID NO 21
<211> LENGTH: 57
<212> TYPE: DNA
<213> ORGANISM: Homo sapiens
<220> FEATURE:
<221> NAME/KEY: source
<222> LOCATION: 1..57
<223> OTHER INFORMATION: /mol_type="DNA"
      /note="Natural signal peptide of SAP"
      /organism="Homo sapiens"

<400> SEQUENCE: 21

```
atgaacaagc cgctcctttg gatctctgtc ctcaccagcc tcctggaagc ctttgct      57
```

<210> SEQ ID NO 22
<211> LENGTH: 23
<212> TYPE: PRT
<213> ORGANISM: Homo sapiens
<220> FEATURE:
<221> NAME/KEY: SOURCE
<222> LOCATION: 1..23
<223> OTHER INFORMATION: /mol_type="protein"
      /note="Human TIMP signal peptide MMP1"
      /organism="Homo sapiens"

<400> SEQUENCE: 22

```
Met Ala Pro Phe Glu Pro Leu Ala Ser Gly Ile Leu Leu Leu Leu Trp
1               5                   10                  15

Leu Ile Ala Pro Ser Arg Ala
            20
```

<210> SEQ ID NO 23
<211> LENGTH: 24
<212> TYPE: PRT

```
<213> ORGANISM: Homo sapiens
<220> FEATURE:
<221> NAME/KEY: SOURCE
<222> LOCATION: 1..24
<223> OTHER INFORMATION: /mol_type="protein"
      /note="human insulin signal peptide"
      /organism="Homo sapiens"

<400> SEQUENCE: 23

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 24
<211> LENGTH: 27
<212> TYPE: PRT
<213> ORGANISM: Homo sapiens
<220> FEATURE:
<221> NAME/KEY: SOURCE
<222> LOCATION: 1..27
<223> OTHER INFORMATION: /mol_type="protein"
      /note="human EPO signal peptide"
      /organism="Homo sapiens"

<400> SEQUENCE: 24

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 25
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="MB7 signal peptide "
      /organism="artificial sequences"

<400> SEQUENCE: 25

Met Arg Trp Ser Trp Ile Phe Leu Leu Leu Ser Ile Thr Ser Ala
1               5                   10                  15

Asn Ala

<210> SEQ ID NO 26
<211> LENGTH: 19
<212> TYPE: PRT
<213> ORGANISM: artificial sequences
<220> FEATURE:
<221> NAME/KEY: SOURCE
<222> LOCATION: 1..19
<223> OTHER INFORMATION: /mol_type="protein"
      /note="AMHRII signal peptide "
      /organism="artificial sequences"

<400> SEQUENCE: 26

Met Arg Trp Ser Trp Ile Phe Leu Phe Leu Leu Ser Ile Thr Ala Ser
1               5                   10                  15

Val His Cys

<210> SEQ ID NO 27
<211> LENGTH: 19
<212> TYPE: PRT
<213> ORGANISM: artificial sequences
```

```
<220> FEATURE:
<221> NAME/KEY: SOURCE
<222> LOCATION: 1..19
<223> OTHER INFORMATION: /mol_type="protein"
      /note="XXII49 signal peptide "
      /organism="artificial sequences"

<400> SEQUENCE: 27

Met Ala Trp Val Trp Thr Leu Leu Phe Leu Met Ala Ala Ala Gln Ser
1               5                   10                  15

Ala Gln Ala

<210> SEQ ID NO 28
<211> LENGTH: 680
<212> TYPE: DNA
<213> ORGANISM: artificial sequences
<220> FEATURE:
<221> NAME/KEY: SOURCE
<222> LOCATION: 1..680
<223> OTHER INFORMATION: /mol_type="DNA"
      /note="SAP"
      /organism="artificial sequences"

<400> SEQUENCE: 28
gtcgacacca tgaacaagcc gctctttgga tctctgtcct caccagcctc ctggaagcct    60
ttgctcacac agacctcagt gggaaggtgt ttgtatttcc tagagaatct gttactgatc   120
atgtaaactt gatcacaccg ctggagaagc tctacagaa cttttacctg tgttttcgag    180
cctatagtga tctctctcgt gcctacagcc tcttctccta caatacccaa ggcagggata   240
atgagctact agtttataaa gaaagagttg gagagtatag tctatacatt ggaagacaca   300
aagttacatc caaagttatc gaaaagttcc cggctccagt gcacatctgt gtgagctggg   360
agtcctcatc aggtattgct gaattttgga tcaatgggac acctttggtg aaaaagggtc   420
tgcgacaggg ttactttgtg aagctcagc ccaagattgt cctggggcag gaacaggatt    480
cctatggggg caagtttgat aggagccagt ccttttgtggg agagattggg gatttgtaca   540
tgtgggactc tgtgctgccc ccagaaaata tcctgtctgc ctatcagggt acccctctcc   600
ctgccaatat cctggactgg caggctctga actatgaaat cagaggatat gtcatcatca   660 aaccccttggt gtgggtcgac                                              680

<210> SEQ ID NO 29
<211> LENGTH: 722
<212> TYPE: DNA
<213> ORGANISM: artificial sequences
<220> FEATURE:
<221> NAME/KEY: source
<222> LOCATION: 1..722
<223> OTHER INFORMATION: /mol_type="DNA"
      /note="Fragment of the Fc region of a human antibody"
      /organism="artificial sequences"

<400> SEQUENCE: 29
atactctcga gcccaaatct tgtgacaaaa ctcacacatg cccaccgtgc ccagcacctg    60
aactcctggg gggaccgtca gtcttcctct tccccccaaa acccaaggac accctcatga   120
tctcccggac ccctgaggtc acatgcgtgg tggtggacgt gagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agcccttccca gcccccatcg   360 agaaaaccat ctccaaagcc aaagggcagc ccgagaacc acaggtgtac accctgcccc    420
```

-continued

```
catcccggga ggagatgacc aagaaccagg tcagcctgac ctgcctggtc aaaggcttct    480
atcccagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg ctccggacag    720
at                                                                  722
```

<210> SEQ ID NO 30
<211> LENGTH: 1368
<212> TYPE: DNA
<213> ORGANISM: artificial sequences
<220> FEATURE:
<221> NAME/KEY: source
<222> LOCATION: 1..1368
<223> OTHER INFORMATION: /mol_type="DNA"
     /note="Monomeric SAP-Fc"
     /organism="artificial sequences"

<400> SEQUENCE: 30

```
atgaacaagc cgctcctttg gatctctgtc ctcaccagcc tcctggaagc ctttgctcac     60
acagacctca gtgggaaggt gttttgtattt cctagagaat ctgttactga tcatgtaaac    120
ttgatcacac cgctggagaa gcctctacag aactttacct tgtgttttcg agcctatagt    180
gatctctctc gtgcctacag cctcttctcc tacaatacccc aaggcaggga taatgagcta    240
ctagtttata agaaagagt tggagagtat agtctataca ttggaagaca caaagttaca    300
tccaaagtta tcgaaaagtt cccggctcca gtgcacatct gtgtgagctg ggagtcctca    360
tcaggtattg ctgaattttg gatcaatggg acacctttgg tgaaaaaggg tctgcgacag    420
ggttactttg tggaagctca gcccaagatt gtcctggggc aggaacagga ttcctatggg    480
ggcaagtttg ataggagcca gtcctttgtg ggagagattg gggatttgta catgtgggac    540
tctgtgctgc ccccagaaaa tatcctgtct gcctatcagg gtacccctct ccctgccaat    600
atcctggact ggcaggctct gaactatgaa atcagaggat atgtcatcat caaacccttg    660
gtgtgggtcg agcccaaatc ttgtgacaaa actcacacat gcccaccgtg cccagcacct    720
gaactcctgg ggggaccgtc agtcttcctc ttccccccaa acccaaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc   1020
gagaaaacca tctccaaagc caaagggcag ccccgagaac cacaggtgta caccctgccc   1080
ccatcccggg aggagatgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctacagcaa gctcaccgtg   1260
gacaagagca ggtggcagca ggggaacgtc ttctcatgct ccgtgatgca tgaggctctg   1320
cacaaccact acacgcagaa gagcctctcc ctgtctccgg gtaaatga                1368
```

<210> SEQ ID NO 31
<211> LENGTH: 455
<212> TYPE: PRT
<213> ORGANISM: artificial sequences
<220> FEATURE:

```
<221> NAME/KEY: SOURCE
<222> LOCATION: 1..455
<223> OTHER INFORMATION: /mol_type="protein"
      /note="Monomeric SAP-Fc"
      /organism="artificial sequences"

<400> SEQUENCE: 31
```

| | | | | | | | | | | | | | |
|---|---|---|---|---|---|---|---|---|---|---|---|---|---|
| Met | Asn | Lys | Pro | Leu | Leu | Trp | Ile | Ser | Val | Leu | Thr | Ser | Leu | Leu | Glu |
| 1 | | | | 5 | | | | | 10 | | | | | 15 | |

| Ala | Phe | Ala | His | Thr | Asp | Leu | Ser | Gly | Lys | Val | Phe | Val | Phe | Pro | Arg |
|---|---|---|---|---|---|---|---|---|---|---|---|---|---|---|---|
| | | | 20 | | | | | 25 | | | | | 30 | | |

| Glu | Ser | Val | Thr | Asp | His | Val | Asn | Leu | Ile | Thr | Pro | Leu | Glu | Lys | Pro |
|---|---|---|---|---|---|---|---|---|---|---|---|---|---|---|---|
| | | | 35 | | | | | 40 | | | | | 45 | | |

| Leu | Gln | Asn | Phe | Thr | Leu | Cys | Phe | Arg | Ala | Tyr | Ser | Asp | Leu | Ser | Arg |
|---|---|---|---|---|---|---|---|---|---|---|---|---|---|---|---|
| | 50 | | | | | 55 | | | | | 60 | | | | |

| Ala | Tyr | Ser | Leu | Phe | Ser | Tyr | Asn | Thr | Gln | Gly | Arg | Asp | Asn | Glu | Leu |
|---|---|---|---|---|---|---|---|---|---|---|---|---|---|---|---|
| 65 | | | | | 70 | | | | | 75 | | | | | 80 |

| Leu | Val | Tyr | Lys | Glu | Arg | Val | Gly | Glu | Tyr | Ser | Leu | Tyr | Ile | Gly | Arg |
|---|---|---|---|---|---|---|---|---|---|---|---|---|---|---|---|
| | | | | 85 | | | | | 90 | | | | | 95 | |

| His | Lys | Val | Thr | Ser | Lys | Val | Ile | Glu | Lys | Phe | Pro | Ala | Pro | Val | His |
|---|---|---|---|---|---|---|---|---|---|---|---|---|---|---|---|
| | | | 100 | | | | | 105 | | | | | 110 | | |

| Ile | Cys | Val | Ser | Trp | Glu | Ser | Ser | Ser | Gly | Ile | Ala | Glu | Phe | Trp | Ile |
|---|---|---|---|---|---|---|---|---|---|---|---|---|---|---|---|
| | | | 115 | | | | | 120 | | | | | 125 | | |

| Asn | Gly | Thr | Pro | Leu | Val | Lys | Lys | Gly | Leu | Arg | Gln | Gly | Tyr | Phe | Val |
|---|---|---|---|---|---|---|---|---|---|---|---|---|---|---|---|
| | 130 | | | | | 135 | | | | | 140 | | | | |

| Glu | Ala | Gln | Pro | Lys | Ile | Val | Leu | Gly | Gln | Glu | Gln | Asp | Ser | Tyr | Gly |
|---|---|---|---|---|---|---|---|---|---|---|---|---|---|---|---|
| 145 | | | | | 150 | | | | | 155 | | | | | 160 |

| Gly | Lys | Phe | Asp | Arg | Ser | Gln | Ser | Phe | Val | Gly | Glu | Ile | Gly | Asp | Leu |
|---|---|---|---|---|---|---|---|---|---|---|---|---|---|---|---|
| | | | | 165 | | | | | 170 | | | | | 175 | |

| Tyr | Met | Trp | Asp | Ser | Val | Leu | Pro | Pro | Glu | Asn | Ile | Leu | Ser | Ala | Tyr |
|---|---|---|---|---|---|---|---|---|---|---|---|---|---|---|---|
| | | | 180 | | | | | 185 | | | | | 190 | | |

| Gln | Gly | Thr | Pro | Leu | Pro | Ala | Asn | Ile | Leu | Asp | Trp | Gln | Ala | Leu | Asn |
|---|---|---|---|---|---|---|---|---|---|---|---|---|---|---|---|
| | | | 195 | | | | | 200 | | | | | 205 | | |

| Tyr | Glu | Ile | Arg | Gly | Tyr | Val | Ile | Ile | Lys | Pro | Leu | Val | Trp | Val | Glu |
|---|---|---|---|---|---|---|---|---|---|---|---|---|---|---|---|
| | 210 | | | | | 215 | | | | | 220 | | | | |

| Pro | Lys | Ser | Cys | Asp | Lys | Thr | His | Thr | Cys | Pro | Pro | Cys | Pro | Ala | Pro |
|---|---|---|---|---|---|---|---|---|---|---|---|---|---|---|---|
| 225 | | | | | 230 | | | | | 235 | | | | | 240 |

| Glu | Leu | Leu | Gly | Gly | Pro | Ser | Val | Phe | Leu | Phe | Pro | Pro | Lys | Pro | Lys |
|---|---|---|---|---|---|---|---|---|---|---|---|---|---|---|---|
| | | | | 245 | | | | | 250 | | | | | 255 | |

| Asp | Thr | Leu | Met | Ile | Ser | Arg | Thr | Pro | Glu | Val | Thr | Cys | Val | Val | Val |
|---|---|---|---|---|---|---|---|---|---|---|---|---|---|---|---|
| | | | 260 | | | | | 265 | | | | | 270 | | |

| Asp | Val | Ser | His | Glu | Asp | Pro | Glu | Val | Lys | Phe | Asn | Trp | Tyr | Val | Asp |
|---|---|---|---|---|---|---|---|---|---|---|---|---|---|---|---|
| | | 275 | | | | | 280 | | | | | 285 | | | |

| Gly | Val | Glu | Val | His | Asn | Ala | Lys | Thr | Lys | Pro | Arg | Glu | Glu | Gln | Tyr |
|---|---|---|---|---|---|---|---|---|---|---|---|---|---|---|---|
| | 290 | | | | | 295 | | | | | 300 | | | | |

| Asn | Ser | Thr | Tyr | Arg | Val | Val | Ser | Val | Leu | Thr | Val | Leu | His | Gln | Asp |
|---|---|---|---|---|---|---|---|---|---|---|---|---|---|---|---|
| 305 | | | | | 310 | | | | | 315 | | | | | 320 |

| Trp | Leu | Asn | Gly | Lys | Glu | Tyr | Lys | Cys | Lys | Val | Ser | Asn | Lys | Ala | Leu |
|---|---|---|---|---|---|---|---|---|---|---|---|---|---|---|---|
| | | | | 325 | | | | | 330 | | | | | 335 | |

| Pro | Ala | Pro | Ile | Glu | Lys | Thr | Ile | Ser | Lys | Ala | Lys | Gly | Gln | Pro | Arg |
|---|---|---|---|---|---|---|---|---|---|---|---|---|---|---|---|
| | | | 340 | | | | | 345 | | | | | 350 | | |

| Glu | Pro | Gln | Val | Tyr | Thr | Leu | Pro | Pro | Ser | Arg | Glu | Glu | Met | Thr | Lys |
|---|---|---|---|---|---|---|---|---|---|---|---|---|---|---|---|
| | | | 355 | | | | | 360 | | | | | 365 | | |

| Asn | Gln | Val | Ser | Leu | Thr | Cys | Leu | Val | Lys | Gly | Phe | Tyr | Pro | Ser | Asp |
|---|---|---|---|---|---|---|---|---|---|---|---|---|---|---|---|
| | 370 | | | | | 375 | | | | | 380 | | | | |

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
    450                 455

<210> SEQ ID NO 32
<211> LENGTH: 654
<212> TYPE: DNA
<213> ORGANISM: artificial sequences
<220> FEATURE:
<221> NAME/KEY: source
<222> LOCATION: 1..654
<223> OTHER INFORMATION: /mol_type="DNA"
      /note="First fragment of Fc region of a human antibody"
      /organism="artificial sequences"

<400> SEQUENCE: 32
gcacctgaac tcctgggggg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaaccatctc caaagccaaa gggcagcccc gagaaccaca ggtgtacacc     360
ctgcccccat cccgggagga gatgaccaag aaccaggtca gcctgacctg cctggtcaaa     420
ggcttctatc cagcgacat cgccgtggag tgggagagca tgggcagcc ggagaacaac      480
tacaagacca cgcctcccgt gctggactcc gacggctcct tcttcctcta tagcaagctc     540
accgtggaca gagcaggtg gcagcagggg aacgtcttct catgctccgt gatgcatgag     600
gctctgcaca accactacac gcagaagagc ctctccctgt ctccgggtaa gctt           654

<210> SEQ ID NO 33
<211> LENGTH: 715
<212> TYPE: DNA
<213> ORGANISM: artificial sequences
<220> FEATURE:
<221> NAME/KEY: source
<222> LOCATION: 1..715
<223> OTHER INFORMATION: /mol_type="DNA"
      /note="Second fragment of Fc region of a human antibody"
      /organism="artificial sequences"

<400> SEQUENCE: 33
agatctgagc ccaaatcttg tgacaaaact cacacatgcc caccgtgccc agcacctgaa      60
ctcctggggg gaccgtcagt cttcctcttc ccccccaaaac ccaaggacac cctcatgatc    120
tcccggaccc ctgaggtcac atgcgtggtg gtggacgtga gccacgaaga ccctgaggtc    180
aagttcaact ggtacgtgga cggcgtggag gtgcataatg ccaagacaaa gccgcgggag    240
gagcagtaca acagcacgta ccgtgtggtc agcgtcctca ccgtcctgca ccaggactgg    300
ctgaatggca aggagtacaa gtgcaaggtc tccaacaaag ccctcccagc ccccatcgag    360
aaaaccatct ccaaagccaa agggcagccc cgagaaccac aggtgtacac cctgccccca    420

```
tcccgggagg agatgaccaa gaaccaggtc agcctgacct gcctggtcaa aggcttctat      480
cccagcgaca tcgccgtgga gtgggagagc aatgggcagc cggagaacaa ctacaagacc      540
acgcctcccg tgctggactc cgacggctcc ttcttcctct acagcaagct caccgtggac      600
aagagcaggt ggcagcaggg gaacgtcttc tcatgctccg tgatgcatga ggctctgcac      660
aaccactaca cgcagaagag cctctccctg tctccgggta atgagtgctc ccgga           715
```

<210> SEQ ID NO 34
<211> LENGTH: 51
<212> TYPE: DNA
<213> ORGANISM: artificial sequences
<220> FEATURE:
<221> NAME/KEY: source
<222> LOCATION: 1..51
<223> OTHER INFORMATION: /mol_type="DNA"
    /note="spacer chain"
    /organism="artificial sequences"

<400> SEQUENCE: 34

```
aagcttggtg gaggcggttc aggcggaggt ggctctggcg gtggcggatc c               51
```

<210> SEQ ID NO 35
<211> LENGTH: 2112
<212> TYPE: DNA
<213> ORGANISM: artificial sequences
<220> FEATURE:
<221> NAME/KEY: source
<222> LOCATION: 1..2112
<223> OTHER INFORMATION: /mol_type="DNA"
    /note="Monomeric SAP-ScFc"
    /organism="artificial sequences"

<400> SEQUENCE: 35

```
atgaacaagc cgctcctttg gatctctgtc ctcaccagcc tcctggaagc ctttgctcac       60
acagacctca gtgggaaggt gtttgtattt cctagagaat ctgttactga tcatgtaaac      120
ttgatcacac cgctggagaa gcctctacag aactttacct tgtgttttcg agcctatagt      180
gatctctctc gtgcctacag cctcttctct acaatacccc aaggcaggga taatgagcta      240
ctagtttata agaaagagt tggagagtat agtctataca ttggaagaca caagttaca       300 tccaaagtta tcgaaaagtt cccggctcca gtgcacatct gtgtgagctg ggagtcctca      360
tcaggtattg ctgaattttg gatcaatggg acacctttgg tgaaaaaggg tctgcgacag      420
ggttactttg tggaagctca gcccaagatt gtcctggggc aggaacagga ttcctatggg      480
ggcaagtttg ataggagcca gtcctttgtg ggagagattg ggatttgta catgtgggac      540 tctgtgctgc ccccagaaaa tatcctgtct gcctatcagg taccctctc cctgccaat      600 atcctggact ggcaggctct gaactatgaa atcagaggat atgtcatcat caaacccttg      660
gtgtgggtcg agcccaaatc ttgtgacaaa actcacacat gcccaccgtg cccagcacct      720
gaactcctgg gggaccgtc agtcttcctc ttccccccaa acccaagga caccctcatg      780 atctcccgga cccctgaggt cacatgcgtg gtggtggacg tgagccacga agaccctgag      840
gtcaagttca actggtacgt ggacggcgtg gaggtgcata atgccaagac aaagccgcgg      900
gaggagcagt acaacagcac gtaccgtgtg gtcagcgtcc tcaccgtcct gcaccaggac      960
tggctgaatg gcaaggagta caagtgcaag gtctccaaca aagccctccc agcccccatc     1020
gagaaaacca tctccaaagc caagggcag ccccgagaac cacaggtgta caccctgccc     1080
ccatcccggg aggagatgac caagaaccag gtcagcctga cctgcctggt caaaggcttc     1140
```

```
tatcccagcg acatcgccgt ggagtgggag agcaatgggc agccggagaa caactacaag   1200
accacgcctc ccgtgctgga ctccgacggc tccttcttcc tctatagcaa gctcaccgtg   1260
gacaagagca ggtggcagca ggggaacgtc ttctcatgct ccgtgatgca tgaggctctg   1320
cacaaccact acacgcagaa gagcctctcc ctgtctccgg gtaagcttgg tggaggcggt   1380
tcaggcggag gtggctctgg cggtggcgga tctgagccca atcttgtga caaaactcac   1440 acatgcccac cgtgcccagc acctgaactc ctggggggac cgtcagtctt cctcttcccc   1500
ccaaaaccca aggacaccct catgatctcc cggacccctg aggtcacatg cgtggtggtg   1560
gacgtgagcc acgaagaccc tgaggtcaag ttcaactggt acgtggacgg cgtggaggtg   1620
cataatgcca agacaaagcc gcgggaggag cagtacaaca gcacgtaccg tgtggtcagc   1680
gtcctcaccg tcctgcacca ggactggctg aatggcaagg agtacaagtg caaggtctcc   1740
aacaaagccc tcccagcccc catcgagaaa accatctcca aagccaaagg gcagccccga   1800
gaaccacagg tgtacaccct gcccccatcc cgggaggaga tgaccaagaa ccaggtcagc   1860
ctgacctgcc tggtcaaagg cttctatccc agcgacatcg ccgtggagtg ggagagcaat   1920
gggcagccgg agaacaacta caagaccacg cctcccgtgc tggactccga cggctccttc   1980
ttcctctaca gcaagctcac cgtggacaag agcaggtggc agcagggaa cgtcttctca   2040 tgctccgtga tgcatgaggc tctgcacaac cactacacgc agaagagcct ctccctgtct   2100
ccgggtaaat ga                                                      2112
```

<210> SEQ ID NO 36
<211> LENGTH: 703
<212> TYPE: PRT
<213> ORGANISM: artificial sequences
<220> FEATURE:
<221> NAME/KEY: SOURCE
<222> LOCATION: 1..703
<223> OTHER INFORMATION: /mol_type="protein"
    /note="Monomeric SAP-ScFc"
    /organism="artificial sequences"

<400> SEQUENCE: 36

```
Met Asn Lys Pro Leu Leu Trp Ile Ser Val Leu Thr Ser Leu Glu
1               5                   10                  15

Ala Phe Ala His Thr Asp Leu Ser Gly Lys Val Phe Val Phe Pro Arg
            20                  25                  30

Glu Ser Val Thr Asp His Val Asn Leu Ile Thr Pro Leu Glu Lys Pro
        35                  40                  45

Leu Gln Asn Phe Thr Leu Cys Phe Arg Ala Tyr Ser Asp Leu Ser Arg
    50                  55                  60

Ala Tyr Ser Leu Phe Ser Tyr Asn Thr Gln Gly Arg Asp Asn Glu Leu
65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
            100                 105                 110

Ile Cys Val Ser Trp Glu Ser Ser Gly Ile Ala Glu Phe Trp Ile
        115                 120                 125

Asn Gly Thr Pro Leu Val Lys Lys Gly Leu Arg Gln Gly Tyr Phe Val
    130                 135                 140

Glu Ala Gln Pro Lys Ile Val Leu Gly Gln Glu Gln Asp Ser Tyr Gly
145                 150                 155                 160

Gly Lys Phe Asp Arg Ser Gln Ser Phe Val Gly Glu Ile Gly Asp Leu
```

```
                165                 170                 175
Tyr Met Trp Asp Ser Val Leu Pro Pro Glu Asn Ile Leu Ser Ala Tyr
            180                 185                 190

Gln Gly Thr Pro Leu Pro Ala Asn Ile Leu Asp Trp Gln Ala Leu Asn
        195                 200                 205

Tyr Glu Ile Arg Gly Tyr Val Ile Ile Lys Pro Leu Val Trp Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Leu Gly Gly Gly Ser Gly Gly Gly
    450                 455                 460

Gly Ser Gly Gly Gly Ser Glu Pro Lys Ser Cys Asp Lys Thr His
465                 470                 475                 480

Thr Cys Pro Pro Cys Pro Ala Pro Glu Leu Leu Gly Gly Pro Ser Val
                485                 490                 495

Phe Leu Phe Pro Pro Lys Pro Lys Asp Thr Leu Met Ile Ser Arg Thr
            500                 505                 510

Pro Glu Val Thr Cys Val Val Val Asp Val Ser His Glu Asp Pro Glu
        515                 520                 525

Val Lys Phe Asn Trp Tyr Val Asp Gly Val Glu Val His Asn Ala Lys
    530                 535                 540

Thr Lys Pro Arg Glu Glu Gln Tyr Asn Ser Thr Tyr Arg Val Val Ser
545                 550                 555                 560

Val Leu Thr Val Leu His Gln Asp Trp Leu Asn Gly Lys Glu Tyr Lys
                565                 570                 575

Cys Lys Val Ser Asn Lys Ala Leu Pro Ala Pro Ile Glu Lys Thr Ile
            580                 585                 590
```

```
Ser Lys Ala Lys Gly Gln Pro Arg Glu Pro Gln Val Tyr Thr Leu Pro
        595                 600                 605

Pro Ser Arg Glu Glu Met Thr Lys Asn Gln Val Ser Leu Thr Cys Leu
    610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
                645                 650                 655

Asp Gly Ser Phe Phe Leu Tyr Ser Lys Leu Thr Val Asp Lys Ser Arg
            660                 665                 670

Trp Gln Gln Gly Asn Val Phe Ser Cys Ser Val Met His Glu Ala Leu
        675                 680                 685

His Asn His Tyr Thr Gln Lys Ser Leu Ser Leu Ser Pro Gly Lys
    690                 695                 700

<210> SEQ ID NO 37
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="First primer for the amplification of the SAP "
      /organism="artificial sequences"

<400> SEQUENCE: 37
acttggtcga caccatgaac aagccgctgc tttg                           34

<210> SEQ ID NO 38
<211> LENGTH: 28
<212> TYPE: DNA
<213> ORGANISM: artificial sequences
<220> FEATURE:
<221> NAME/KEY: source
<222> LOCATION: 1..28
<223> OTHER INFORMATION: /mol_type="DNA"
      /note="Second primer for the amplification of the SAP"
      /organism="artificial sequences"

<400> SEQUENCE: 38
actaggtcga cccacaccaa gggtttga                                  28

<210> SEQ ID NO 39
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="First primer for the amplification of the fragment of Fc r
      egion of a human antibody"
      /organism="artificial sequences"

<400> SEQUENCE: 39
ctcgagccca aatcttgtga caa                                       23

<210> SEQ ID NO 40
<211> LENGTH: 26
<212> TYPE: DNA
<213> ORGANISM: artificial sequences
<220> FEATURE:
<221> NAME/KEY: source
<222> LOCATION: 1..26
```

```
<223> OTHER INFORMATION: /mol_type="DNA"
      /note="Second primer for the amplification of the fragment of Fc
      region of a human antibody"
      /organism="artificial sequences"

<400> SEQUENCE: 40
tccggagcac tcatttaccc ggagac                                           26

<210> SEQ ID NO 41
<211> LENGTH: 28
<212> TYPE: DNA
<213> ORGANISM: artificial sequences
<220> FEATURE:
<221> NAME/KEY: source
<222> LOCATION: 1..28
<223> OTHER INFORMATION: /mol_type="DNA"
      /note="First primer for the amplification of the first fragment o
      f Fc region of a human antibody"
      /organism="artificial sequences"

<400> SEQUENCE: 41
atactctcga gcccaaatct tgtgacaa                                         28

<210> SEQ ID NO 42
<211> LENGTH: 28
<212> TYPE: DNA
<213> ORGANISM: artificial sequences
<220> FEATURE:
<221> NAME/KEY: source
<222> LOCATION: 1..28
<223> OTHER INFORMATION: /mol_type="DNA"
      /note="Second primer for the amplification of the first fragment
      of Fc region of a human antibody"
      /organism="artificial sequences"

<400> SEQUENCE: 42
atctgaagct tacccggaga cagggaga                                         28

<210> SEQ ID NO 43
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="First primer for the amplification of the second fragment
      of Fc region of a human antibody"
      /organism="artificial sequences"

<400> SEQUENCE: 43
aagtaagatc tgagcccaaa tcttgtgaca a                                     31

<210> SEQ ID NO 44
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="Second primer for the amplification of the second fragment
      of Fc region of a human antibody"
      /organism="artificial sequences"

<400> SEQUENCE: 44
atctgtccgg agcactcatt tacccggaga c                                     31

<210> SEQ ID NO 45
```

```
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="First primer for the amplification of the spacer chain"
      /organism="artificial sequences"

<400> SEQUENCE: 45
aagcttggtg gaggcggttc agg                                            23

<210> SEQ ID NO 46
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="Second primer for the amplification of the spacer chain"
      /organism="artificial sequences"

<400> SEQUENCE: 46
ggatccgcca ccgccagagc ca                                             22
```